United States Patent [19]

Folkman et al.

[11] Patent Number: 5,837,682
[45] Date of Patent: Nov. 17, 1998

[54] ANGIOSTATIN FRAGMENTS AND METHOD OF USE

[75] Inventors: M. Judah Folkman, Brookline; Michael S. O'Reilly, Winchester, both of Mass.; Yihai Cao, Stockholm, Sweden; Kim Lee Sim, Gaithersburg, Md.

[73] Assignee: The Children's Medical Center Corporation, Boston, Mass.

[21] Appl. No.: 612,788

[22] Filed: Mar. 8, 1996

[51] Int. Cl.[6] .................................................. C07K 14/00
[52] U.S. Cl. ............................... 514/12; 514/2; 530/300; 530/350
[58] Field of Search .................................... 530/350, 300; 514/2, 12; 435/212, 217

[56] References Cited

PUBLICATIONS

O'Reilly, et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

Ponting, et al., "Plasminogen: a structural review", *Blood Coagulation and Fibrinolysis*, vol. 3, pp. 605–614 (1992).

Lerch, et al., "Localization of Individual Lysine–Binding Regions in Human Plasminogen and Investigations on Their Complex–Forming Properties" *European Journal of Biochemistry*, vol. 107, No. 1, pp. 7–13 (1980).

Sambrook, J., et al., Molecular Cloning, XP002020900, pp. 17.37 –17.41 (1989).

Folkman J., Tumor angiogenesis: Therapeutic implications., *N. Engl. Jour. Med.* 285:1182 1186, 1971.

Algire GH, et al. Vascular reactions of normal and malignant tumors in vivo I. Vascular reactions of mice to wounds and to normal and neoplastic transplants. *J. Natl. Cancer Inst.* 6:73–85, 1945.

Folkman J. et al., Tumor behavior in isolated perfused organs: In vitro growth and metastasis of biopsy material in rabbit thyroid and canine intestinal segments. *Annals of Surgery* 164:491–502, 1966.

Gimbrone, M.A., Jr. et al., Tumor growth and neovascularization: An experimental model using the rabbit cornea. *J. Natl. Cancer Institute* 52:41–427, 1974.

Gimbrone MA Jr., et al., Tumor dormancy in vivo by prevention of neovascularization. *J. Exp. Med.* 136:261–276.

Knighton D., Avascular and vascular phases of tumor growth in the chick embryo. *British J. Cancer*, 35:347–356, 1977.

Lien W., et al., The blood supply of experimental liver metastases. II. A microcirculatory study of normal and tumor vessels of the liver with the use of perfused silicone rubber. *Surgery* 68:334–340, 1970.

Folkman J, et al, Induction of angiogenesis during the transition from hyperplasia to neoplasia. *Nature* 339:58–61, 1989.

Kim K J, et al., Inhibition of vascular endothelial growth factor–induced angiogenesis suppresses tumor growth in vivo, *Nature* 362:841–844, 1993.

Hori, A. et al., Suppression of solid tumor growth by immunoneutralizing monoclonal antibody against human basic fibroblast growth factor. *Cancer Research*, 51:6180–6184, 1991.

Gross JL, et al. Modulation of solid tumor growth in vivo by bFGF. *Proc. Amer. Assoc. Canc. Res.* 31:79, 1990.

Ingber D, et al., Angioinhibins: Synthetic analogues of fumagillin which inhibit angiogenesis and suppress tumor growth. *Nature*, 48:555–557, 1990.

Weidner N, et al., Tumor angiogenesis and metastasis — correlation in invasive breast carcinoma. *N. Engl. J. Med.* 324:1–8, 1991.

Weidner N, et al., Tumor angiogenesis: A new signficant and independent prognostic indicator in early–stage breast carcinoma, *J. Natl. Cancer Inst.* 84:1875–1887, 1992.

Weidner, N, Carroll PR, Flax, J, Blumenfeld W, Folkman J. Tumor angiogenesis correlates with metastasis in invasive prostate carcinoma. *American Journal of Pathology*, 143(2):401–409, 1993.

Srivastava A, et al., The prognostic significance of tumor vascularity in intermediate thickness (0.76–4.0 mm thick) skin melanoma. *Amer. J. Pathol.* 133:419–423, 1988.

Nguyen M, et al., Elevated levels of an angiogenic peptide, basic fibroblast growth factor, in urine of bladder cancer patients. *J. Natl. Cancer Inst.* 85:241–242, 1993.

Robbins, K.C., "The plasminogen–plasmin enzyme system" *Hemostasis and Thrombosis, Basic Principles and Practice*, 2nd Edition, ed. by Colman, R.W. et al J.B. Lippincott Company, pp. 340–357, 1987.

Yoshimura, T, et al., "Cloning, sequencing, and expression of human macrophage stimulating protein (MSP, MST1) confirms MSP as a member of the family of kringle proteins and locates the MSP gene on Chromosome 3" *J. Biol. Chem.*, vol. 268, No. 21, pp. 15461–15468, 1993.

Browne, M.J., et al., "Expression of recombinant human plasminogen and aglycoplasminogen in HeLa cells" Fibrinolysis vol. 5 (4), 257–260, 1991.

Brem et al., "Intersitial chemotherapy with drug polymer implants for treatment of recurrent gliomas," *J. Neurosurg.* 74:441–446 (1991).

Muthukkaruppan Vr., et al., Angiogenesis in the mouse cornea. *Science* 205:1416–1418, 1979.

(List continued on next page.)

*Primary Examiner*—Karen Cochrane Carlson
*Attorney, Agent, or Firm*—Jones & Askew

[57] ABSTRACT

Fragments of an endothelial cell proliferation inhibitor and method of use therefor are provided. The endothelial proliferation inhibitor is a protein derived from plasminogen, or more specifically is an angiostatin fragment. The angiostatin fragments generally correspond to kringle structures occurring within the endothelial cell proliferation inhibitor. The endothelial cell inhibiting activity of these fragments provides a means for inhibiting angiogenesis of tumors and for treating angiogenic-mediated disease.

10 Claims, 38 Drawing Sheets

PUBLICATIONS

Passaniti A, et al., "A simple, quantitative method for assessing angiogenesis and anti–angiogenic agents using reconstituted basement membrane, heparin and fibroblast growth factor," *Lab. Invest.,* vol. 67, p. 519 (1992).

Folkman J., Angiogenesis and its inhibitors in *"Importnat Advances in Oncology 1985"*, VT DeVita, S. Hellman and S. Rosenberg, editors, J.B. Lippincott, Philadelphia, 1985.

Obeso, et al., "Methods in Laboratory Investigation, A Hemangioendothelioma–derived cell line; Its use as a Model for the Study of Endothelial Cell Biology," *Lab. Invest.,* 63(2), pp. 259–262, 1990.

Sotrrup–Jensen, L., et al., *Progress in Chemical Fibrinolysis and Thrombolysis,* vol. 3, Davidson, J.F., et al. eds. Raven Press, New York, p. 191 (1978).

Grant, D.S., et al., "Scatter factor induces blood vessel formation in vivo," *Proc. Natl. Acad. Sci.,* vol. 90, pp. 1937–1941 (1993).

Shi, G. et al., "Kringle Domains and Plasma Denaturation," *Biochem. and Biophys. Res. Comm.,* vol. 178, No. 1, pp. 360–368 (1991).

Scaller, J. et al., "Structural Aspects of the Plasminogen of Various Species," *Enzyme,* vol. 40, pp. 63–69 (1988).

Wiman, B., et al., "On the Specific Interaction between the Lysine–binding sites in Plasmin and Complementary Sites in $<<_2$–Antiplasma and in Fibrinogen," *Biochemica et Biophysica Acta,* 579, 142 (1979).

Derwent Publications, Ltd., London; JP 58–036–391 (Sankyo KK) Mar. 3, 1983 (Abstract).

M. O'Reilly et al., "The Suppression of Tumor Metastases by a Primary Tumor" *Science* vol. 44, pp. 474–476; 1993.

T. E. Maione et al., "Inhibition of Angiogenesis by Recombinant Human Platelet Factor–4 and Related Peptides" *Science* vol. 247, pp. 77–79; Jan. 5, 1990.

M. A. Moses et al., "Identification of an Inhibitor of Neovascularization from Cartilage" *Science* vol. 248, pp. 1408–1410; Jun. 15, 1990.

O'Reilly, M.S. Holmgren, L., Shing,Y., Chen, C., Rosenthal, R.A., Moses, M., Lane, W.S., Cao, Y., Sage, E.H., and Folkman, J., *Cell* (1994) 79:315–328.

Brockway, W.J. et al., "Measurement of the Binding of Antifibrinolytic Amino Acids to Various Plasminogens" *Arch. Biochem. Biophys.* 151, 194–199 (1972).

Cleary, S. Mulkerrin et al., "Purification and Characterization of Tissue Plasminogen Activator Kringle–2 Domain Expressed in *Escherichia coli"*, *Biochem.* 28, 1884–1891 (1989).

Gunzler, W.A. et al., "The Primary Structure of High Molecular Mass Urokinase from Human Urine," *Hoppe–Seyler's Z. Physiol. Chem.* 363, 1155–1165 (1982).

Johansson, J. et al., "Surfactant Protein B: Disulfide Bridges, Structural Properties, and Kringle Similarities," *Biochem.* 30, 6917–6921 (1991).

Lokker, N.A. et al., "Mutational analysis and molecular modeling of the N–terminal kringle–containing domain of hepatocyte growth gactor identifies amino acid side chains important for interaction with the c–met receptor," *Prot. Engin.* 7, 895–903 (1994).

Marti, D. et al., "Expression, purification and characterization of the recombinant kringle 2 and kringle 3 domains of human plasminogen and analysis of their binding affinity for ω–aminocarboxylic acids," *Eur. J. Biochem.* 219; 455–462 (1994).

McLean, J.W. et al., cDNA sequence of human apolipoprotein(a) is homologous to plasminogen *Nature* 330, 132–137 (1987).

Menhart, N. et al., "Construction, Expression, and Purification of Recombinant Kringle 1 of Human Plasminogen and Analysis of Its Interaction with ω–Amino Acids," *Biochem.* 30, 1948–1957 (1991).

Powell, J. R. et al., "Amino Acid Sequence Analysis of the Asparagine–288 Region of the Carbohydrate Variants of Human Plasminogen," *Biochem.* 22, 923–927 (1983).

Walz, D.A. et al., "Amino acid sequence of human prothrombin fragments 1 and 2," *Proc. Natl. Acad. Sci.* 74, 1969–1973 (1977).

Mouse Plasminogen Sequence:

```
met asp his lys glu val ile leu leu phe leu leu leu leu lys
pro gly gln gly asp ser leu asp gly tyr ile ser thr gln gly
ala ser leu phe ser leu thr lys lys gln leu ala ala gly gly
val ser asp cys leu ala lys cys glu gly glu thr asp phe val
cys arg ser phe gln tyr his ser lys glu gln gln cys val ile
met ala glu asn ser lys thr ser ser ile ile arg met arg asp
val ile leu phe glu lys arg val tyr leu ser glu cys lys thr
gly ile gly asn gly tyr arg gly thr met ser arg thr lys ser
gly val ala cys gln lys trp gly ala thr phe pro his val pro
asn tyr ser pro ser thr his pro asn glu gly leu glu glu asn
tyr cys arg asn pro asp asn asp glu gln gly pro trp cys tyr
thr thr asp pro asp lys arg tyr asp tyr cys asn ile pro glu
cys glu glu glu cys met tyr cys ser gly glu lys tyr glu gly
lys ile ser lys thr met ser gly leu asp cys gln ala trp asp
ser gln ser pro his ala his gly tyr ile pro ala lys phe pro
ser lys asn leu lys met asn tyr cys his asn pro asp gly glu
pro arg pro trp cys phe thr thr asp pro thr lys arg trp glu
tyr cys asp ile pro arg cys thr thr pro pro pro pro pro ser
pro thr tyr gln cys leu lys gly arg gly glu asn tyr arg gly
thr val ser val thr val ser gly lys thr cys gln arg trp ser
glu gln thr pro his arg his asn arg thr pro glu asn phe pro
cys lys asn leu glu glu asn tyr cys arg asn pro asp gly glu
thr ala pro trp cys tyr thr thr asp ser gln leu arg trp glu
tyr cys glu ile pro ser cys glu ser ser ala ser pro asp gln
ser asp ser ser val pro pro glu glu gln thr pro val val gln
glu cys tyr gln ser asp gly gln ser tyr arg gly thr ser ser
thr thr ile thr gly lys lys cys gln ser trp ala ala met phe
pro his arg his ser lys thr pro glu asn phe pro asp ala gly
leu glu met asn tyr cys arg asn pro asp gly asp lys gly pro
trp cys tyr thr thr asp pro ser val arg trp glu tyr cys asn
leu lys arg cys ser glu thr gly gly ser val val glu leu pro
thr val ser gln glu pro ser gly pro ser asp ser glu thr asp
cys met tyr gly asn gly lys asp tyr arg gly lys thr ala val
thr ala ala gly thr pro cys gln gly trp ala ala gln glu pro
his arg his ser ile phe thr pro gln thr asn pro arg ala asp
leu glu lys asn tyr cys arg asn pro asp gly asp val asn gly
pro trp cys tyr thr thr asn pro arg lys leu tyr asp tyr cys
asp ile pro leu cys ala ser ala ser ser phe glu cys gly lys
pro gln val glu pro lys lys cys pro gly arg val val gly gly
cys val ala asn pro his ser trp pro trp gln ile ser leu arg
thr arg phe thr gly gln his phe cys gly gly thr leu ile ala
pro glu trp val leu thr ala ala his cys leu glu lys ser ser
arg pro glu phe tyr lys val ile leu gly ala his glu glu tyr
ile arg gly leu asp val gln glu ile ser val ala lys leu ile
leu glu pro asn asn arg asp ile ala leu leu lys leu ser arg
pro ala thr ile thr asp lys val ile pro ala cys leu pro ser
```

FIG. 1A

```
pro asn tyr met val ala asp arg thr ile cys tyr ile thr gly
trp gly glu thr gln gly thr phe gly ala gly arg leu lys glu
ala gln leu pro val ile glu asn lys val cys asn arg val glu
tyr leu asn asn arg val lys ser thr glu leu cys ala gly gln
leu ala gly gly val asp ser cys gln gly asp ser gly gly pro
leu val cys phe glu lys asp lys tyr ile leu gln gly val thr
ser trp gly leu gly cys ala arg pro asn lys pro gly val tyr
val arg val ser arg phe val asp trp ile glu arg glu met arg
asn asn
```

Fig. 1B

MOUSE
HUMAN
RHESUS MONKEY
PORCINE
BOVINE

```
val tyr leu ser glu cys lys thr gly ile gly asn gly tyr arg gly
val tyr leu ser glu cys lys thr gly asn gly lys asn tyr arg gly
val tyr leu ser glu cys lys thr gly asn gly lys asn tyr arg gly
ile tyr leu ser glu cys lys thr gly asn gly lys asn tyr arg gly
ile tyr leu leu glu cys lys thr gly asn gly gln thr tyr arg gly thr met ser arg thr lys ser gly val ala cys gln lys trp gly ala
thr met ser lys thr lys asn gly ile thr cys gln lys trp ser ser
thr met ser lys thr arg thr gly ile thr cys gln lys trp ser ser
thr thr ser lys thr lys ser gly val ile cys gln lys trp ser val
thr thr ala glu thr lys ser gly val thr cys gln lys trp ser ala thr phe pro his val pro asn tyr ser pro ser thr his pro asn glu
thr ser pro his arg pro arg phe ser pro ala thr his pro ser glu
thr ser pro his arg pro thr phe ser pro ala thr his pro ser glu
ser ser pro his ile pro lys tyr ser pro glu lys phe pro leu ala
thr ser pro his val pro lys phe ser pro glu lys phe pro leu ala gly leu glu glu asn tyr cys arg asn pro asp asn asp glu gln gly
gly leu glu glu asn tyr cys arg asn pro asp asn asp pro gln gly
gly leu glu glu asn tyr cys arg asn pro asp asn asp gly gln gly
gly leu glu glu asn tyr cys arg asn pro asp asn asp glu lys gly
gly leu glu glu asn tyr cys arg asn pro asp asn asp glu asn gly pro trp cys tyr thr thr asp pro asp lys arg tyr asp tyr cys asn
pro trp cys tyr thr thr asp pro glu lys arg tyr asp tyr cys asp
pro trp cys tyr thr thr asp pro glu glu arg phe asp tyr cys asp
pro trp cys tyr thr thr asp pro glu thr arg phe asp tyr cys asp
pro trp cys tyr thr thr asp pro asp lys arg tyr asp tyr cys asp ile pro glu cys glu glu glu cys met tyr cys ser gly glu lys tyr
ile leu glu cys glu glu glu cys met his cys ser gly glu asn tyr
ile pro glu cys glu asp glu cys met his cys ser gly glu asn tyr
ile pro glu cys glu asp glu cys met his cys ser gly glu his tyr
ile pro glu cys glu asp lys cys met his cys ser gly glu asn tyr glu gly lys ile ser lys thr met ser gly leu asp cys gln ala trp
asp gly lys ile ser lys thr met ser gly leu glu cys gln ala trp
asp gly lys ile ser lys thr met ser gly leu glu cys gln ala trp
glu gly lys ile ser lys thr met ser gly ile glu cys gln ser trp
glu gly lys ile ala lys thr met ser gly arg asp cys gln ala trp
```

FIG. 2A

```
asp ser gln ser pro his ala his gly tyr ile pro ala lys phe pro
asp ser gln ser pro his ala his gly tyr ile pro ser lys phe pro
asp ser gln ser pro his ala his gly tyr ile pro ser lys phe pro
gly ser gln ser pro his ala his gly tyr leu pro ser lys phe pro
asp ser gln ser pro his ala his gly tyr ile pro ser lys phe pro ser lys asn leu lys met asn tyr cys his asn pro asp gly glu pro
asn lys asn leu lys lys asn tyr cys arg asn pro asp arg glu leu
asn lys asn leu lys lys asn tyr cys arg asn pro asp gly glu pro
asn lys asn leu lys met asn tyr cys arg asn pro asp gly glu pro
asn lys asn leu lys met asn tyr cys arg asn pro asp gly glu pro arg pro trp cys phe thr thr asp pro thr lys arg trp glu tyr cys
arg pro trp cys phe thr thr asp pro asn lys arg trp glu leu cys
arg pro trp cys phe thr thr asp pro asn lys arg trp glu leu cys
arg pro trp cys phe thr thr asp pro asn lys arg trp glu phe cys
arg pro trp cys phe thr thr asp pro gln lys arg trp glu phe cys asp ile pro arg cys thr thr pro pro pro pro ser pro thr tyr
asp ile pro arg cys thr thr pro pro pro ser ser gly pro thr tyr
asp ile pro arg cys thr thr pro pro pro ser ser gly pro thr tyr
asp ile pro arg cys thr thr pro pro pro thr ser gly pro thr tyr
asp ile pro arg cys thr thr pro pro pro ser ser gly pro lys tyr gln cys leu lys gly arg gly glu asn tyr arg gly thr val ser val
gln cys leu lys gly thr gly glu asn tyr arg gly asn val ala val
gln cys leu lys gly thr gly glu asn tyr arg gly asp val ala val
gln cys leu lys gly arg gly glu asn tyr arg gly thr val ser val
gln cys leu lys gly thr gly lys asn tyr gly gly thr val ala val thr val ser gly lys thr cys gln arg trp ser glu gln thr pro his
thr val ser gly his thr cys gln his trp ser ala gln thr pro his
thr val ser gly his thr cys his gly trp ser ala gln thr pro his
thr ala ser gly his thr cys gln arg trp ser ala gln ser pro his
thr glu ser gly his thr cys gln arg trp ser glu gln thr pro his arg his asn arg thr pro glu asn phe pro cys lys asn leu glu glu
thr his asn arg thr pro glu asn phe pro cys lys asn leu asp glu
thr his asn arg thr pro glu asn phe pro cys lys asn leu asp glu
lys his asn arg thr pro glu asn phe pro cys lys asn leu glu glu
lys his asn arg thr pro glu asn phe pro cys lys asn leu glu glu asn tyr cys arg asn pro asp gly glu thr ala pro trp cys tyr thr
asn tyr cys arg asn pro asp gly lys arg ala pro trp cys his thr
asn tyr cys arg asn pro asp gly glu lys ala pro trp cys tyr thr
asn tyr cys arg asn pro asp gly glu thr ala pro trp cys tyr thr
asn tyr cys arg asn pro asp gly glu lys ala pro trp cys tyr thr
```

FIG. 2B

```
thr asp ser gln leu arg trp glu tyr cys glu ile pro ser cys glu
thr asn ser gln val arg trp glu tyr cys lys ile pro ser cys asp
thr asn ser gln val arg trp glu tyr cys lys ile pro ser cys glu
thr asp ser glu val arg trp asp tyr cys lys ile pro ser cys gly
thr asn ser glu val arg trp glu tyr cys thr ile pro ser cys glu ser ser ala ser pro asp gln ser asp ser ser val pro pro glu glu
ser ser pro val ser thr glu gln leu ala pro thr ala pro pro glu
ser ser pro val ser thr glu pro leu asp pro thr ala pro pro glu
ser ser thr thr ser thr glu his leu asp ala pro val pro pro glu
ser ser pro leu ser thr glu arg met asp val pro val pro pro glu gln thr pro val val gln glu cys tyr gln ser asp gly gln ser tyr
leu thr pro val val gln asp cys tyr his gly asp gly gln ser tyr
leu thr pro val val gln glu cys tyr his gly asp gly gln ser tyr
gln thr pro val ala gln asp cys tyr arg gly asn gly glu ser tyr
gln thr pro val pro gln asp cys tyr his gly asn gly gln ser tyr arg gly thr ser ser thr thr ile thr gly lys lys cys gln ser trp
arg gly thr ser ser thr thr thr thr gly lys lys cys gln ser trp
arg gly thr ser ser thr thr thr thr gly lys lys cys gln ser trp
arg gly thr ser ser thr thr ile thr gly arg lys cys gln ser trp
arg gly thr ser ser thr thr ile thr gly arg lys cys gln ser trp ala ala met phe pro his arg his ser lys thr pro glu asn phe pro
ser ser met thr pro his arg his gln lys thr pro glu asn tyr pro
ser ser met thr pro his trp his glu lys thr pro glu asn phe pro
val ser met thr pro his arg his glu lys thr pro gly asn phe pro

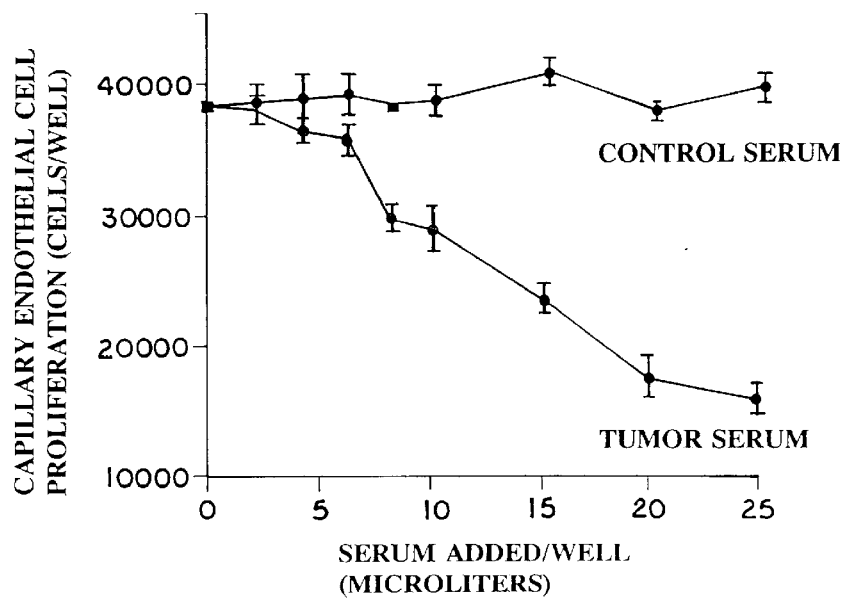
Fig_5
— ASCITES
— SERUM FROM MICE WITH ASCITES
— SERUM FROM NORMAL MICE
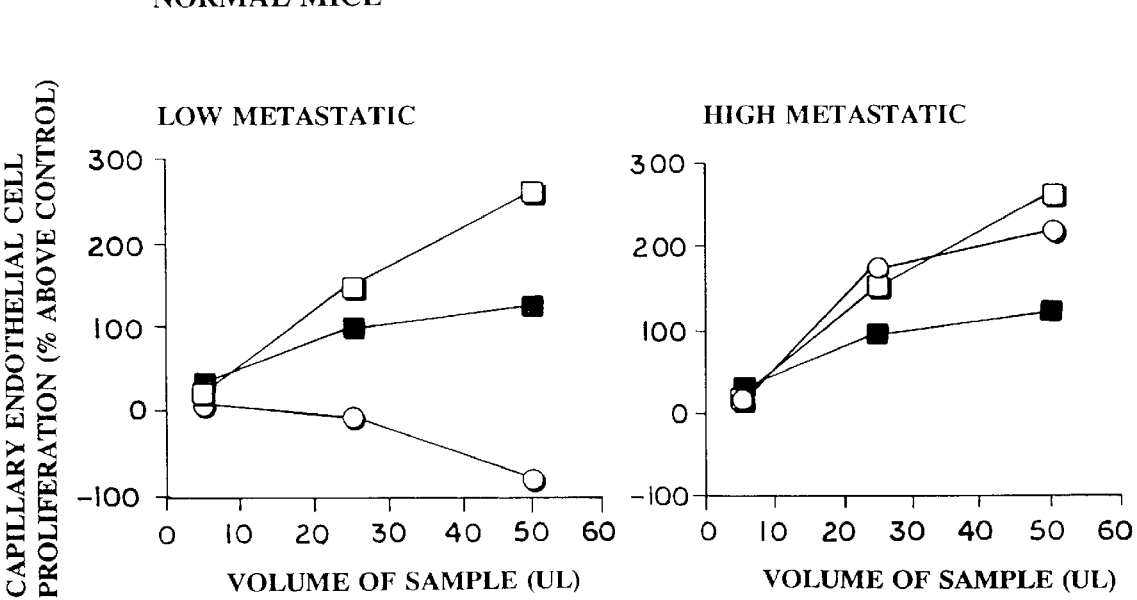
Fig_6A    Fig_6B

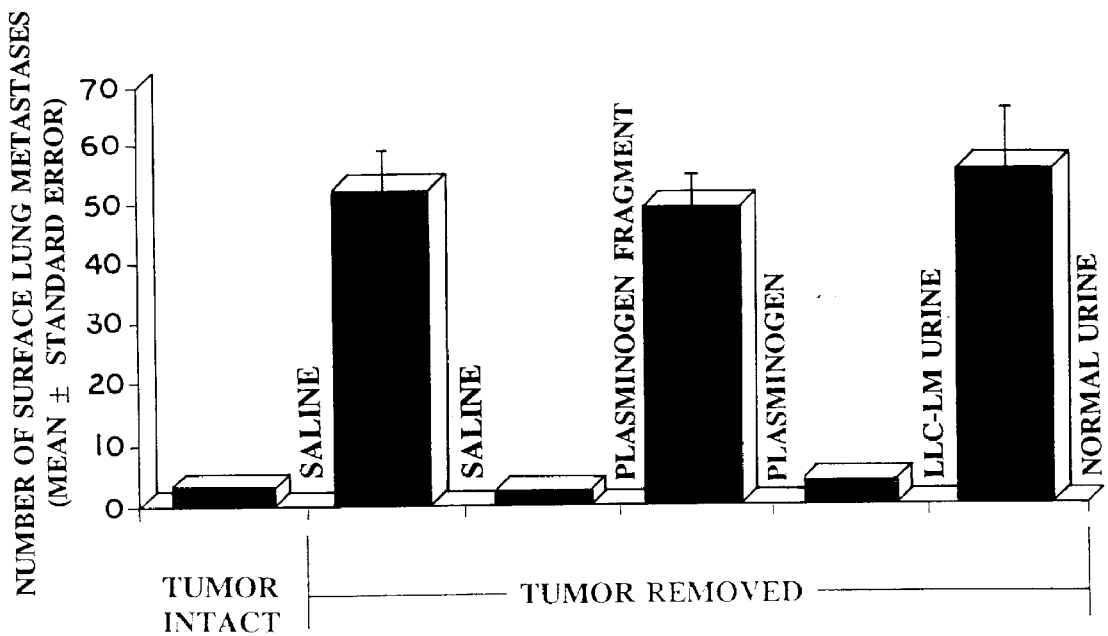
Fig_8
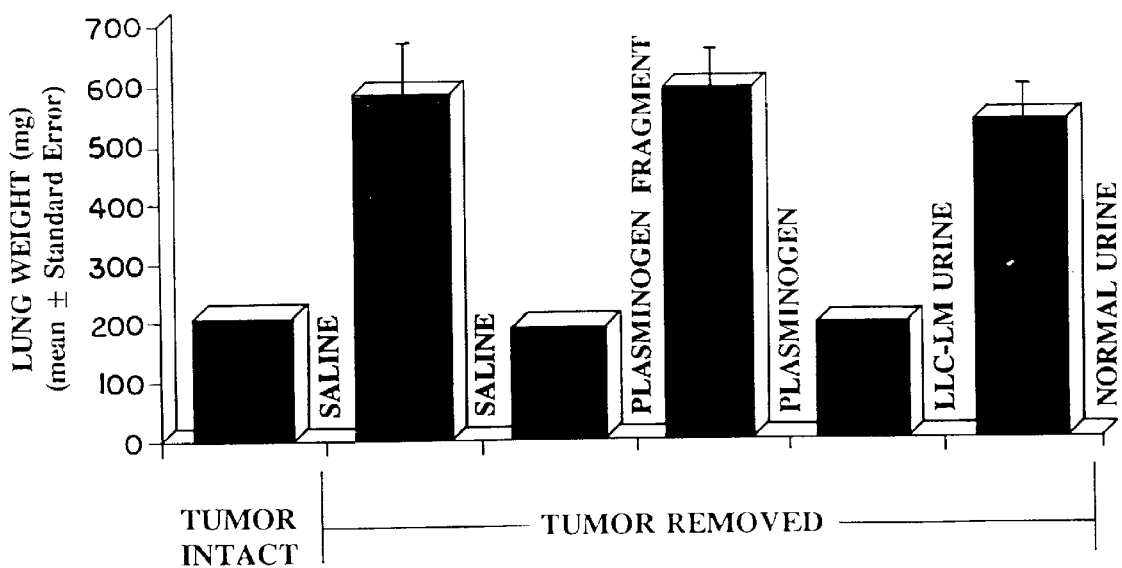
Fig_9

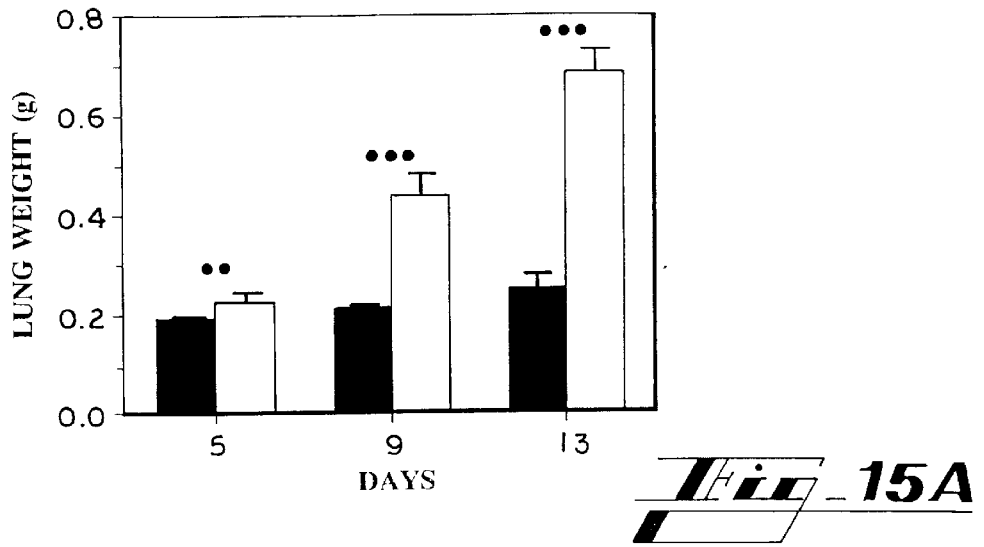
_Fig. 15A_
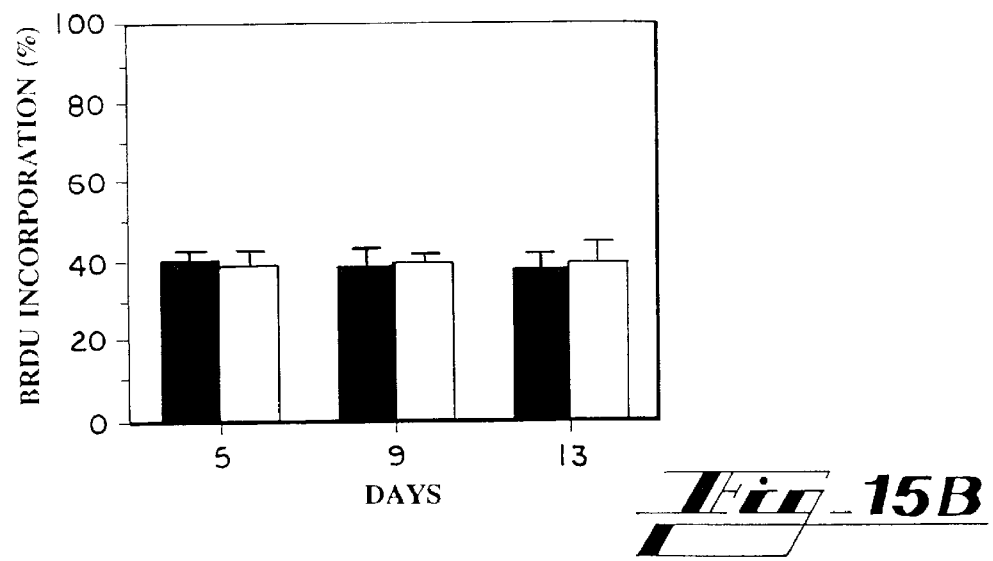
_Fig. 15B_
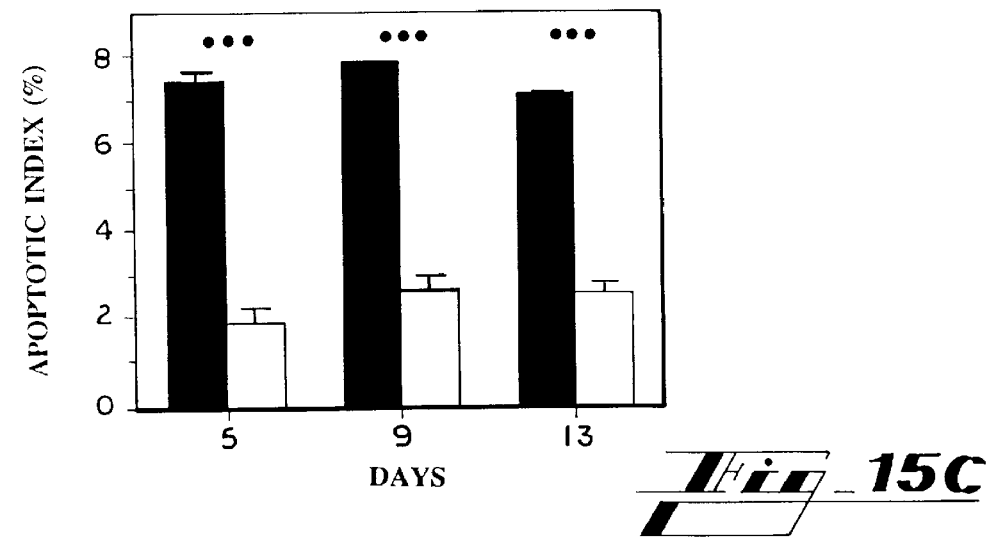
_Fig. 15C_

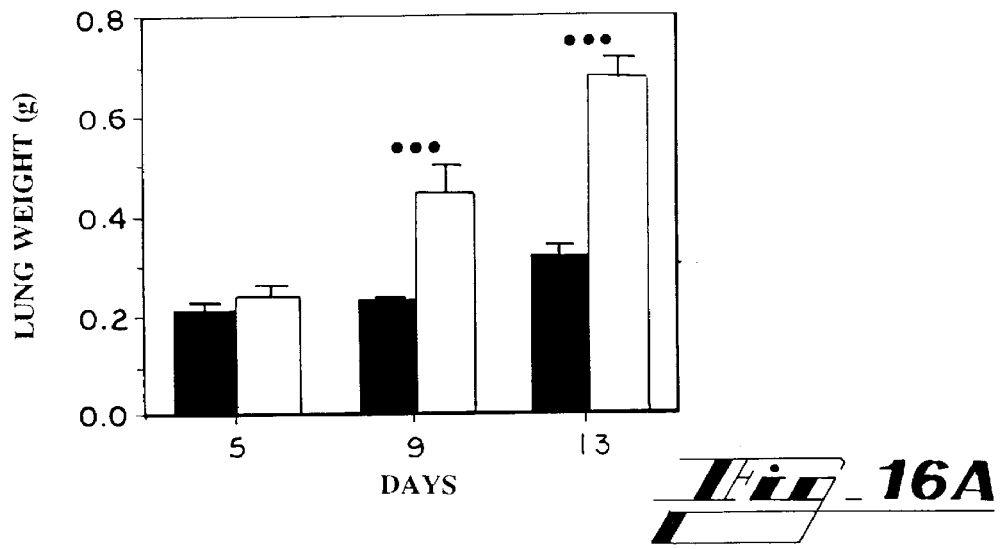
Fig_16A
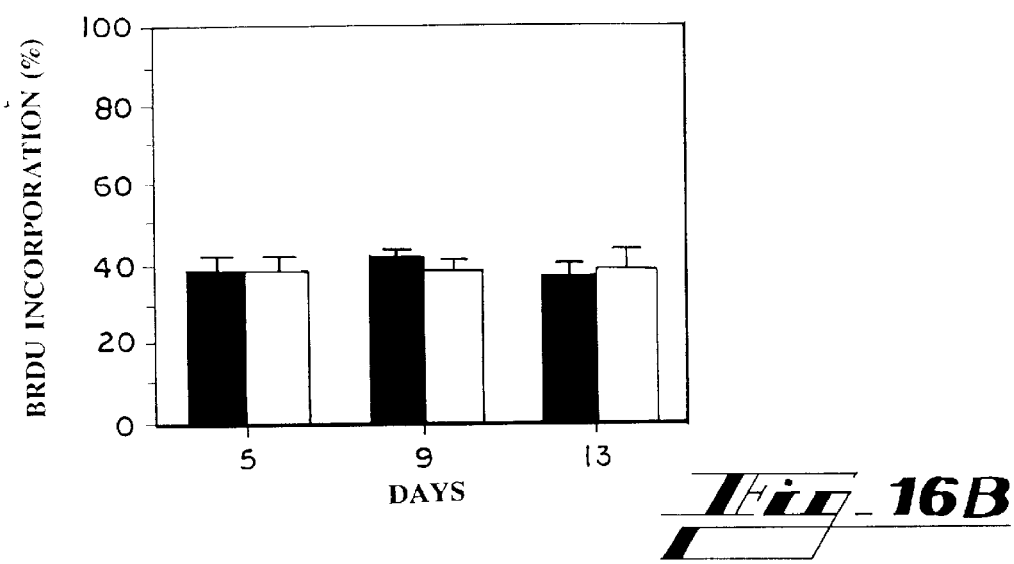
Fig_16B
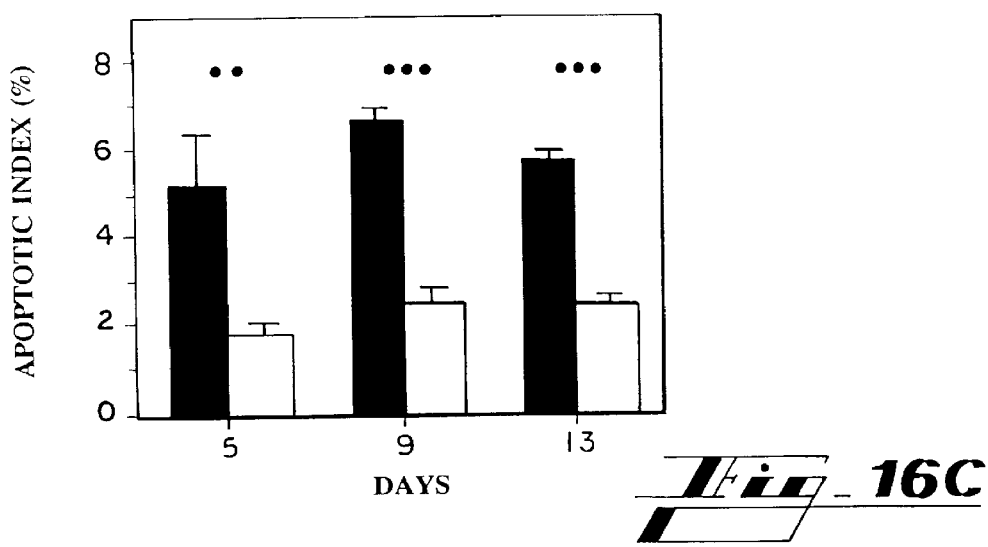
Fig_16C

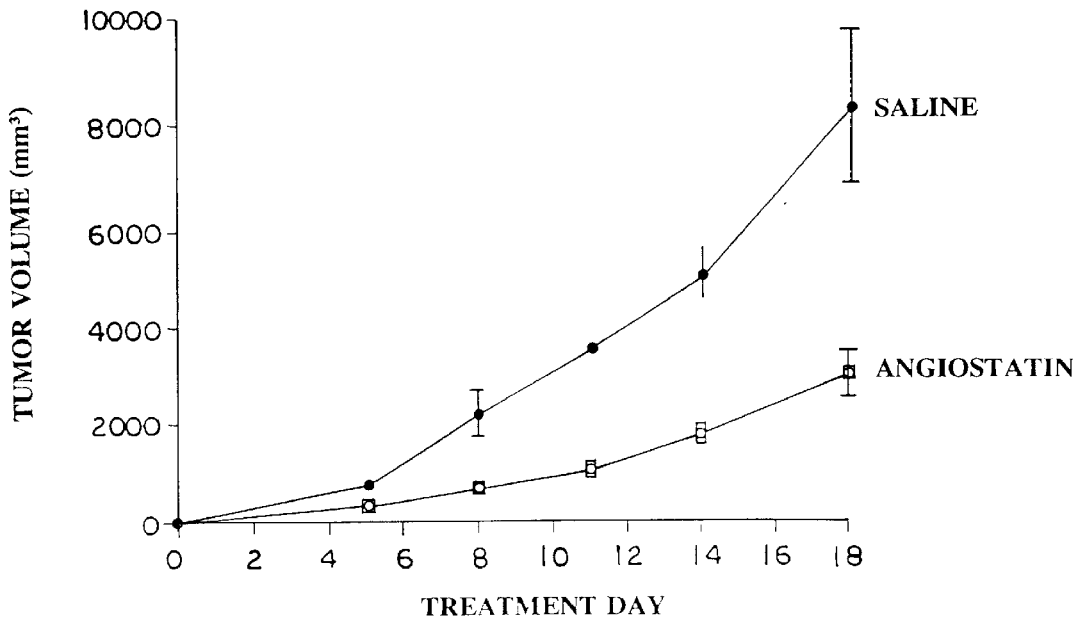
Fig_17
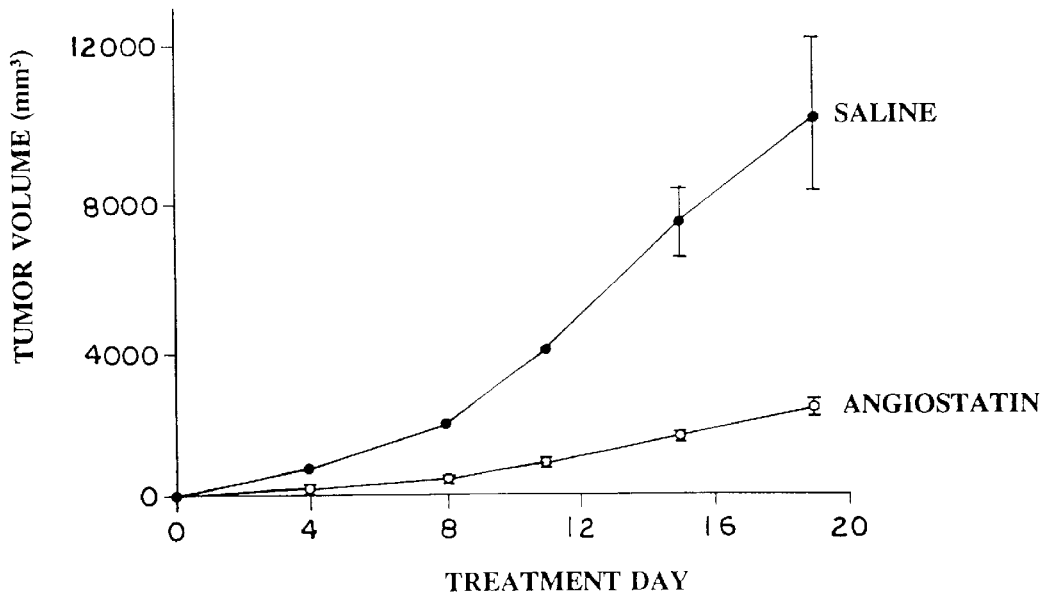
Fig_18

INHIBITION OF HUMAN PROSTATE CARCINOMA PC-3 BY ANGIOSTATIN IN SCID MICE

INHIBITION OF HUMAN BREAST CARCINOMA MDA-MB BY ANGIOSTATIN IN SCID MICE

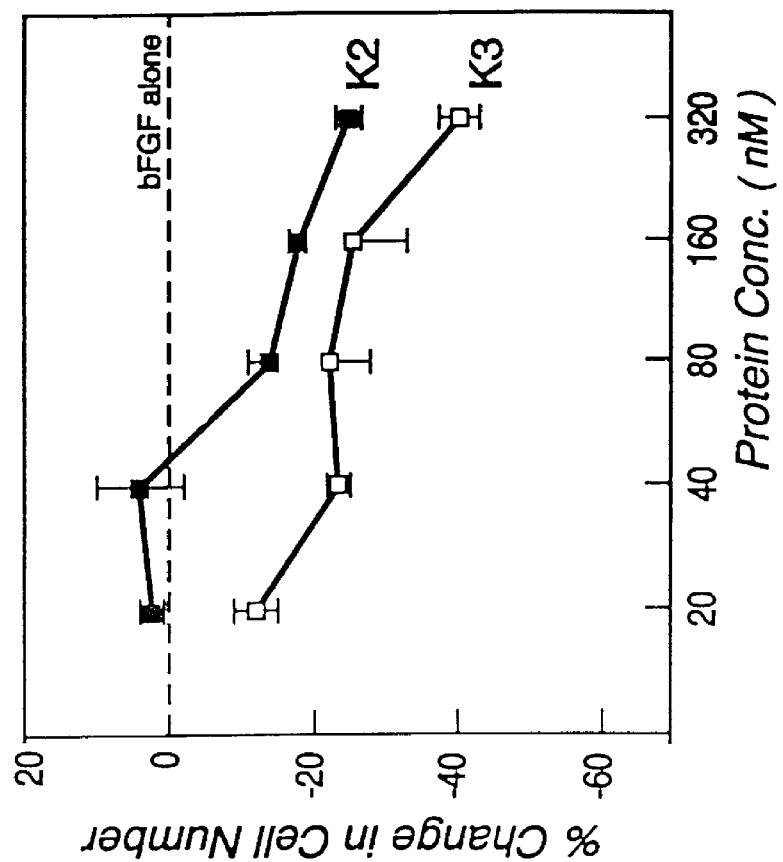
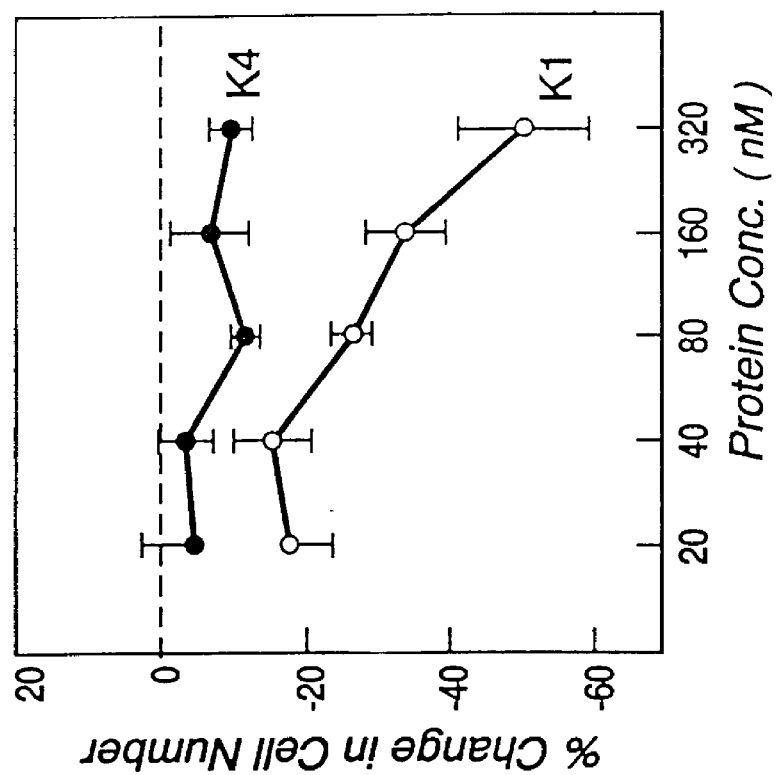
FIGURE 30A
FIGURE 30B

```
           *                                                                    *
Kringle1   CKTGNGKNYRGTMSKTKNGITCQKWSSTSPHRP-RFSPAT
Kringle2   CMHCSGENYDGKISKTMSGLECQAWDSQSPHAHG-YIPSK
Kringle3   CLKGTENYRGNVAVTVSGHTCQHWSAQTPHTHNR-TPEN
Kringle4   CYHGDGQSYRGTSSTTTGKKCQSWSSMTPHRHQK-TPEN

*                              *                         *
Kringle1   HPSEGLEENYCRNPDNDPQGPWCYTTDPEKRYDYCDILEC
Kringle2   FPNKLKKNYCRNPDREL-RPWCFTTDPNKRWELCDIPRC
Kringle3   FPCKNLDENYCRNPDGKR-APWCHTTNSQVRWEYCKIPSC
Kringle4   YPNAGLTMNYCRNPDADK-GPWCFTTDPSVRWEYCNLKKC
```

FIGURE 35

A
kD  1   2   3
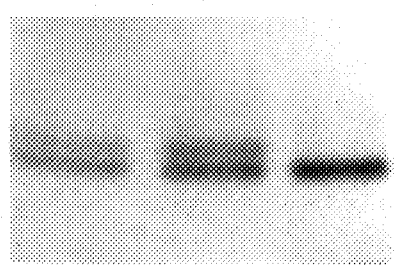
50–
B
1   2   3
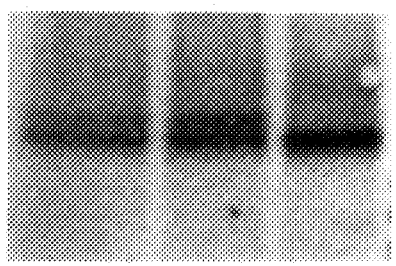
50–
FIG. 37

ANGIOSTATIN FRAGMENTS AND METHOD OF USE

FIELD OF THE INVENTION

The present invention relates to endothelial inhibitors, called angiostatin, which reversibly inhibit proliferation of endothelial cells. More particularly, the present invention relates to angiostatin proteins that can be isolated from body fluids such as blood or urine, or can be synthesized by recombinant, enzymatic or chemical methods. The angiostatin is capable of inhibiting angiogenesis related diseases and modulating angiogenic processes. In addition, the present invention relates to diagnostic assays and kits for angiostatin measurement, to histochemical kits for localization of angiostatin, to DNA sequences coding for angiostatin and molecular probes to monitor angiostatin biosynthesis, to antibodies that are specific for the angiostatin, to the development of protein agonists and antagonists to the angiostatin receptor, to anti-angiostatin receptor-specific antibody agonists and antagonists, and to cytotoxic agents linked to angiostatin proteins.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The hypothesis that tumor growth is angiogenesis-dependent was first proposed in 1971. (Folkman J., Tumor angiogenesis: Therapeutic implications., *N. Engl. Jour. Med.* 285:1182 1186, 1971) In its simplest terms it states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants. *J. Natl. Cancer Inst.* 6:73–85, 1945)

(2) Tumors grown in isolated perfused organs where blood vessels do not proliferate are limited to 1–2 $mm^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid and canine intestinal segments. *Annals of Surgery* 164:491–502, 1966)

(3) Tumor growth in the avascular cornea proceeds slowly and at a linear rate, but switches to exponential growth after neovascularization. (Gimbrone, M. A., Jr. et al., Tumor growth and neovascularization: An experimental model using the rabbit cornea. *J. Natl. Cancer Institute* 52:41–427, 1974)

(4) Tumors suspended in the aqueous fluid of the anterior chamber of the rabbit eye, remain viable, avascular and limited in size to <1 $mm^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization. *J. Exp. Med.* 136:261–276)

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton D., Avascular and vascular phases of tumor growth in the chick embryo. *British J. Cancer*, 35:347–356, 1977)

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340, 1970)

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman J, et al., Induction of angiogenesis during the transition from hyperplasia to neoplasia. *Nature* 339:58–61, 1989)

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993)

(9) Anti-bFGF monoclonal antibody causes 70% inhibition of growth of a mouse tumor which is dependent upon secretion of bFGF as its only mediator of angiogenesis. The antibody does not inhibit growth of the tumor cells *in vitro*. (Hori A, et al., Suppression of solid tumor growth by immunoneutralizing monoclonal antibody against human basic fibroblast growth factor. *Cancer Research*, 51:6180–6184, 1991)

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross J L, et al. Modulation of solid tumor growth in vivo by bFGF. *Proc. Amer. Assoc. Canc. Res.* 31:79, 1990)

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Angioinhibins: Synthetic analogues of fumagillin which inhibit angiogenesis and suppress tumor growth. *Nature*, 48:555–557, 1990). There is also indirect clinical evidence that tumor growth is angiogenesis dependent.

(12) Human retinoblastomas that are metastatic to the vitreous develop into avascular spheroids which are restricted to less than 1 $mm^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 $mm^3$). These implants rarely grow larger until one or more of them becomes neovascularized.

(14) Intensity of neovascularization in breast cancer (Weidner N, et al., Tumor angiogenesis correlates with metastasis in invasive breast carcinoma. *N. Engl. J. Med.* 324:1–8, 1991, and Weidner N, et al., Tumor angiogenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. *American Journal of Pathology*, 143(2):401–409, 1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.* 133:419–423, 1988)

(16) In bladder cancer, the urinary level of an angiogenic protein, bFGF, is a more sensitive indicator of status and extent of disease than is cytology. (Nguyen M, et al., Elevated levels of an angiogenic protein, basic fibroblast growth factor, in urine of bladder cancer patients. *J. Natl. Cancer Inst.* 85:241–242, 1993)

Thus, it is clear that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

What is needed therefore is a composition and method which can inhibit the unwanted growth of blood vessels, especially into tumors. Also needed is a method for detecting, measuring, and localizing the composition. The composition should be able to overcome the activity of endogenous growth factors in premetastatic tumors and prevent the formation of the capillaries in the tumors thereby inhibiting the growth of the tumors. The composition, fragments of the composition, and antibodies specific to the composition, should also be able to modulate the formation of capillaries in other angiogenic processes, such as wound healing and reproduction. The composition and method for inhibiting angiogenesis should preferably be non-toxic and produce few side effects. Also needed is a method for detecting, measuring, and localizing the binding sites for the composition as well as sites of biosynthesis of the composition. The composition and fragments of the composition should be capable of being conjugated to other molecules for both radioactive and non-radioactive labeling purposes

SUMMARY OF THE INVENTION

In accordance with the present invention, compositions and methods are provided that are effective for modulating angiogenesis, and inhibiting unwanted angiogenesis, especially angiogenesis related to tumor growth. The present invention includes a protein, which has been named "angiostatin", defined by its ability to overcome the angiogenic activity of endogenous growth factors such as bFGF, in vitro, and by it amino acid sequence homology and structural similarity to an internal portion of plasminogen beginning at approximately plasminogen amino acid 98. Angiostatin comprises a protein having a molecular weight of between approximately 38 kilodaltons and 45 kilodaltons as determined by reducing polyacrylamide gel electrophoresis and having an amino acid sequence substantially similar to that of a fragment of murine plasminogen beginning at amino acid number 98 of an intact murine plasminogen molecule (SEQ ID NO:2).

The amino acid sequence of angiostatin varies slightly between species. For example, in human angiostatin the amino acid sequence is substantially similar to the sequence of the above described murine plasminogen fragment, although an active human angiostatin sequence may start at either amino acid number 97 or 99 of an intact human plasminogen amino acid sequence. Further, fragments of human plasminogen has similar anti-angiogenic activity as shown in a mouse tumor model. It is to be understood that the number of amino acids in the active angiostatin molecule may vary and all amino acid sequences that have endothelial inhibiting activity are contemplated as being included in the present invention.

The present invention provides methods and compositions for treating diseases and processes mediated by undesired and uncontrolled angiogenesis by administering to a human or animal a composition comprising a substantially purified angiostatin or angiostatin derivative in a dosage sufficient to inhibit angiogenesis. The present invention is particularly useful for treating, or for repressing the growth of, tumors. Administration of angiostatin to a human or animal with prevascularized metastasized tumors will prevent the growth or expansion of those tumors.

The present invention also encompasses DNA sequences encoding angiostatin, expression vectors containing DNA sequences encoding angiostatin, and cells containing one or more expression vectors containing DNA sequences encoding angiostatin. The present invention further encompasses gene therapy methods whereby DNA sequences encoding angiostatin are introduced into a patient to modify in vivo angiostatin levels.

The present invention also includes diagnostic methods and kits for detection and measurement of angiostatin in biological fluids and tissues, and for localization of angiostatin in tissues and cells. The diagnostic method and kit can be in any configuration well known to those of ordinary skill in the art. The present invention also includes antibodies specific for the angiostatin molecule and portions thereof, and antibodies that inhibit the binding of antibodies specific for the angiostatin. These antibodies can be polyclonal antibodies or monoclonal antibodies. The antibodies specific for the angiostatin can be used in diagnostic kits to detect the presence and quantity of angiostatin which is diagnostic or prognostic for the occurrence or recurrence of cancer or other disease mediated by angiogenesis. Antibodies specific for angiostatin may also be administered to a human or animal to passively immunize the human or animal against angiostatin, thereby reducing angiogenic inhibition.

The present invention also includes diagnostic methods and kits for detecting the presence and quantity of antibodies that bind angiostatin in body fluids. The diagnostic method and kit can be in any configuration well known to those of ordinary skill in the art.

The present invention also includes anti-angiostatin receptor-specific antibodies that bind to the angiostatin receptor and transmit the appropriate signal to the cell and act as agonists or antagonists.

The present invention also includes angiostatin protein fragments and analogs that can be labeled isotopically or with other molecules or proteins for use in the detection and visualization of angiostatin binding sites with techniques, including, but not limited to, positron emission tomography, autoradiography, flow cytometry, radioreceptor binding assays, and immunohistochemistry.

These angiostatin proteins and analogs also act as agonists and antagonists at the angiostatin receptor, thereby enhancing or blocking the biological activity of angiostatin. Such proteins are used in the isolation of the angiostatin receptor.

The present invention also includes angiostatin, angiostatin fragments, angiostatin antisera, or angiostatin receptor agonists and angiostatin receptor antagonists linked to cytotoxic agents for therapeutic and research applications. Still further, angiostatin, angiostatin fragments, angiostatin antisera, angiostatin receptor agonists and angiostatin receptor antagonists are combined with pharmaceutically acceptable excipients, and optionally sustained-release compounds or compositions, such as biodegradable polymers, to form therapeutic compositions.

The present invention includes molecular probes for the ribonucleic acid and deoxyribonucleic acid involved in transcription and translation of angiostatin. These molecular probes provide means to detect and measure angiostatin biosynthesis in tissues and cells.

Accordingly, it is an object of the present invention to provide a composition comprising an angiostatin.

It is another object of the present invention to provide a method of treating diseases and processes that are mediated by angiogenesis.

It is yet another object of the present invention to provide a diagnostic or prognostic method and kit for detecting the presence and amount of angiostatin in a body fluid or tissue.

It is yet another object of the present invention to provide a method and composition for treating diseases and processes that are mediated by angiogenesis including, but not limited to, hemangioma, solid tumors, blood borne tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

It is another object of the present invention to provide a composition for treating or repressing the growth of a cancer.

It is an object of the present invention to provide compounds that modulate or mimic the production or activity of enzymes that produce angiostatin in vivo or in vitro.

It is a further object of the present invention to provide angiostatin or anti-angiostatin antibodies by direct injection of angiostatin DNA into a human or animal needing such angiostatin or anti-angiostatin antibodies.

It is an object of present invention to provide a method for detecting and quantifying the presence of an antibody specific for an angiostatin in a body fluid.

Still another object of the present invention is to provide a composition consisting of antibodies to angiostatin that are selective for specific regions of the angiostatin molecule that do not recognize plasminogen.

It is another object of the present invention to provide a method for the detection or prognosis of cancer.

It is another object of the present invention to provide a composition for use in visualizing and quantitating sites of angiostatin binding in vivo and in vitro.

It is yet another object of the present invention to provide a composition for use in detection and quantification of angiostatin biosynthesis.

It is yet another object of the present invention to provide a therapy for cancer that has minimal side effects.

Still another object of the present invention is to provide a composition comprising angiostatin or an angiostatin protein linked to a cytotoxic agent for treating or repressing the growth of a cancer.

Another object of the present invention is to provide a method for targeted delivery of angiostatin-related compositions to specific locations.

Yet another object of the invention is to provide compositions and methods useful for gene therapy for the modulation of angiogenic processes.

These and other objects, features and advantages of the present invention will become apparent after a review of the following detailed description of the disclosed embodiments and the appended claims.

BRIEF DESCRIPTION OF THE FIGURES

FIG. 1 shows SEQ ID NO: 1, the amino acid sequence of the whole murine plasminogen.

FIG. 2 shows the beginning sequence of the angiostatin for murine (SEQ ID NO:2) and compares the murine sequence with corresponding human (SEQ ID NO:3), Rhesus monkey (SEQ ID NO:4), porcine (SEQ ID NO:5) and bovine (SEQ ID NO:6) plasminogen protein fragments.

The mouse sequence is listed first, followed by human, Rhesus, porcine and bovine.

Figure 3A:
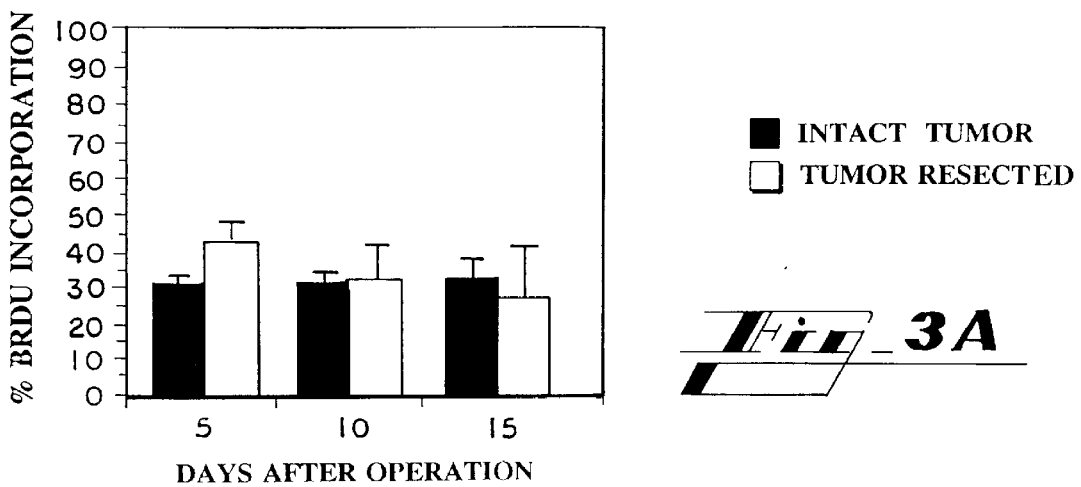
Figure 3B:
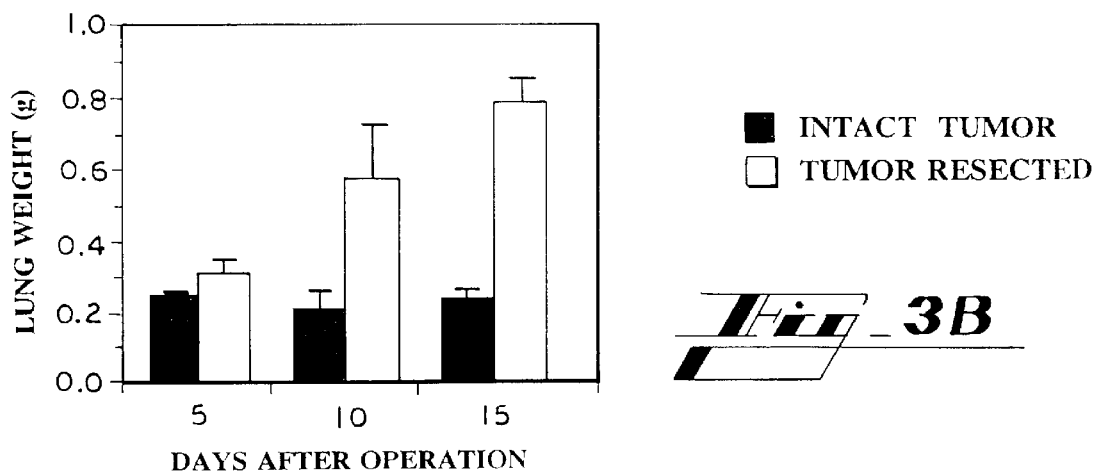

FIG. 3 shows BrdU labeling index of tumor cells in the lung in the presence or absence of a primary tumor.

Figure 4:
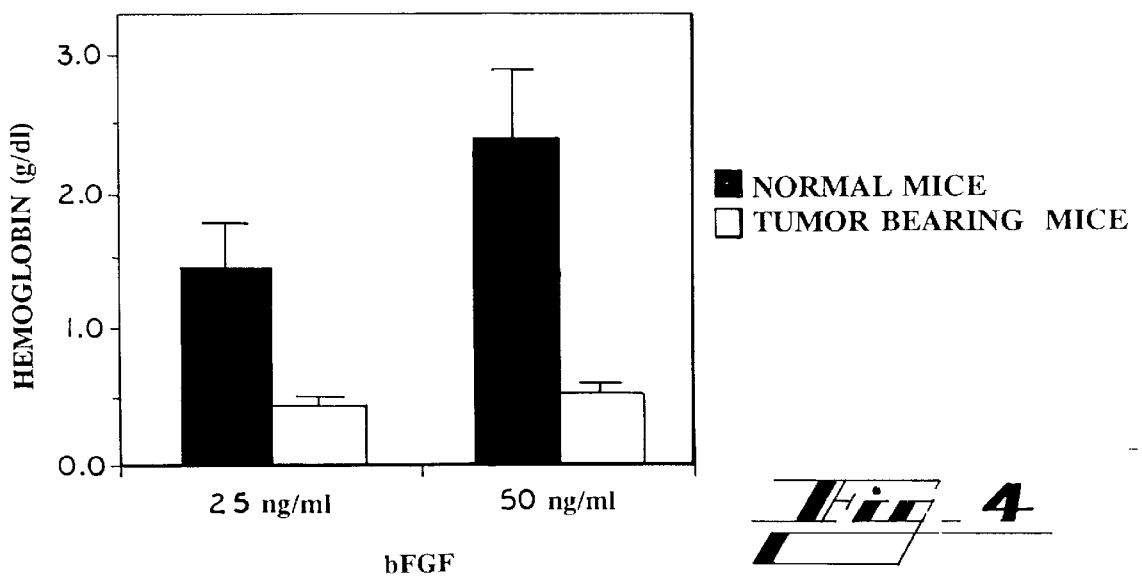

FIG. 4 shows Matrigel analysis of the influence of a Lewis lung primary tumor on bFGF driven angiogenesis in vivo.

FIG. 5 shows dose response curve for serum derived from mice bearing Lewis lung carcinoma (LLC-Low) versus serum from normal mice. Bovine capillary endothelial cells were assayed in a bFGF-driven 72-hour proliferation assay.

FIG. 6 shows that both low and high metastatic tumors contain endothelial mitogenic activity in their ascites, but only the low metastatic tumor line has endothelial inhibitory activity in the serum.

Figures 7A, 7B:
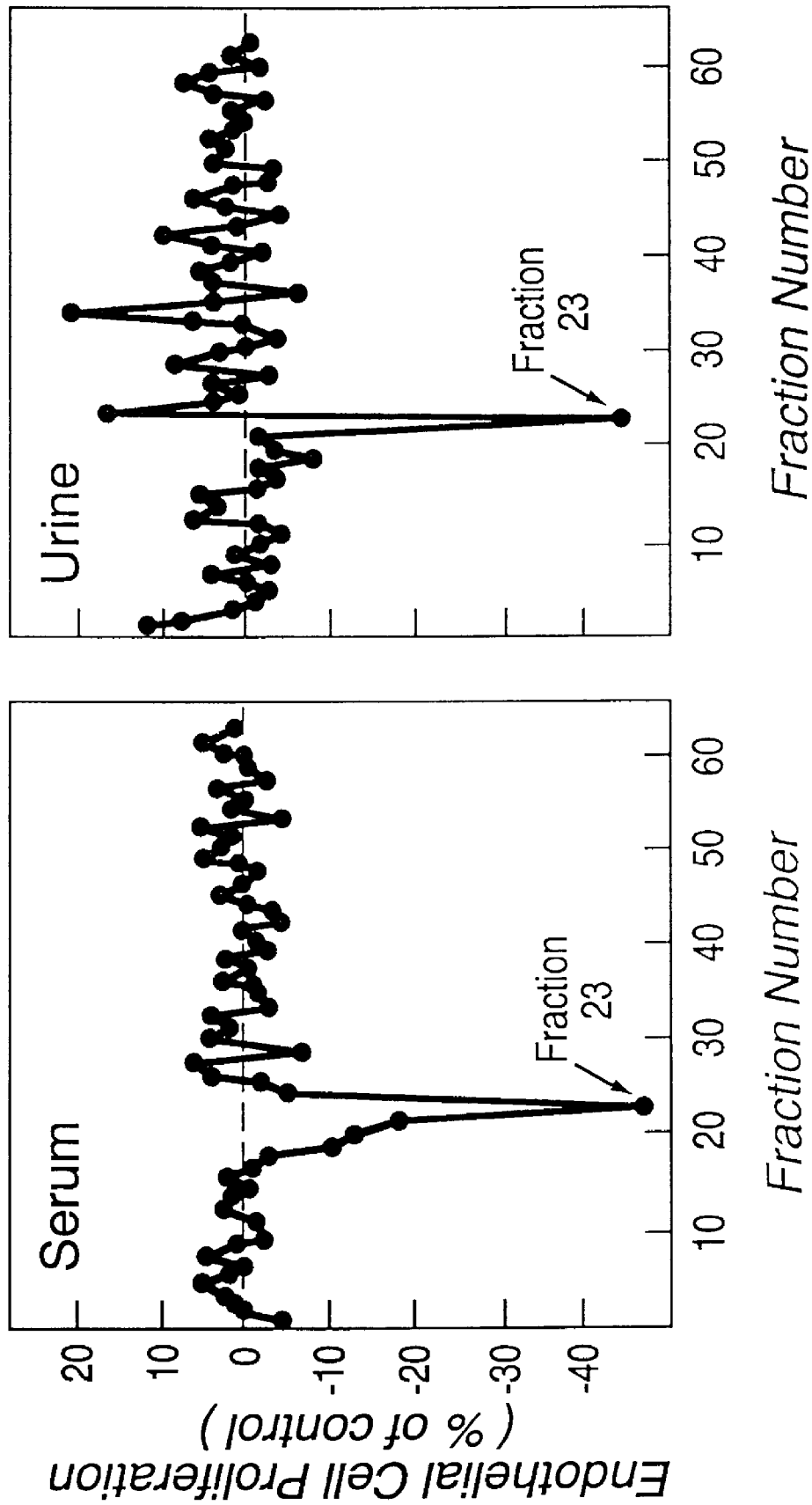

FIG. 7 shows a C4 Reverse Phase Chromatographic profile of partially purified serum or urine from tumor-bearing animals.

FIG. 8 shows surface lung metastases after the 13 day treatment of mice with intact plasminogen molecule, active fraction from a lysine binding site I preparation of human plasminogen, concentrated urine from tumor bearing mice and concentrated urine from normal mice.

FIG. 9 shows lung weight after the 13 day treatment of mice with intact plasminogen molecule of human plasminogen, active fraction from lysine binding site I preparation, concentrated urine from tumor bearing mice and concentrated urine from normal mice.

Figure 10:
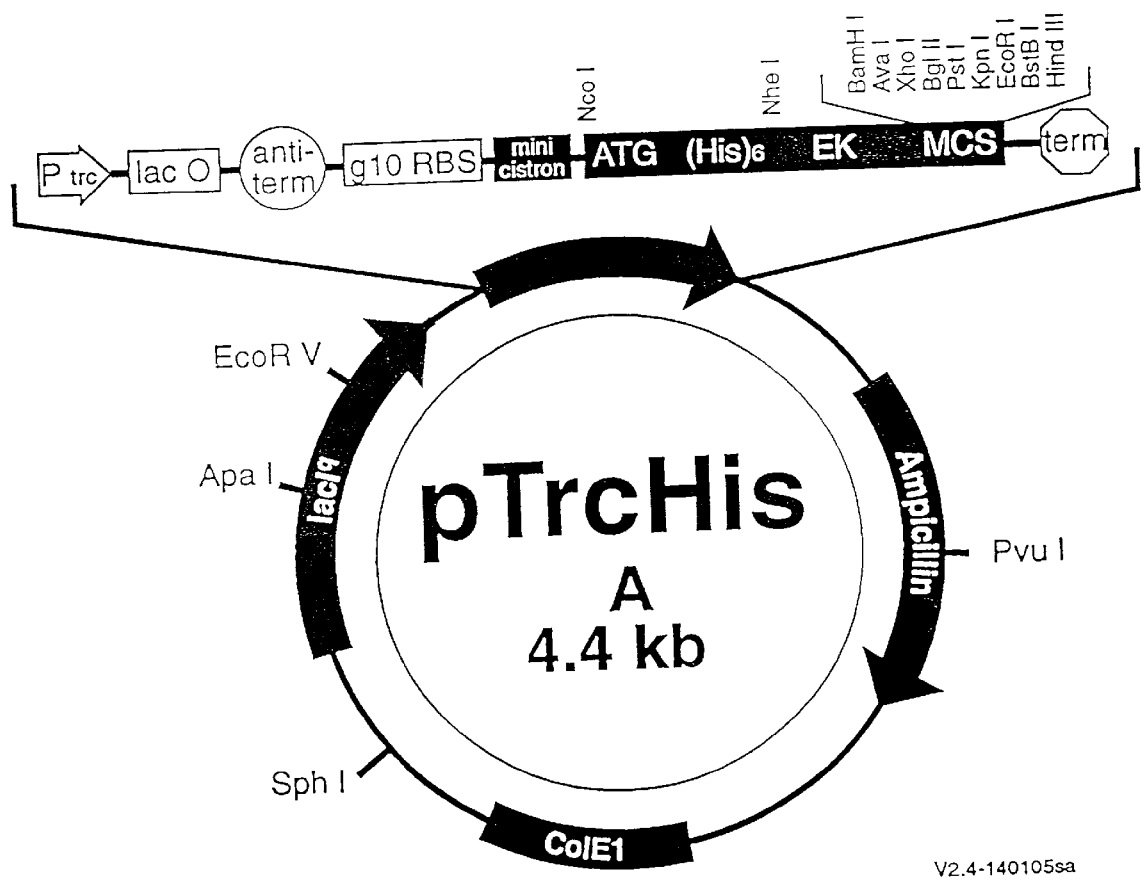

FIG. 10 is a schematic representation of the pTrcHis vector.

Figure 11:
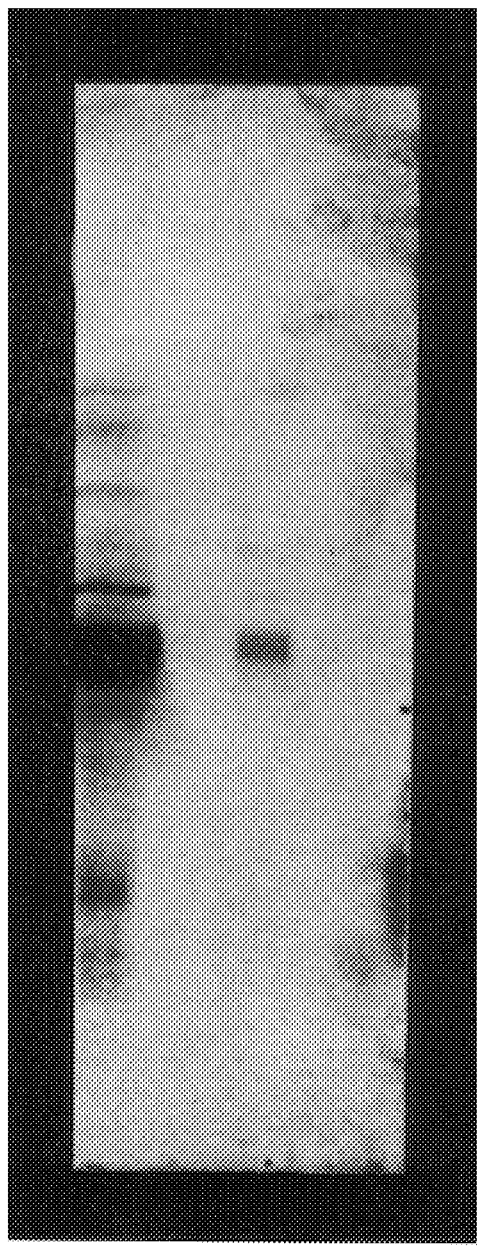

FIG. 11 depicts an immunoblot of *E.coli* expressed human angiostatin from a 10 L scaled-up fermentation, probed with monoclonal antibody against human plasminogen kringle region 1–3. Arrow shows recombinant human angiostatin. A) shows recombinant angiostatin eluted with 0.2M amino caproic acid; B) shows the last wash with 1×PBS of the lysine column; and C) shows clarified lysate from cracked cells.

Figure 12:
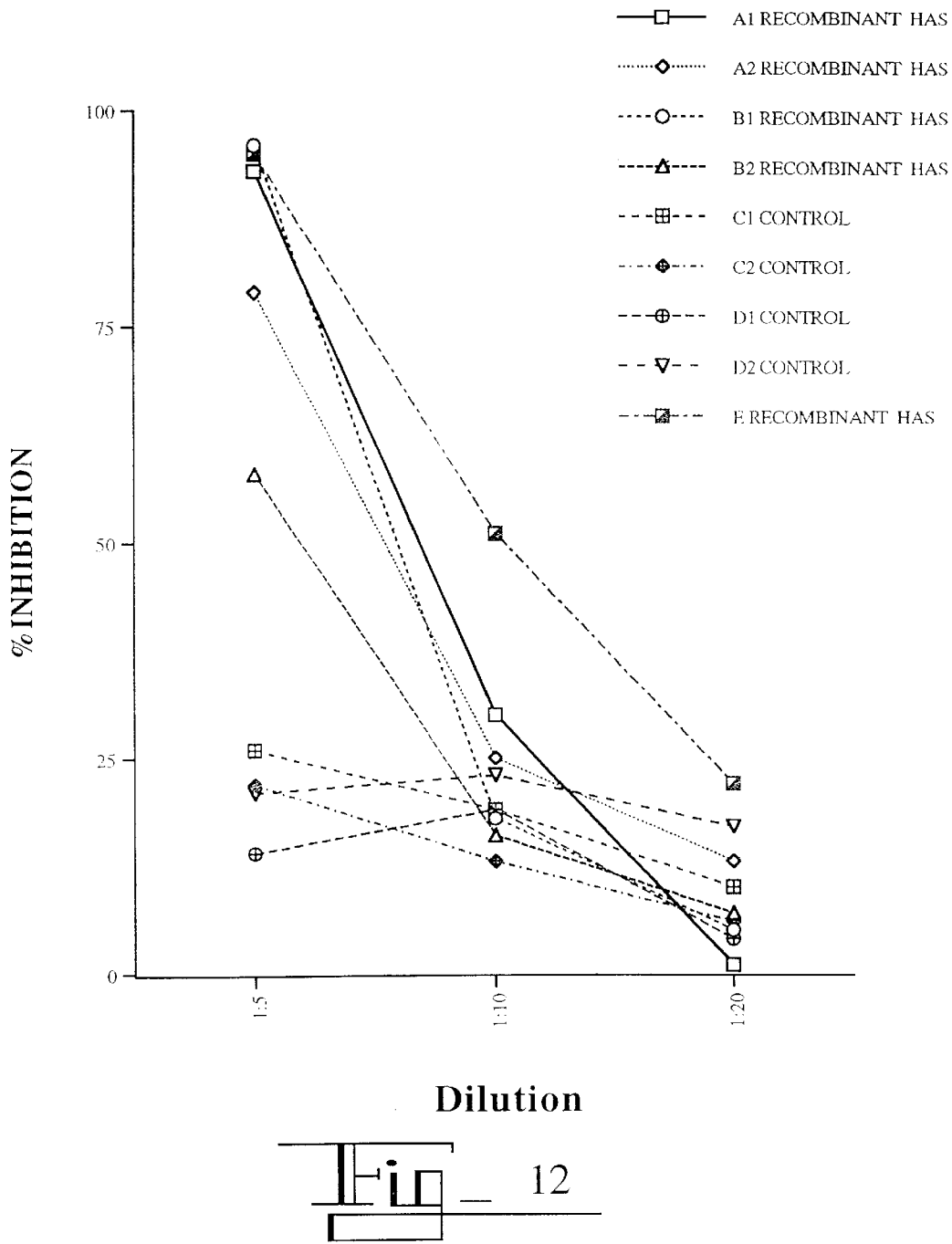

FIG. 12. Is a graph depicting percent inhibition of growing bovine capillary endothelial cells as a function of dilution of stock; A1, A2, B1, B2, and E are recombinant clones that express human angiostatin anit-angiogenesis activity; C1, C2, D1 and D2 controls are negative controls clones containing vector only without the human DNA sequence coding for angiostatin.

Figure 13:
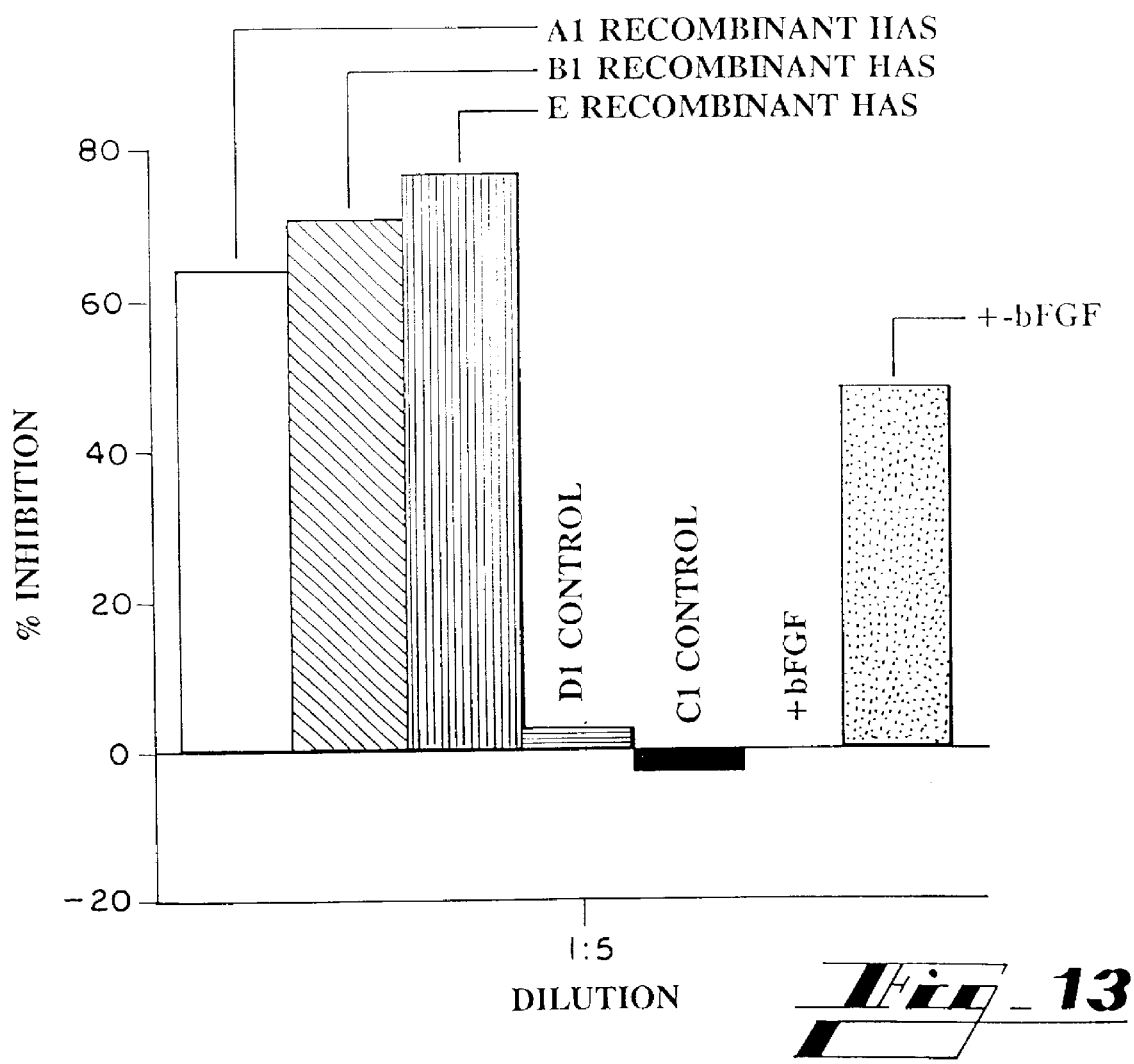

FIG. 13 shows the inhibitory effect on proliferation of recombinant human angiostatin on bovine capillary endothelial cells in vitro.

Figure 14:
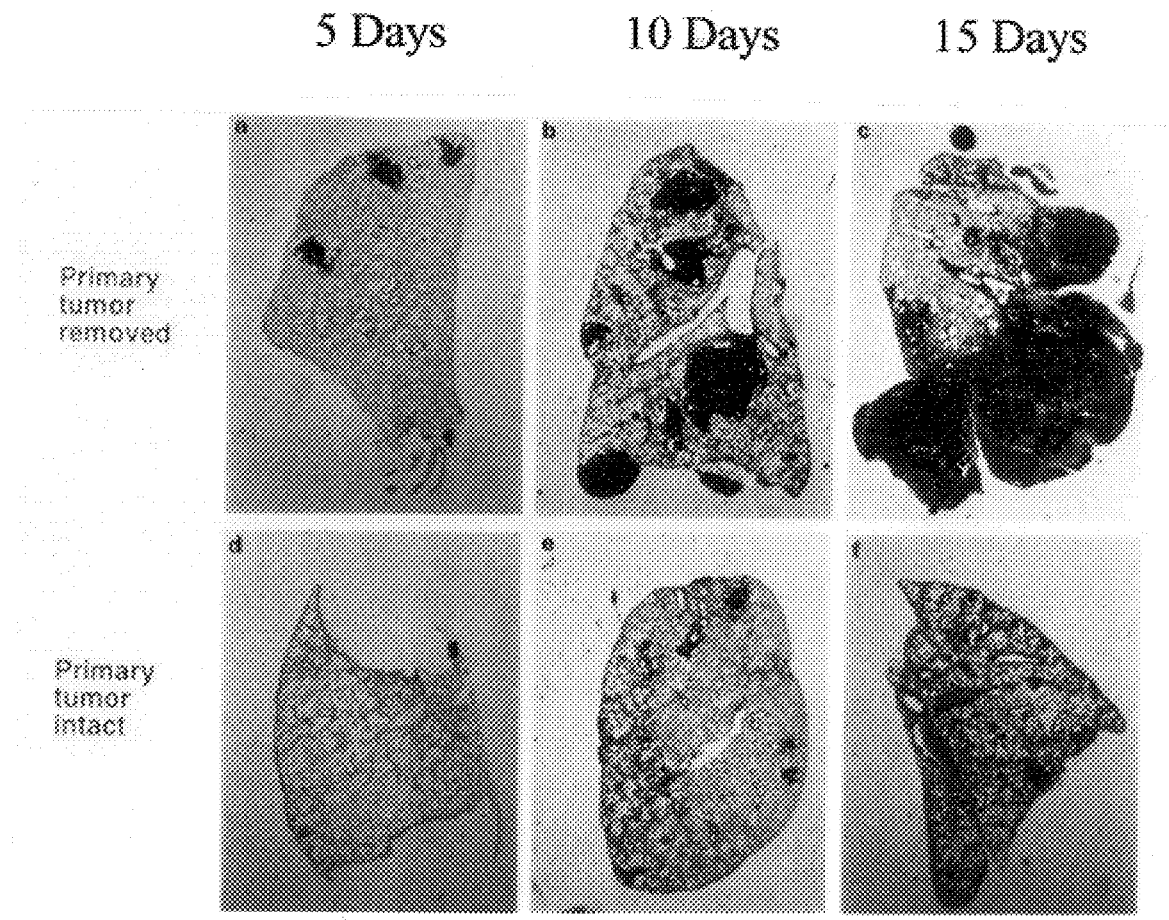

FIG. 14 shows the growth proliferation index and apoptotic index after removal of the primary tumor and treatment with saline or a fumagillin analogue with anti-angiogenic activity FIGS. 15A–C show the inhibition of growth of a T241 primary tumor in mice by treatment with human angiostatin in vivo with a single injection of 40 mg/kg/day.

FIGS. 16A–C show the inhibition of growth of a LLC-LM primary tumor in mice by treatment with human angiostatin in vivo at two doses of 40 mg/kg per dose (80 mg/kg/day).

FIG. 17 shows the effect of the removal of a Lewis lung carcinoma primary tumor on the growth of its lung metastases.

Figure 19:
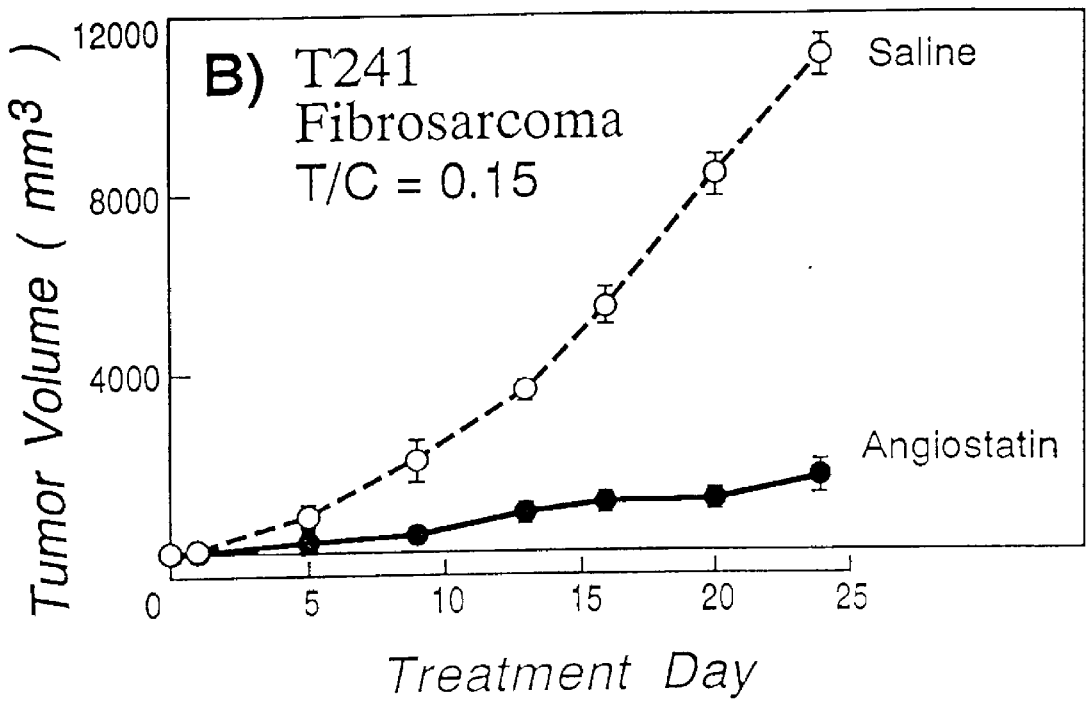

FIG. 18 shows the growth proliferation and apoptotic index after tumor resection FIG. 19 shows the effect of administration of angiostatin protein to mice having implated T241 fibrosarcoma cells on total tumor volume as a function of time.

Figure 20:
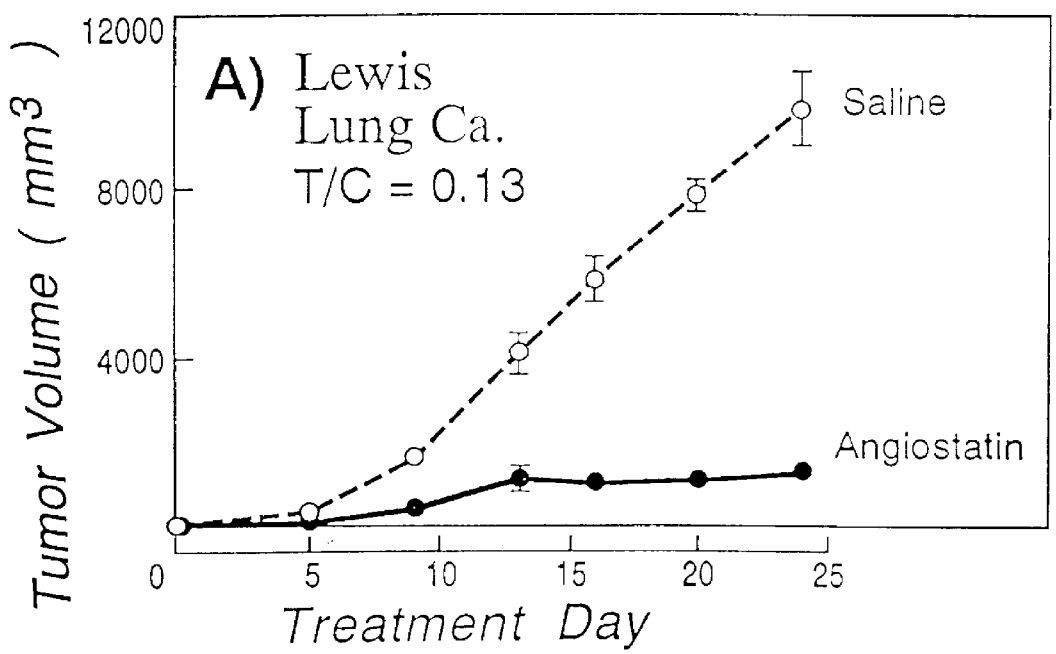

FIG. 20 shows the effect of administration of angiostatin protein to mice having implated Lewis lung carcinoma (LM) cells on total tumor volume as a function of time.

Figure 21:
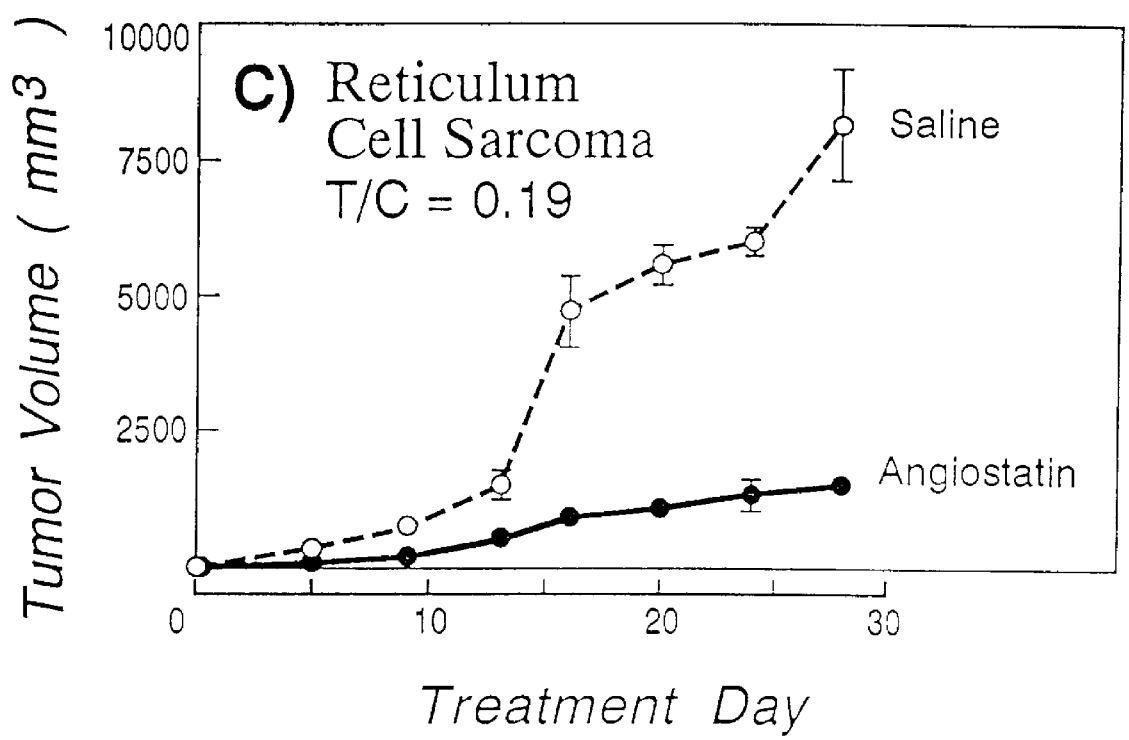

FIG. 21 shows the effect of administration of angiostatin protein to mice having implated reticulum cell sarcoma cells on total tumor volume as a function of time.

Figure 22:
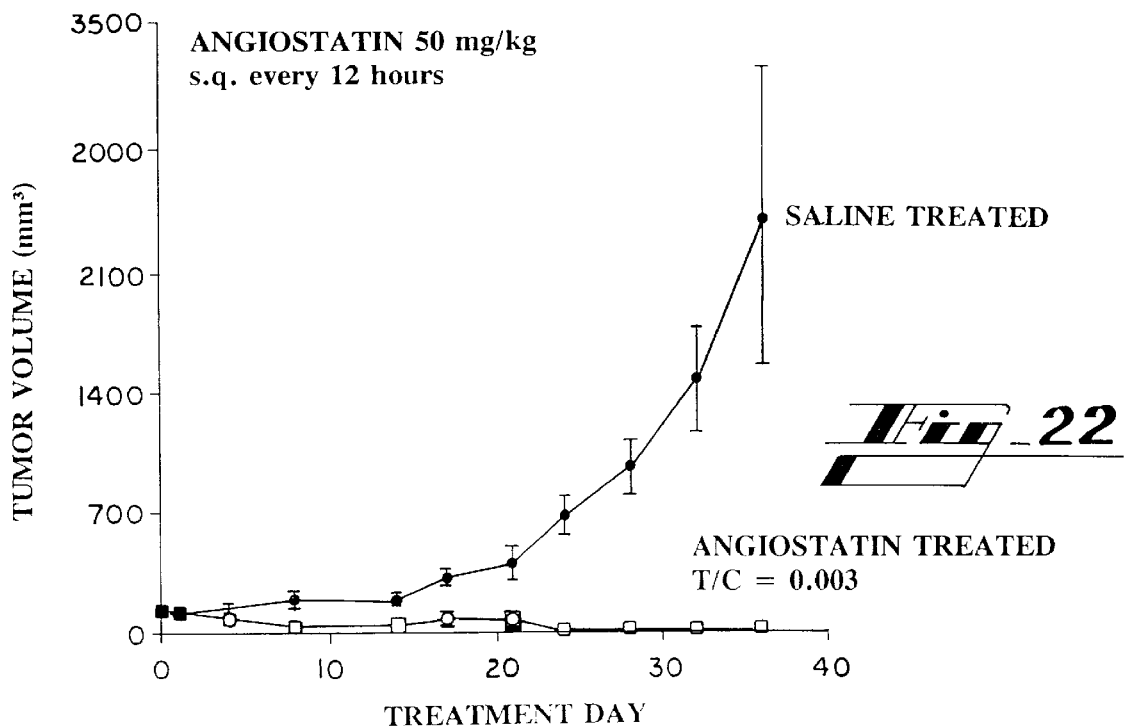

FIG. 22 shows the effect of administration of angiostatin protein to immunodeficient SCID mice having implated human prostate carcinoma PC-3 cells on total tumor volume as a function of time over a 24 day period.

Figure 23:
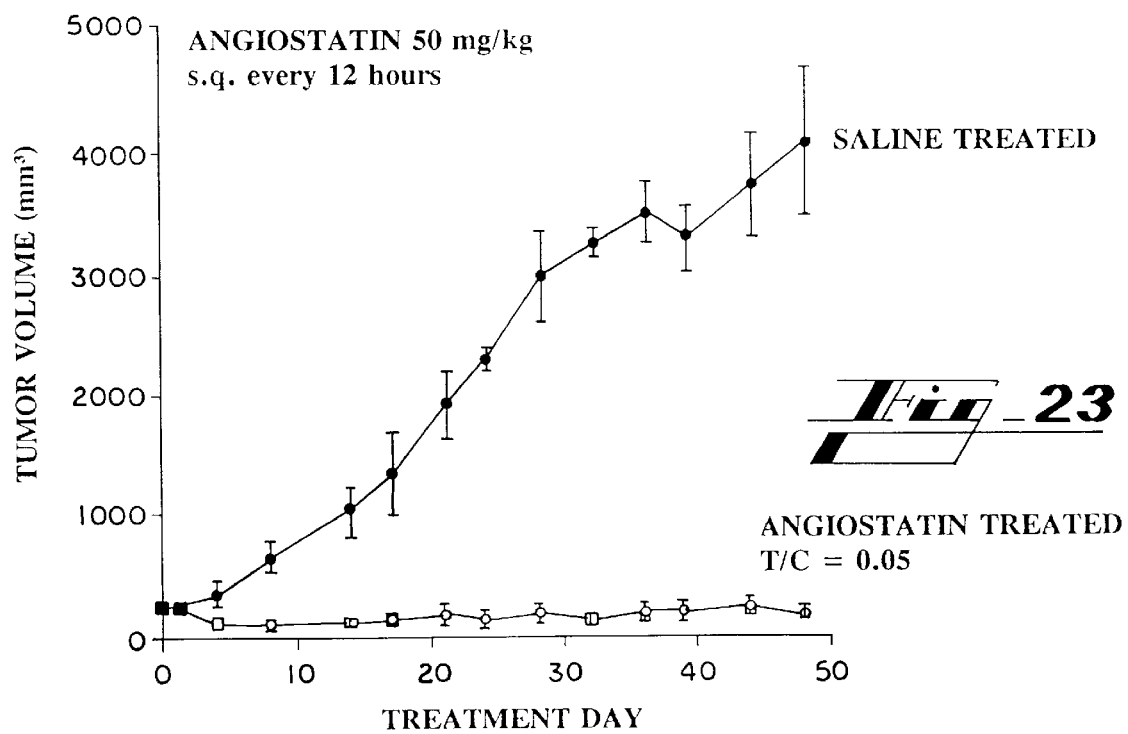

FIG. 23 shows the effect of administration of angiostatin protein to immunodeficient SCID mice having implated human breast carcinoma MDA-MB cells on total tumor volume as a function of time over a 24 day period.

Figure 24:
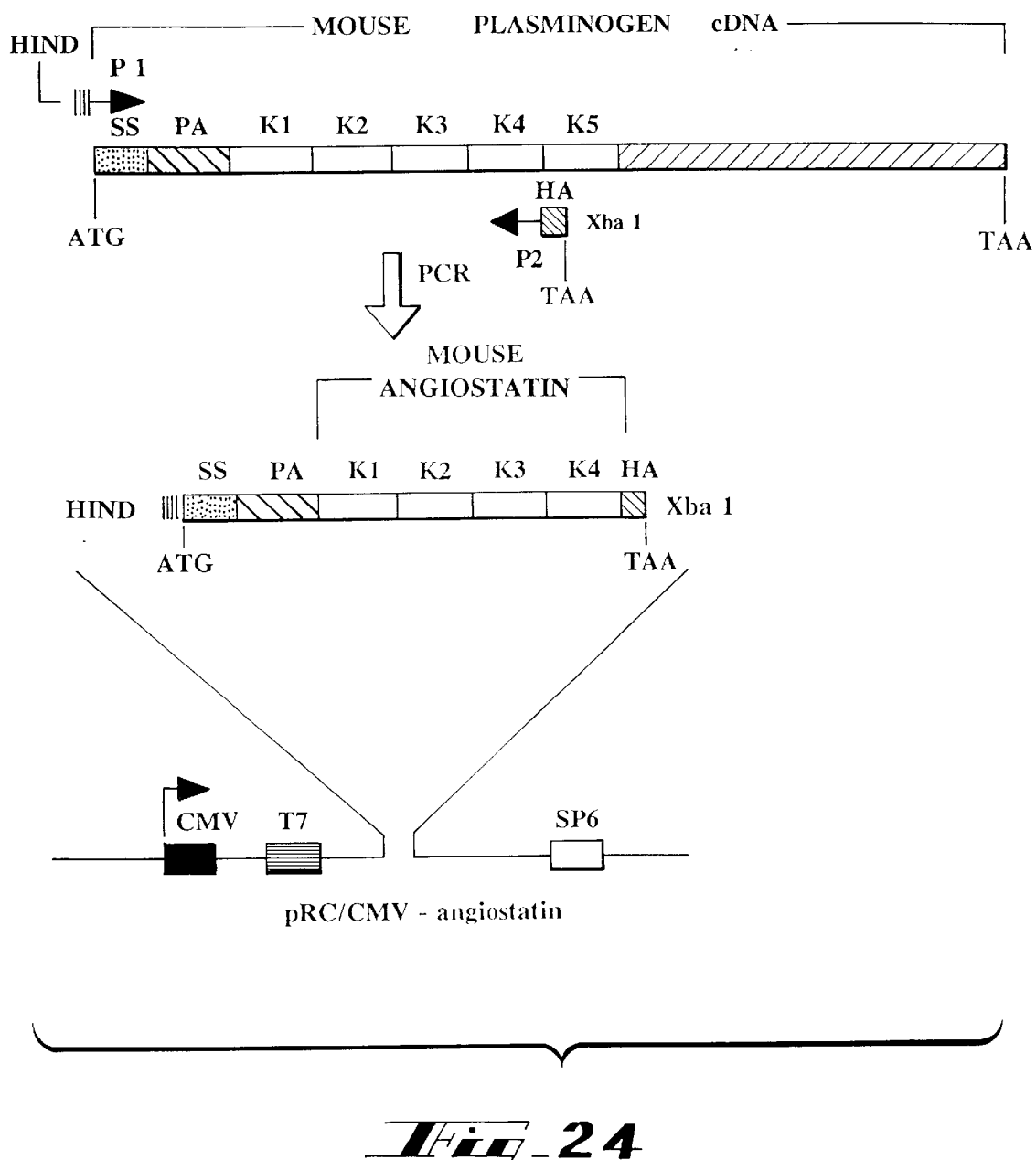

FIG. 24 is a schematic representation of cloning of the mouse DNA sequence coding for mouse angiostatin protein derived from mouse plasminogen cDNA. The mouse angiostatin encompasses mouse plasminogen kringle regions 1–4. PCR means polymerase chain reaction; P1 is the 5'-end oligonucleotide primre for PCR; P2 is the 3'-end oligonucleotide primre for PCR; SS designates the signal sequence; ATG is the translation initiation codon; TAA is the translation stop codon; HA represents the hemagglutinin epitope tag (YPYDVPDYASL); K1, K2, K3 and K4 represent mouse plasminogen kringle regions 1, 2, 3 and 4 respectively. CMV is the cytomegalovirus promoter; T7 is the bacteria phage promoter; PA represents pre-activation proteins; and SP6 is the Sp 6 promoter.

Figure 25A:
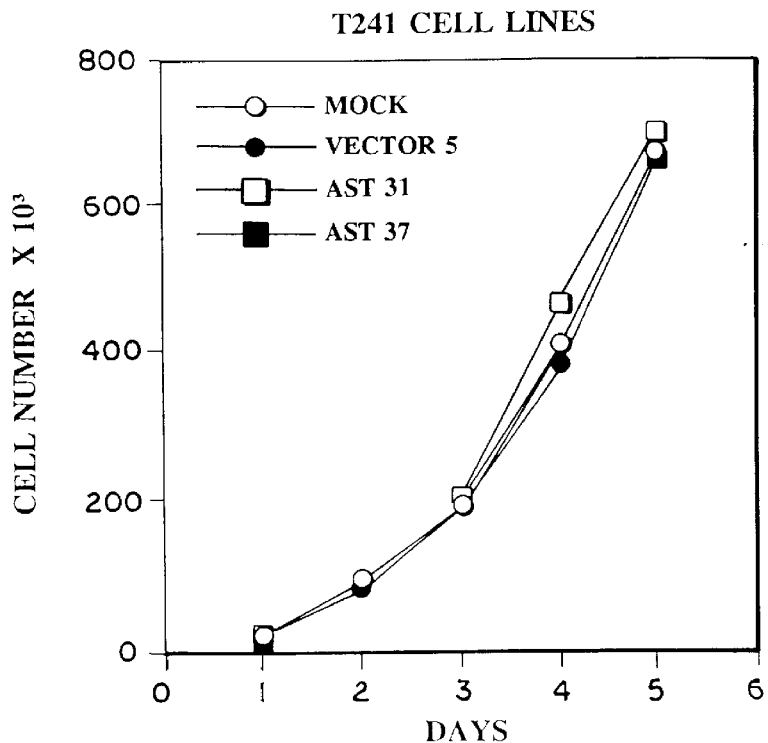
Figure 25B:
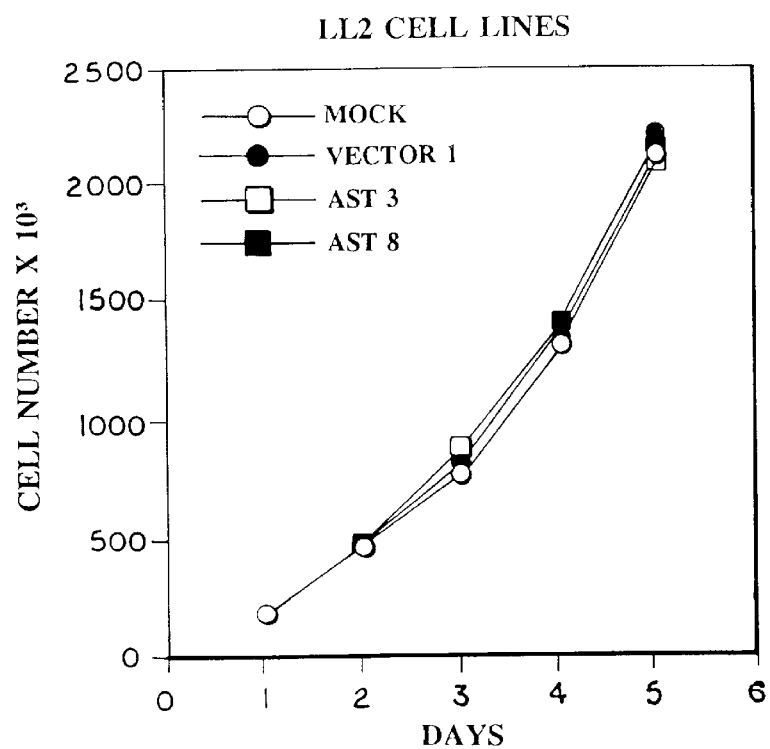

FIGS. 25A–B depict the number of cells as a function of days for non-transfected cells (mock); cells transfected with the vector alone, without the DNA sequence coding for angiostatin (Vector 5), and two angiostatin expressing clones (AST 31 and AST 37). Panel (a) represents the results of transfection of T241 cells. Panel (b) represents the results of LL2 cells.

Figure 26A:
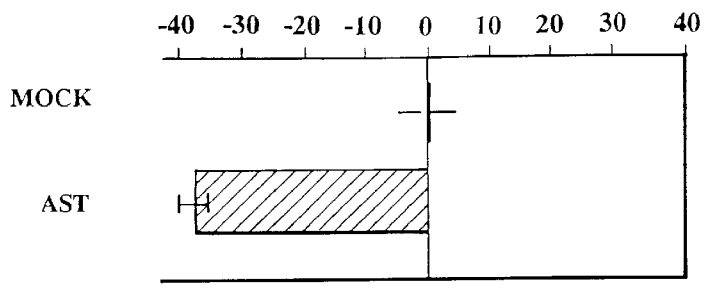
Figure 26B:
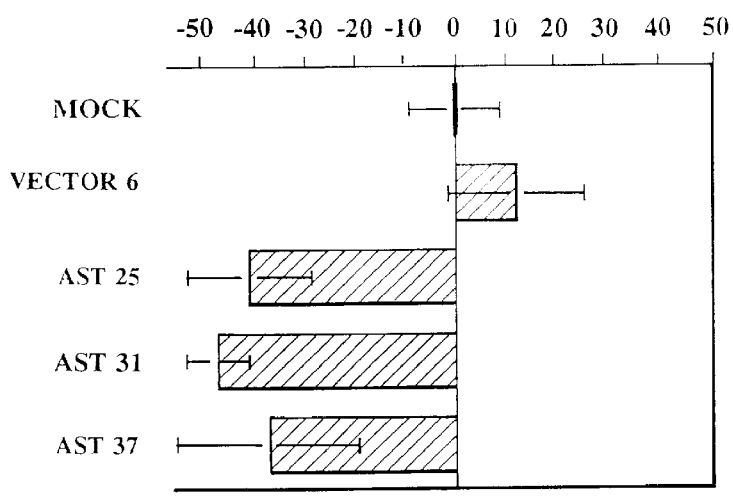
Figure 26C:
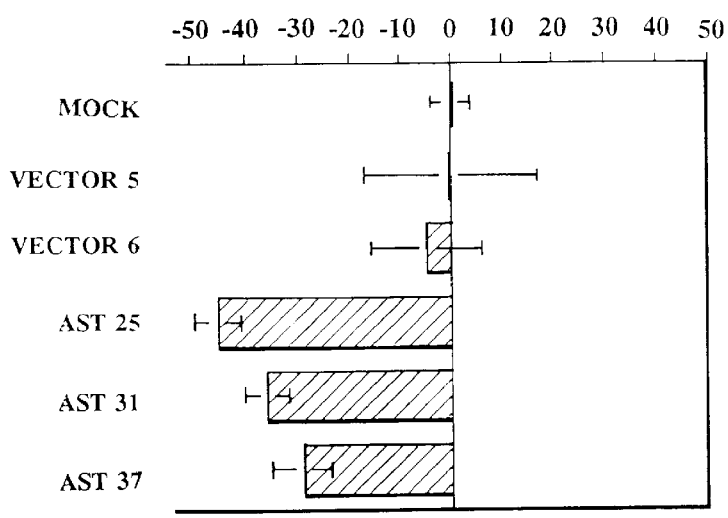

FIGS. 26A–C show the results of culture medium derived from *E. coli* cells containing the angiostatin clone on cell number. Non-transfected cells (mock); cells transfected with the vector alone, without the DNA sequence coding for angiostatin (Vector 5), and three angiostatin expressing clones (AST 25, AST 31 and AST 37). Panel (a) represents the results of incubation of culture medium from control (mock) and all angiostatin clones (expressing and non-expressing) on cell number. Panel (b) represents the results of incubation of culture medium from control (mock), vector alone (vector 6) and angiostatin clones expressing mouse angiostatin on cell number. Panel (c) represents the results of incubation of purified culture medium from control (mock) and angiostatin clones expressing mouse angiostatin on cell number, wherein the culture medium was purified over a lysine-sepharose colume to yield lysine binding components.

Figure 27:
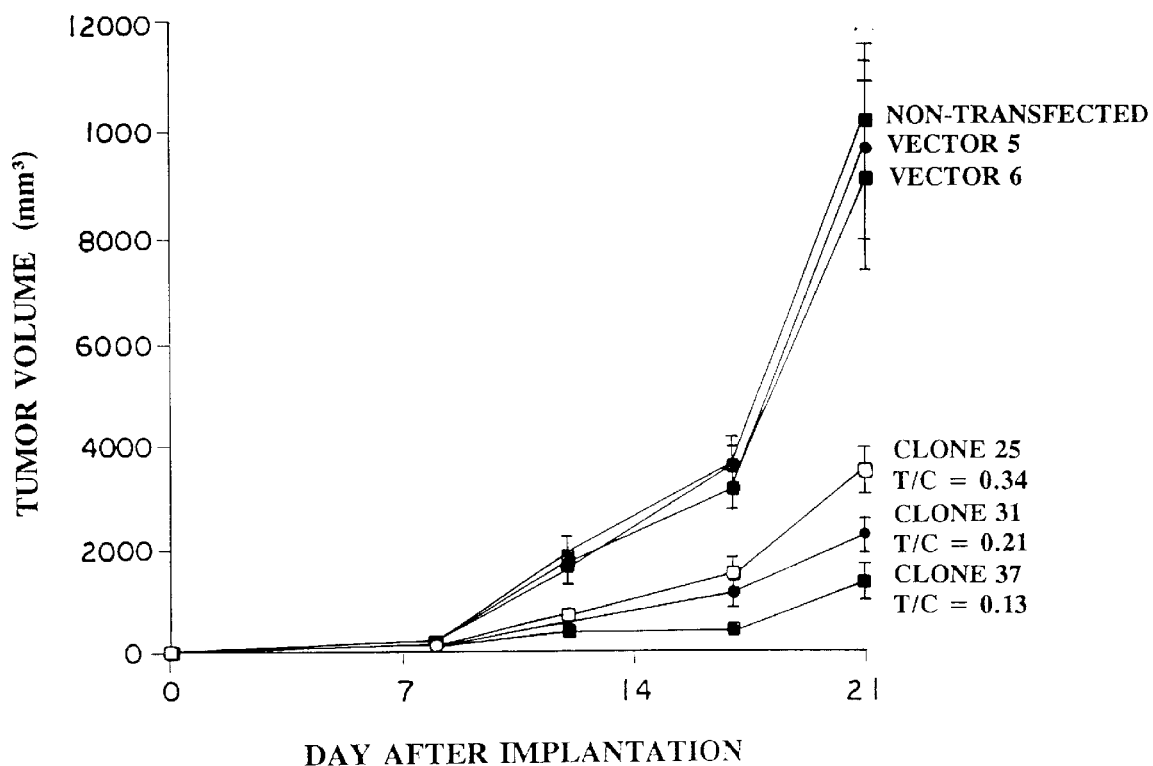

FIG. 27 shows the effect on total tumor volume as a function of time of implanting T241 fibrosarcoma cells in mice, where the fibrosarcoma cells have been transfected with a vector containing a DNA sequence coding for angiostatin protein, and where the vector is capable of expressing angiostatin protein. "Non-transfected" represents unaltered T241 fibrosarcoma cells implanted in mice. "Vector 6" represents T241 fibrosarcoma cells transfected with the vector only, which does not contain the DNA sequence coding for angiostatin protein, implanted in mice. "Clone 25, Clone 31 and Clone 37" represent three angiostatin-producing clones of T241 fibrosarcoma cells transfected with a vector containing the DNA sequence coding for angiostation protein implanted in mice.

Figure 28:
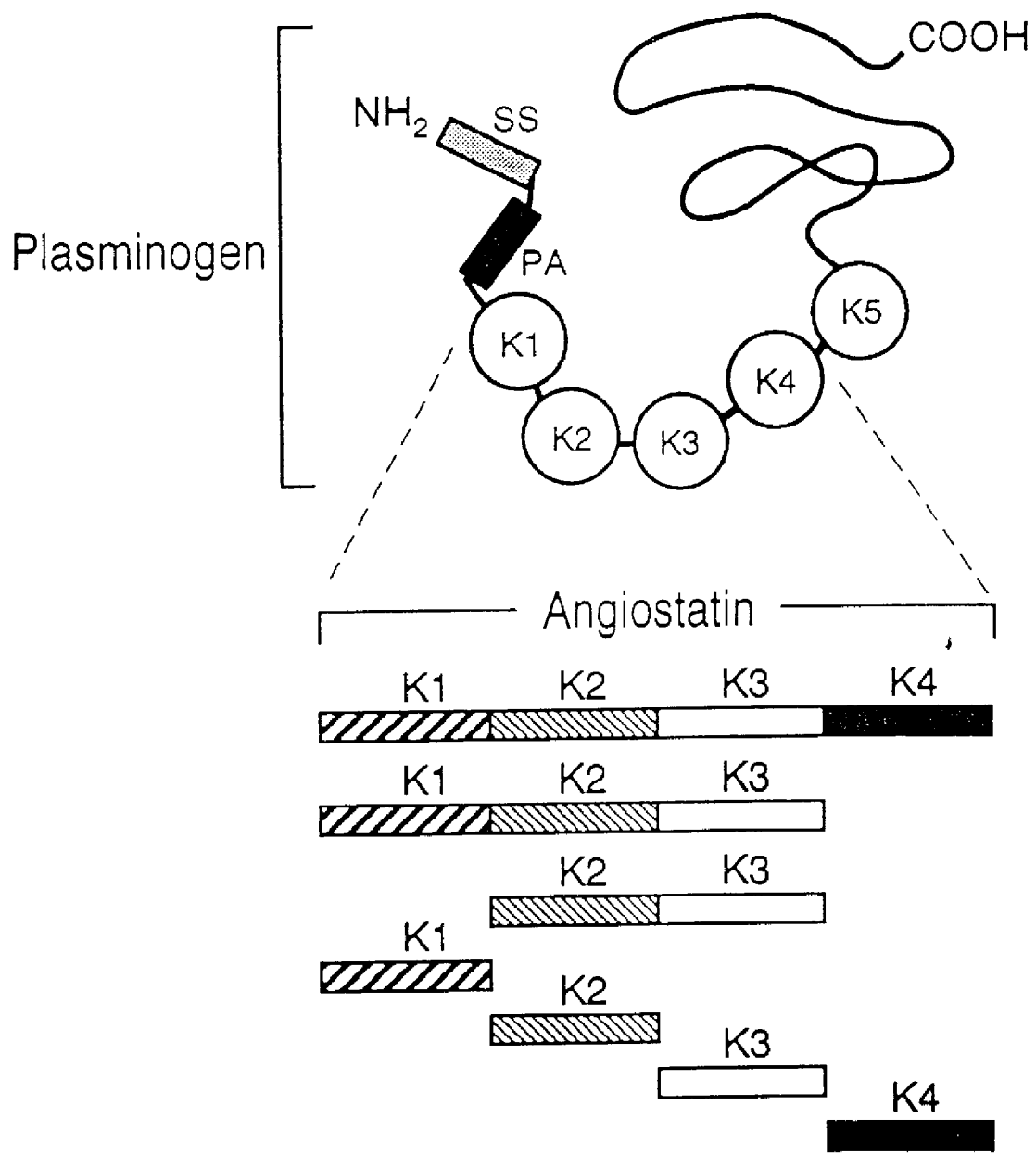

FIG. 28 shows a schematic representation of the structure of human plasminogen and its kringle fragments. Human plaminogen is a single chain protein containing 791 amino acids with one side of N-linked glycosylation at $Asn^{289}$. The non-protease region of human plasminogen consisting of the N-terminal 561 amino acids existing in five separate domains, termed kringles as shown in circles (K1, K2, K3, K4 and K5), along with proteins that separate these structures. Each triple disulfide bonded kringle contains 80 amino acids. Angiostatin covers the first 4 of these kringle domains (K1–4), kringle 3 (K1–3) and kringle 4 (K4) are obtained by digestion of human plasminogen with elastase. The rest of the kringle fragments are recombinant proteins expressed in *E. coli*. SS=signal sequence. PA=preactivation protein.

FIGS. 29A–B show a SDS-PAGE analysis of purified recombinant and native kringle fragments of plasminogen under reducing conditions. (A) Individual recombinant kringle fragments purified from *E. coli* bacterial lysates were loaded onto a 15% SDS gel followed by staining with Coomassie blue. Approximately 5 µg of each protein was loaded per lane. (lane 2=kringle 1 (K1); lane 3=kringle 2 (K2); lane 4=kringle 3 (K3); lane 5=kringle 4 (K4); lane 1=molecular weight markers). (B) Purified large kringle fragments were stained with Coomassie blue. Kringles 1–4 (lane 2) and kringles 1–3 (lane 3) were obtained by digestion of human plasminogen with elastase and purified by lysine-Sepharose chromatography. Recombinant fragment of kringles 2–3 (lane 4) was expressed in *E. coli* and re-folded in vitro. Molecular weight markers are indicated on the left (lane 1).

FIGS. 30A–B show an inhibition of endothelial cell proliferation by recombinant individual kringle fragments of angiostatin. Kringle fragments were assayed on bovine capillary endothelial cells in the presence of 1 ng/ml bFGF for 72 hours. (A) Anti-endothelial cell proliferative effects of two lysine-binding kringles, rK1 and rK4. The high-affinity lysine binding kringle, KI (-o-), inhibited BCE cell proliferation in a dose-dependent manner. The intermediate-affinity affinity lysine binding kringle, K4 (-●-), showed only little inhibitory effect at high concentrations. (B) Inhibition of BCE cell proliferation by non-lysine binding K2 and K3. Both K2 (-■-) and K3 (-□-) inhibited BCE cell proliferation in a dose-dependent manner. Data represents the mean +/–SEM of triplicates.

Figure 31:
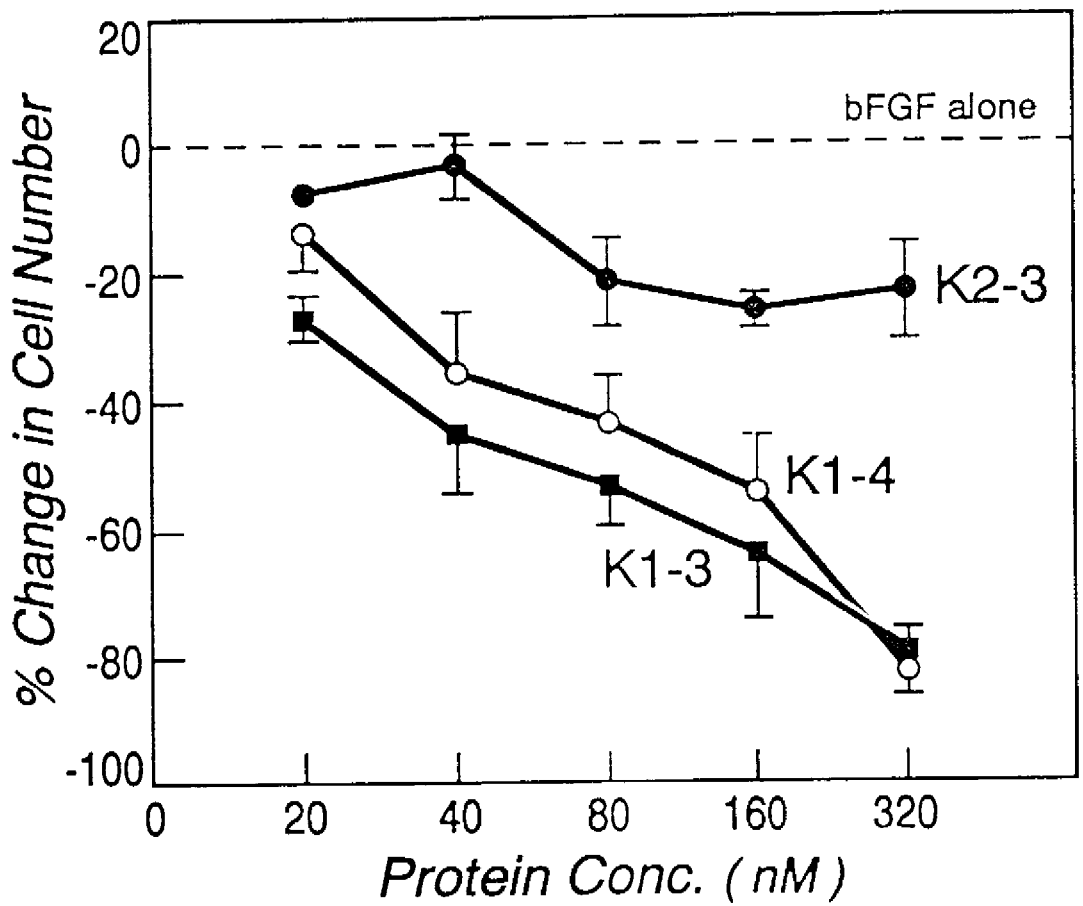

FIG. 31 shows an anti-endothelial proliferation activity of large kringle fragments of angiostatin. Proteolytic fragments, K1–4 (angiostatin) (-o-) and K1–3 (-■-), inhibited BCE cell proliferation in a dose-dependent manner. Recombinant K2–3 (-●-) fragments exhibited a less potent inhibition than those of K1–3 and K1–4. Data represents the mean of three determinations (+/– SEM) as percentages of inhibition.

Figure 32:
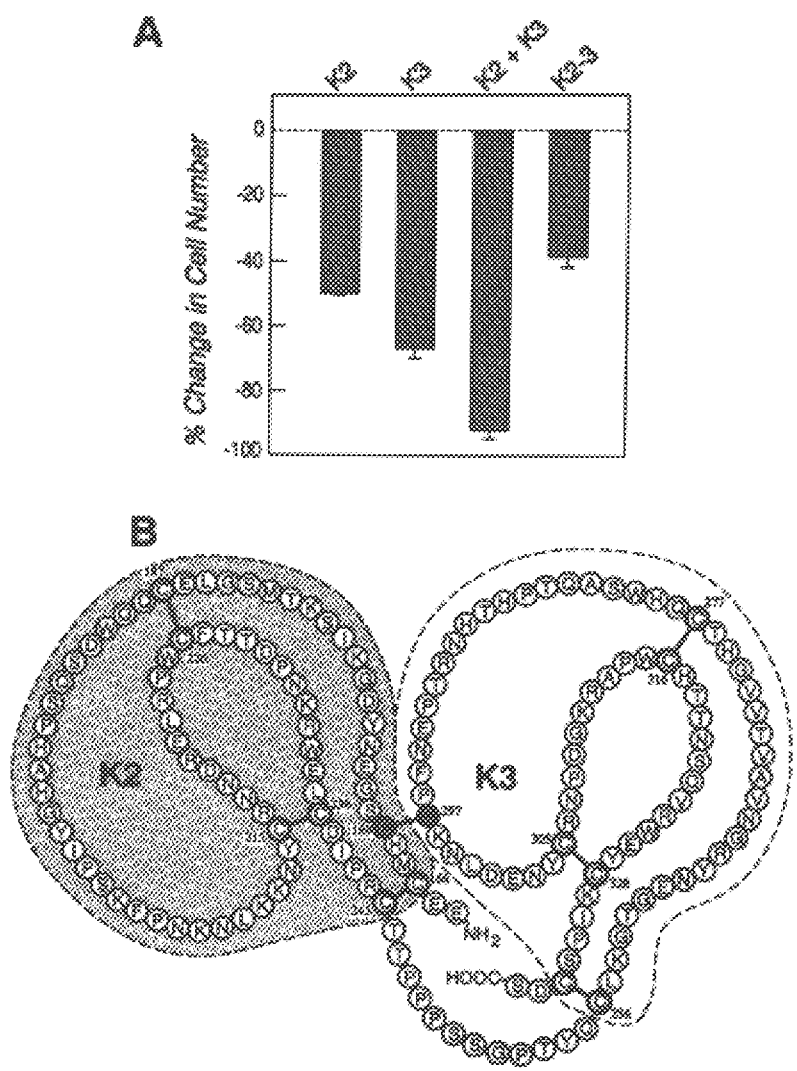

FIGS. 32A–B show an additive inhibitory activity of recombinant kringle 2 and kringle 3. (A) The intact fragment of rK2–3 (also see FIG. 31) displayed a weak inhibitory effect only at the concentration of 320 nM. At the same concentration, an additive inhibition was seen when mutant fragments of rK2 cysteine replaced by serine at the position of 169) and K3 (cysteine replaced by serine at the position of 297) were assayed together on BCE cells. Each value represents the mean +/– SEM of triplicates. (B) Schematic structure and amino acid sequence of K2 and K3. An interchain kringle disulfide bond was previously reported to be present between $cysteine^{169}$ of K2 and $cysteine^{297}$ of K3 (Söhndel, S., Hu, C.-K., Marti, D., Affolter, M., Schaller, J., Llinas, M., and Rickli, E. E. (1996) *Biochem*. in press).

Figures 33A, 33B:
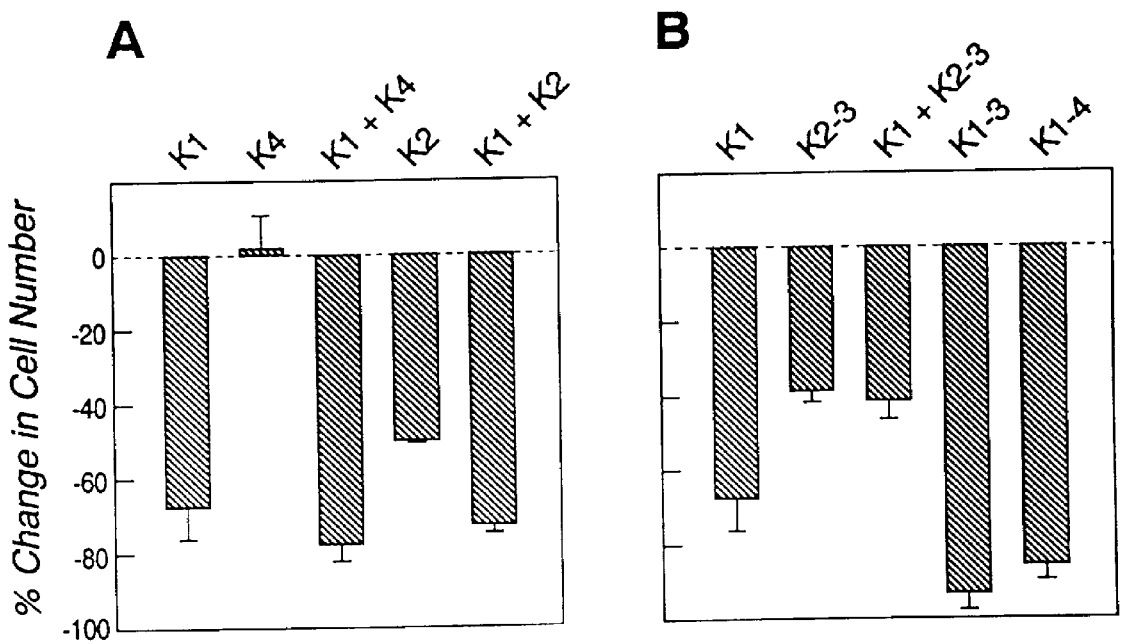

FIGS. 33A–B show an inhibition of endothelial proliferation by combinatorial kringle fragments. The assay was performed with a concentration of 320 nM for each kringle fragment. Values represent the mean of three determinations (+/– SEM) as percentages of inhibition. (A) Inhibitory effects of fragments by combination of various individual kringles. (B) Combinatorial inhibitory activity of combined kringle fragments.

Figure 34:
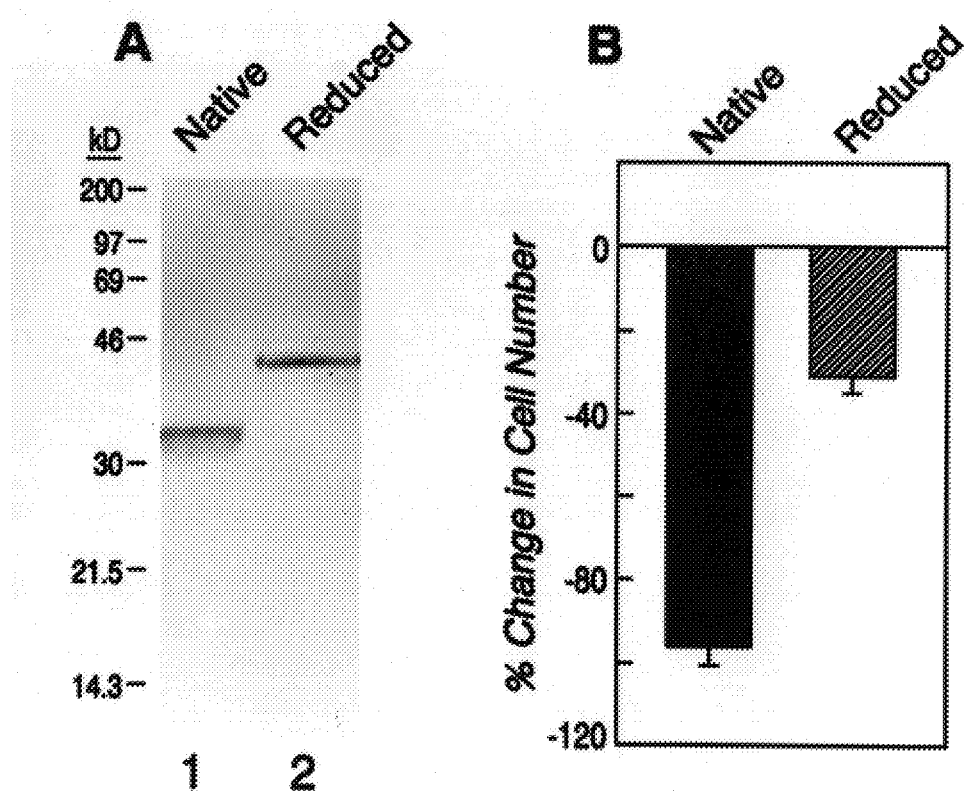

FIGS. 34A–B show an inhibitory activity of angiostatin on endothelial cells after reduction and alkylation. (A) SDS-PAGE analysis of the reduced (lane 2) and non-reduced (lane 1) forms of human angiostatin. Purified human angiostatin was reduced with DTT followed by alkylation of the protein with an excess amount of iodoacetamide. The treated samples were dialyzed and assayed on BCE cells. (B) Inhibition of BCE cell proliferation by reduced and non-reduced forms of angiostatin at a concentration of 320 nM. Data represents the mean of inhibition +/– SEM of triplicates.

FIG. 35 shows an amino acid sequence alignment of putative kringle domains of human angiostatin. The sequences of four kringle domains were aligned according to their conserved cysteines. Identical and conserved amino acids are shaded. The boxed amino acids in kringle 4 show the positively charged double lysines adjacent to conserved cysteine residues of 22 and 80.

Figure 36:
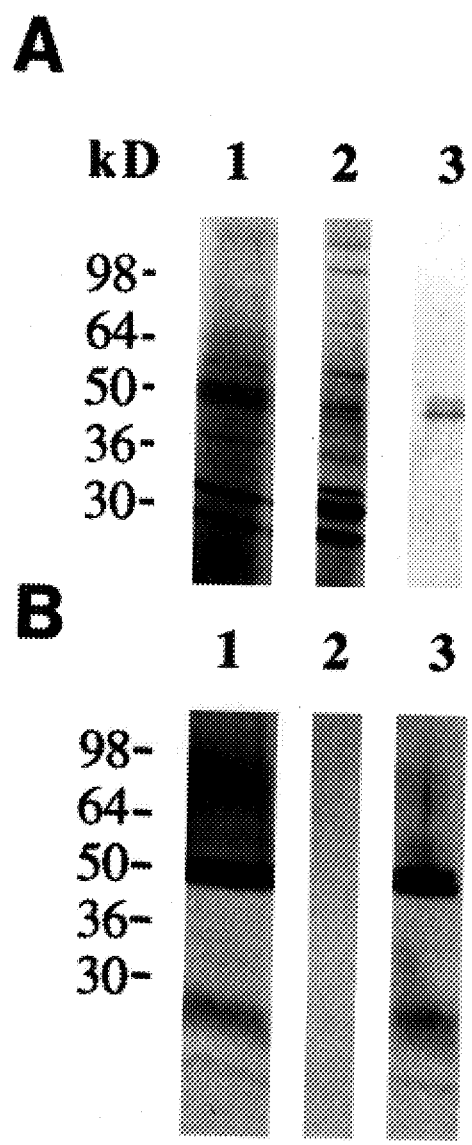

FIG. 36 shows lysine-binding characteristics and reactivity of expressed angiostatin.

FIG. 36A shows a Coomassie stained gel (40 µl load).

FIG. 36B shows an immunoblot (20 µl load) of similar gel. Lane:1 shows broth from shake flasks of induced cultures showing angiostatin protein at about 50 kD and a few other proteins. Broth from induced cultures is diluted 1:1 with buffer and directly loaded onto lysine-sepharose. Lane:2 shows the unbound fraction that passed through the lysine column. All angiostatin protein expressed by *P. pastoris* binds to the lysine column. Lane:3 shows specific elution with 0.2M amino caproic acid showing that *P. pastoris* expressed angiostatin protein binds lysine and can be purified in a single step to homogeneity over a lysine-sepharose. Also, the *P. pastoris* expressed angiostatin protein is recognized by a conformationally dependent monoclonal antibody (VAP) raised against kringles 1 to 3.

FIG. 37 shows *P. pastoris* expressed angiostatin protein is seen as a doublet that migrates at 49 kD and 51.5 kD on denatured unreduced SDS-PAGE Coomassie stained gels. Removing the single N-linked complex chain from the expressed angiostatin protein with N-glycanase specific for high mannose structures results in a single band of 49.5 kD. Panel A and panel B show a Coomassie stained gel and an immunoblot of a similar gel respectively. Lane:1 shows a purified *P. pastoris* expressed angiostatin protein. Lane:2 shows a purified *P. pastoris* expressed angiostatin protein incubated in digestion conditions without N-glycanase. Lane:3 shows purified *P. pastoris* expressed angiostatin protein digested with N-glycanase.

Figure 38A:

FIG. 38A shows 4 µg of purified *P. pastoris* expressed angiostatin protein as a doublet on a Coomassie gel.

Figure 38B:
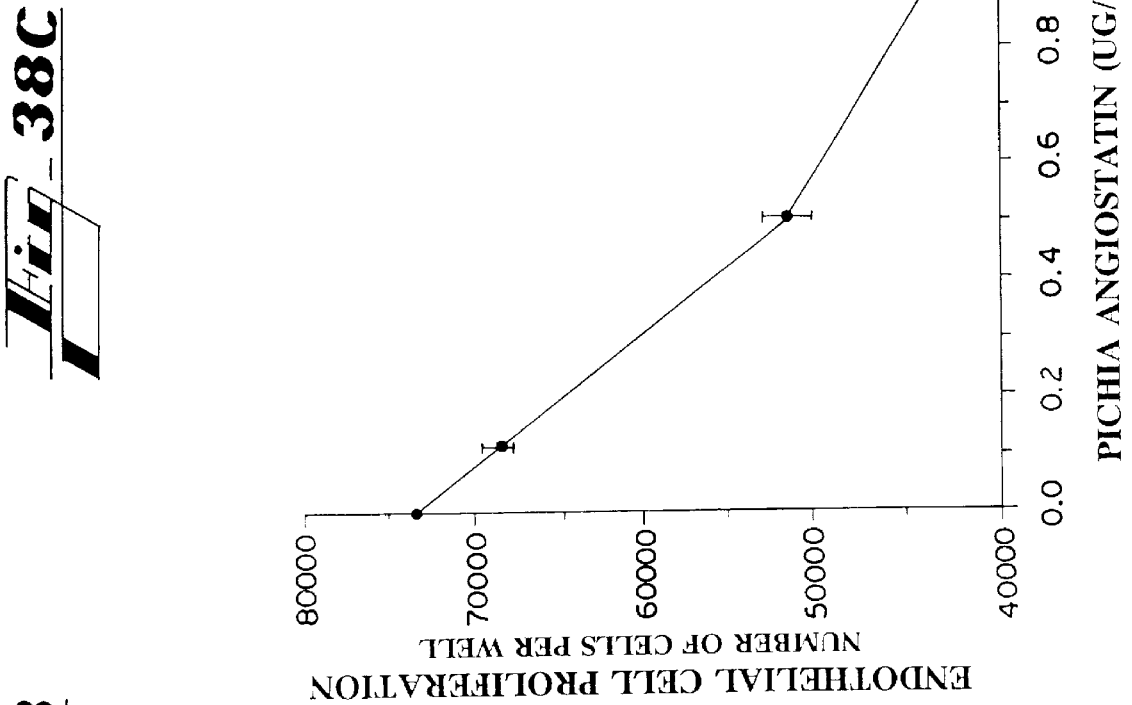

FIG. 38B shows that the purified recombinant inhibits BCE proliferation. The BCE assay cell counts obtained after 72 hours is shown, in the presence (●) or absence (o) of bFGF, and in the presence of bFGF with PBS as control (Δ), and in the presence of bFGF with *P. pastoris* expressed angiostatin protein (▲).

Figure 38C:
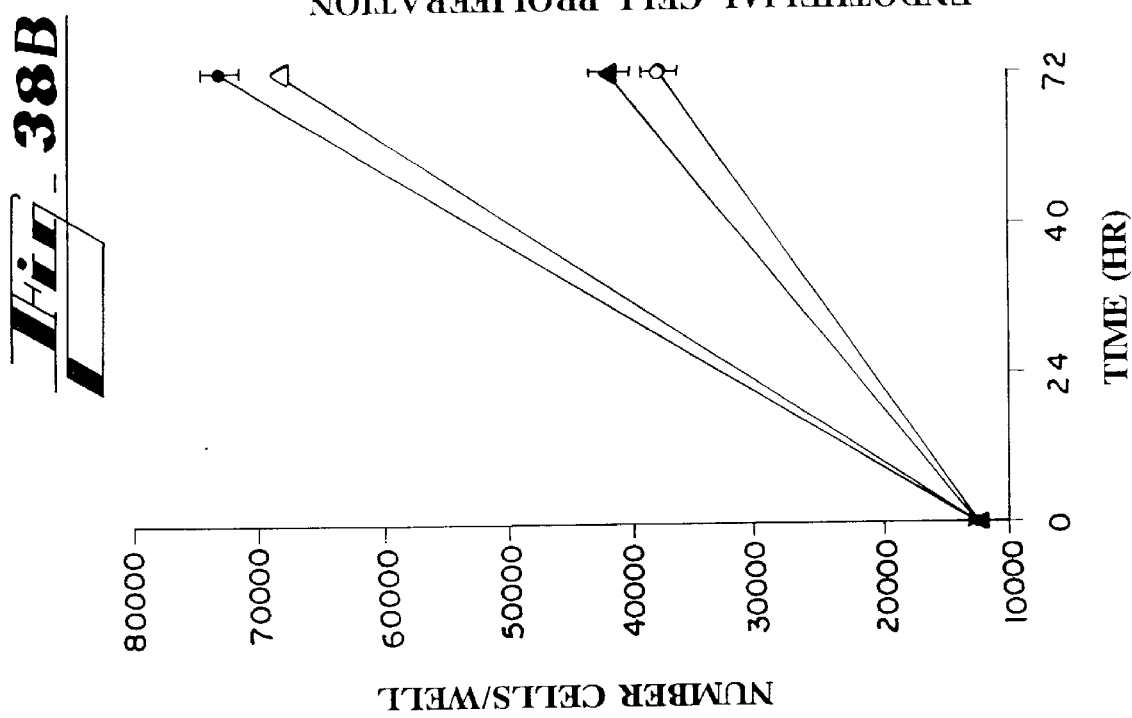

FIG. 38C shows that the inhibition is dose dependent.

FIG. 39 shows *P. pastoris* expressed purified angiostatin was given systemically (subcutaneous) to mice with primary tumors.

Figures 39A, 39B:
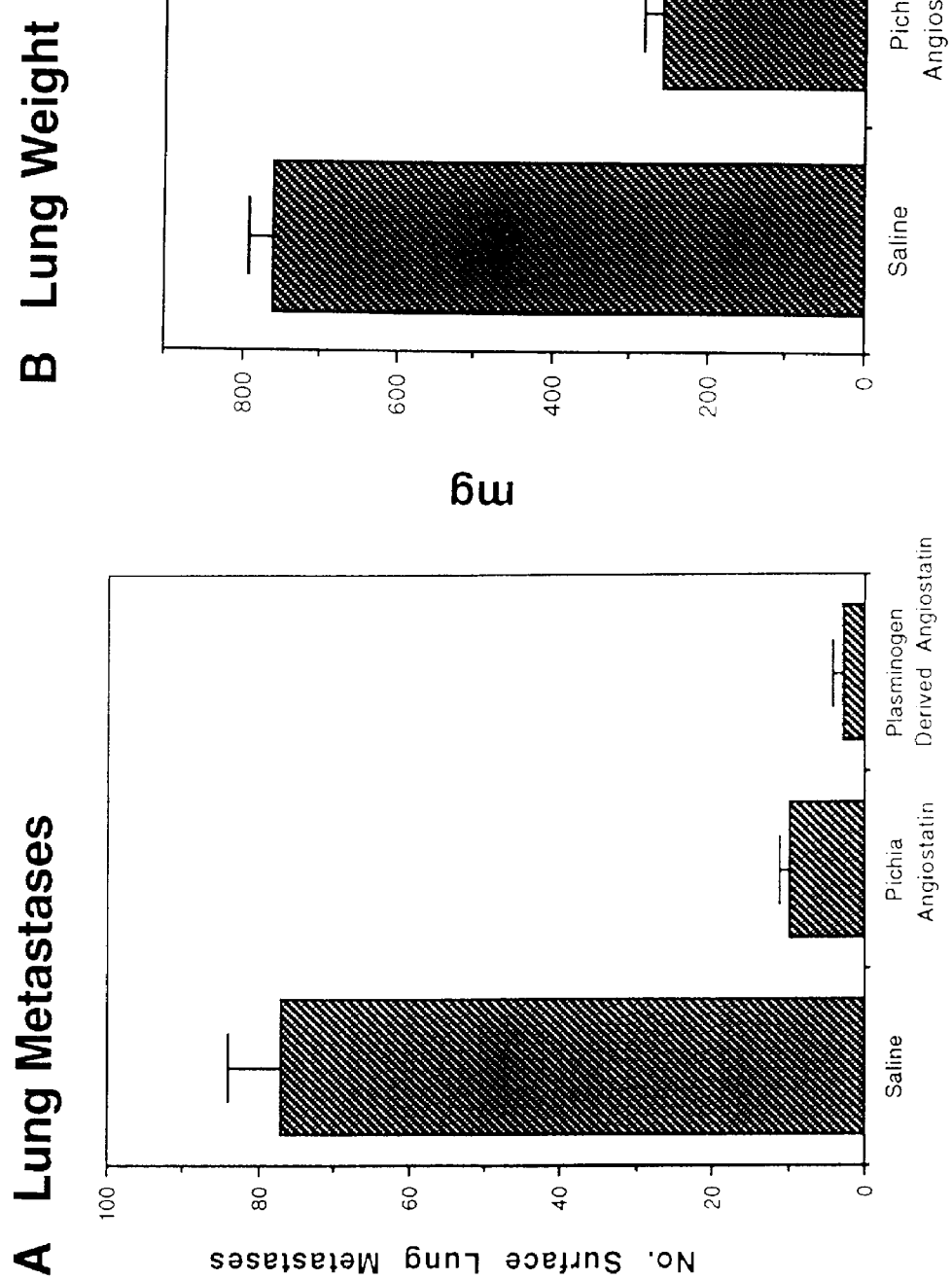

FIGS. 39A and B show the number of metastases and the lung weights respectively of mice treated daily with saline or *P. pastoris* expressed angiostatin or plasminogen derived angiostatin protein. In contrast to the lungs of mice treated with saline, lungs of mice treated with *P. pastoris* expressed angiostatin protein or with plasminogen derived angiostatin protein were non-vascularized and metastases were potently suppressed.

Figure 40:
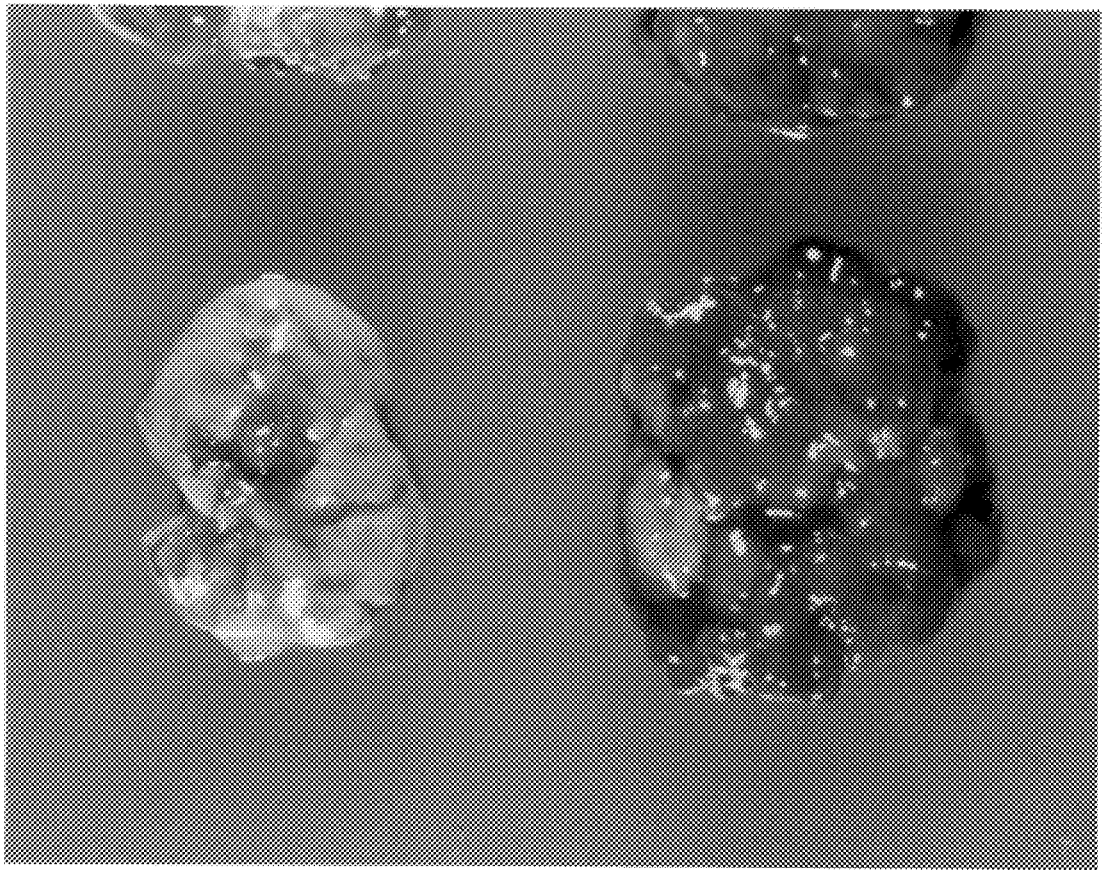

FIG. 40 shows that the lungs of mice treated with *P. pastoris* expressed angiostatin were pink with micrometastases while the lungs of the saline control group were completely covered with vascularized metastases.

DETAILED DESCRIPTION

The present invention includes compositions and methods for the detection and treatment of diseases and processes that are mediated by or associated with angiogenesis. The composition is angiostatin, which can be isolated from body fluids including, but not limited to, serum, urine and ascites, or synthesized by chemical or biological methods (e.g. cell culture, recombinant gene expression, protein synthesis, and in vitro enzymatic catalysis of plasminogen or plasmin to yield active angiostatin). Recombinant techniques include gene amplification from DNA sources using the polymerase chain reaction (PCR), and gene amplification from RNA sources using reverse transcriptase/PCR. Angiostatin inhibits the growth of blood vessels into tissues such as unvascularized or vascularized tumors.

The present invention also encompasses a composition comprising, a vector containing a DNA sequence encoding angiostatin, wherein the vector is capable of expressing angiostatin when present in a cell, a composition comprising a cell containing a vector, wherein the vector contains a DNA sequence encoding angiostatin or fragments or analogs thereof, and wherein the vector is capable of expressing angiostatin when present in the cell, and a method comprising, implanting into a human or non-human animal a cell containing a vector, wherein the vector contains a DNA sequence encoding angiostatin, and wherein the vector is capable of expressing angiostatin when present in the cell.

Still further, the present invention encompasses angiostatin, angiostatin fragments, angiostatin antisera, angiostatin receptor agonists or angiostatin receptor antagonists that are combined with pharmaceutically acceptable excipients, and optionally sustained-release compounds or compositions, such as biodegradable polymers, to form therapeutic compositions. In particular, the invention includes a composition comprising an antibody that specifically binds to angiostatin, wherein the antibody does not bind to plasminogen.

More particularly, the present invention includes a protein designated angiostatin that has a molecular weight of approximately 38 to 45 kilodaltons (kD) that is capable of overcoming the angiogenic activity of endogenous growth factors such as bFGF, in vitro. Angiostatin is a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The term "substantially similar," when used in reference to angiostatin amino acid sequences, means an amino acid sequence having anti-angiogenic activity and having a molecular weight of approximately 38 kD to 45 kD, which also has a high degree of sequence homology to the protein fragment of mouse plasminogen beginning approximately at amino acid number 98 in mouse plasminogen and weighing 38 kD to 45 kD. A high degree of homology means at least approximately 60% amino acid homology, desirably at least approximately 70% amino acid homology, and more desirably at least approximately 80% amino acid homology. The term "endothelial inhibiting activity" as used herein means the capability of a molecule to inhibit angiogenesis in general and, for example, to inhibit the growth of bovine capillary endothelial cells in culture in the presence of fibroblast growth factor.

The amino acid sequence of the complete murine plasminogen molecule is shown in FIG. 1 and in SEQ ID NO:1, The sequence for angiostatin begins approximately at amino acid 98. Active human angiostatin may start at either amino acid 97 or 99 of the intact human plasminogen molecule. The amino acid sequence of the first 339 amino acids of angiostatin from mouse is shown in FIG. 2, (SEQ ID NO:2), and is compared with the sequences of corresponding plasminogen protein fragments from human (SEQ ID NO:3, Rhesus monkey (SEQ ID NO:4), porcine (SEQ ID NO:5) and bovine (SEQ ID NO:6) plasminogen. Given that these sequences are identical in well over 50% of their amino acids, it is to be understood that the amino acid sequence of the angiostatin is substantially similar among species. The total number of amino acids in angiostatin is not known precisely but is defined by the molecular weight of the active molecule. The amino acid sequence of the angiostatin of the present invention may vary depending upon from which species the plasminogen molecule is derived. Thus, although the angiostatin of the present invention that is derived from human plasminogen has a slightly different sequence than angiostatin derived from mouse, it has anti-angiogenic activity as shown in a mouse tumor model.

Angiostatin has been shown to be capable of inhibiting the growth of endothelial cells in vitro. Angiostatin does not inhibit the growth of cell lines derived from other cell types. Specifically, angiostatin has no effect on Lewis lung carcinoma cell lines, mink lung epithelium, 3T3 fibroblasts, bovine aortic smooth muscle cells, bovine retinal pigment epithelium, MDCk cells (canine renal epithelium), WI38 cells (human fetal lung fibroblasts) EFN cells (murine fetal fibroblasts) and LM cells (murine connective tissue). Endogenous angiostatin in a tumor bearing mouse is effective at inhibiting metastases at a systemic concentration of approximately 10 mg angiostatin/kg body weight.

Angiostatin has a specific three dimensional conformation that is defined by the kringle region of the plasminogen molecule. (Robbins, K. C., "The plasminogenplasmin plasmin enzyme system" *Hemostasis and Thrombosis, Basic Principles and Practice*, 2nd Edition, ed. by Colman, R. W. et al. J. B. Lippincott Company, pp. 340–357, 1987) There are five such kringle regions, which are conformationally related motifs and have substantial sequence homology, in the $NH_2$ terminal portion of the plasminogen molecule. The three dimensional conformation of angiostatin is believed to encompass plasminogen kringle regions 1 through 3 and a part of kringle region 4. Each kringle region of the plasminogen molecule contains approximately 80 amino acids and contains 3 disulfide bonds. This cysteine motif is known to exist in other biologically active proteins. These proteins include, but are not limited to, pro thrombin, hepatocyte growth factor, scatter factor and macrophage stimulating protein. (Yoshimura, T, et al., "Cloning, sequencing, and expression of human macrophage stimulating protein (MSP, MST1) confirms MSP as a member of the family of kringle proteins and locates the MSP gene on Chromosome 3" *J.*

Biol. Chem., Vol. 268, No. 21, pp. 15461–15468, 1993). It is contemplated that any isolated protein or protein having a three dimensional kringle-like conformation or cysteine motif that has anti-angionenic activity in vivo, is part of the present invention.

The present invention also includes the detection of the angiostatin in body fluids and tissues for the purpose of diagnosis or prognosis of diseases such as cancer. The present invention also includes the detection of angiostatin binding sites and receptors in cells and tissues. The present invention also includes methods of treating or preventing angiogenic diseases and processes including, but not limited to, arthritis and tumors by stimulating the production of angiostatin, and/or by administering substantially purified angiostatin, or angiostatin agonists or antagonists, and/or angiostatin antisera or antisera directed against angiostatin antisera to a patient. Additional treatment methods include administration of angiostatin, angiostatin fragments, angiostatin analogs, angiostatin antisera, or angiostatin receptor agonists and antagonists linked to cytotoxic agents. It is to be understood that the angiostatin can be animal or human in origin. Angiostatin can also be produced synthetically by chemical reaction or by recombinant techniques in conjunction with expression systems. Angiostatin can also be produced by enzymatically cleaving isolated plasminogen or plasmin to generate proteins having anti-angiogenic activity. Angiostatin may also be produced by compounds that mimic the action of endogenous enzymes that cleave plasminogen to angiostatin. Angiostatin production may also be modulated by compounds that affect the activity of plasminogen cleaving enxymes.

Passive antibody therapy using antibodies that specifically bind angiostatin can be employed to modulate angiogenic-dependent processes such as reproduction, development, and wound healing and tissue repair. In addition, antisera directed to the Fab regions of angiostatin antibodies can be administered to block the ability of endogenous angiostatin antisera to bind angiostatin.

The present invention also encompasses gene therapy whereby the gene encoding angiostatin is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as angiostatin may be placed in a patient and thus prevent occurrence of angiogenesis; or a gene that makes tumor cells more susceptible to radiation could be inserted and then radiation of the tumor would cause increased killing of the tumor cells.

Many protocols for transfer of angiostatin DNA or angiostatin regulatory sequences are envisioned in this invention. Transfection of promoter sequences, other than one normally found specifically associated with angiostatin, or other sequences which would increase production of angiostatin protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate angiostatin (or the angiostatin receptor) in cells not normally expressing angiostatin (or the angiostatin receptor) .

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of angiostatin DNA or angiostatin regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product proteins at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of angiostatin may be accomplished by administering compounds that bind to the angiostatin gene, or control regions associated with the angiostatin gene, or its corresponding RNA transcript to modify the rate of transcription or translation. Additionally, cells transfected with a DNA sequence encoding angiostatin may be administered to a patient to provide an in vivo source of angiostatin. For example, cells may be transfected with a vector containing a nucleic acid sequence encoding angiostatin.

The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising an angiostatin DNA sequence is operatively linked to an expression control sequence to form an expression vector capable of expressing angiostatin. The transfected cells may be cells derived from the patient's normal tissue, the patient's diseased tissue, or may be non-patient cells.

For example, tumor cells removed from a patient can be transfected with a vector capable of expressing the angiostatin protein of the present invention, and re-introduced into the patient. The transfected tumor cells produce angiostatin levels in the patient that inhibit the growth of the tumor. Patients may be human or non-human animals. Cells may also be transfected by non-vector, or physical or chemical methods known in the art such as electroporation, ionoporation, or via a "gene gun." Additionally, angiostatin DNA may be directly injected, without the aid of a carrier, into a patient. In particular, angiostatin DNA may be injected into skin, muscle or blood.

The gene therapy protocol for transfecting angiostatin into a patient may either be through integration of the angiostatin DNA into the genome of the cells, into minichromosomes or as a separate replicating or non-replicating DNA construct in the cytoplasm or nucleoplasm of the cell. Angiostatin expression may continue for a long-period of time or may be reinjected periodically to maintain a desired level of the angiostatin protein in the cell, the tissue or organ or a determined blood level.

Angiostatin can be isolated on an HPLC C4 column (see Table 3). The angiostatin protein is eluted at 30 to 35% in an acetonitrile gradient. On a sodium dodecyl sulfate polyacrylamide gel electrophoresis (PAGE) gel under reducing conditions, the protein band with activity eluted as a single peak at approximately 38 kilodaltons.

The inventors have shown that a growing primary tumor is associated with the release into the blood stream of specific inhibitor(s) of endothelial cell proliferation, including angiostatin which can suppress angiogenesis within a metastasis and thereby inhibit the growth of the metastasis itself. The source of the angiostatin associated with the primary tumor is not known. The compound may be produced by degradation of plasminogen by a specific protease, or angiostatin could be produced by expression of a specific gene coding for angiostatin.

The angiogenic phenotype of a primary tumor depends on production of angiogenic proteins in excess of endothelial cell inhibitors which are elaborated by normal cells, but are believed to be down-regulated during transformation to neoplasia. While production of angiostatin may be down-regulated in an individual tumor cell relative to production by its parent cell type, the total amount of inhibitor elaborated by the whole tumor may be sufficient to enter the circulation and suppress endothelial growth at remote sites of micrometastases. Angiostatin remains in the circulation for a significantly longer time than the angiogenic protein(s) released by a primary tumor. Thus, the angiogenic proteins appear to act locally, whereas angiostatin acts globally and circulates in the blood with a relatively long half-life. The half-life of the angiostatin is approximately 12 hours to 5 days.

Although not wanting to be bound by the following hypothesis, it is believed that when a tumor becomes angiogenic it releases one or more angiogenic proteins (e.g., aFGF, bFGF, VEGF, IL-8, GM-CSF, etc.), which act locally, target endothelium in the neighborhood of a primary tumor from an extravascular direction, and do not circulate (or circulate with a short half-life). These angiogenic proteins must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act remotely at a distance from the primary tumor, target capillary endothelium of a metastasis from an intravascular direction, and continue to circulate. Thus, just at the time when a remote metastasis might begin to initiate angiogenesis, the capillary endothelium in its neighborhood could be inhibited by incoming angiostatin.

Once a primary tumor has reached sufficient size to cause angiostatin to be released continuously into the circulation, it is difficult for a second tumor implant (or a micrometastasis) to initiate or increase its own angiogenesis. If a second tumor implant (e.g., into the subcutaneous space, or into the cornea, or intravenously to the lung) occurs shortly after the primary tumor is implanted, the primary tumor will not be able to suppress the secondary tumor (because angiogenesis in the secondary tumor will already be well underway). If two tumors are implanted simultaneously (e.g., in opposite flanks), the inhibitors may have an equivalent inhibiting effect on each other.

The angiostatin of the present invention can be:

(i) Administered to tumor-bearing humans or animals as anti-angiogenic therapy;

(ii) Monitored in human or animal serum, urine, or tissues as prognostic markers; and (iii) Used as the basis to analyze serum and urine of cancer patients for similar angiostatic molecules.

It is contemplated as part of the present invention that angiostatin can be isolated from a body fluid such as blood or urine of patients or the angiostatin can be produced by recombinant DNA methods or synthetic protein chemical methods that are well known to those of ordinary skill in the art. Protein purification methods are well known in the art and a specific example of a method for purifying angiostatin, and assaying for inhibitor activity is provided in the examples below. Isolation of human endogenous angiostatin is accomplished using similar techniques.

One example of a method of producing angiostatin using recombinant DNA techniques entails the steps of (1) identifying and purifying angiostatin as discussed above, and as more fully described below, (2) determining the N-terminal amino acid sequence of the purified inhibitor, (3) synthetically generating 5' and 3' DNA oligonucleotide primers for the angiostatin sequence, (4) amplifying the angiostatin gene sequence using polymerase, (5) inserting the amplified sequence into an appropriate vector such as an expression vector, (6) inserting the gene containing vector into a microorganism or other expression system capable of expressing the inhibitor gene, and (7) isolating the recombinantly produced inhibitor. Appropriate vectors include viral, bacterial and eukaryotic (such as yeast) expression vectors. The above techniques are more fully described in laboratory manuals such as "Molecular Cloning: A Laboratory Manual" Second Edition by Sambrook et al., Cold Spring Harbor Press, 1989. The DNA sequence of human plasminogen has been published (Browne, M. J., et al., "Expression of recombinant human plasminogen and aglycoplasminogen in HeLa cells" Fibrinolysis Vol.5 (4). 257–260, 1991) and is incorporated herein by reference The gene for angiostatin may also be isolated from cells or tissue (such as tumor cells) that express high levels of angiostatin by (1) isolating messenger RNA from the tissue, (2) using reverse transcriptase to generate the corresponding DNA sequence and then (3) using the polymerase chain reaction (PCR) with the appropriate primers to amplify the DNA sequence coding for the active angiostatin amino acid sequence.

Yet another method of producing angiostatin, or biologically active fragments thereof, is by protein synthesis. Once a biologically active fragment of an angiostatin is found using the assay system described more fully below, it can be sequenced, for example by automated protein sequencing methods. Alternatively, once the gene or DNA sequence which codes for angiostatin is isolated, for example by the methods described above, the DNA sequence can be determined using manual or automated sequencing methods well know in the art. The nucleic acid sequence in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the protein is known, the fragment can be synthesized by techniques well known in the art, as exemplified by "Solid Phase Protein Synthesis: A Practical Approach" E. Atherton and R. C. Sheppard, IRL Press, Oxford, England. Similarly, multiple fragments can be synthesized which are subsequently linked together to form larger fragments. These synthetic protein fragments can also be made with amino acid substitutions at specific locations to test for agonistic and antagonistic activity in vitro and in vivo. Protein fragments that possess high affinity binding to tissues can be used to isolate the angiostatin receptor on affinity columns. Isolation and purification of the angiostatin receptor is a fundamental step towards elucidating the mechanism of action of angiostatin. Isolation of an angiostatin receptor and identification of angiostatin agonists and antagonists will facilitate development of drugs to modulate the activity of the angiostatin receptor, the final pathway to biological activity. Isolation of the receptor enables the construction of nucleotide probes to monitor the location and synthesis of the receptor, using in situ and solution hybridization technology. Further, the gene for the angiostatin receptor can be isolated, incorporated into an expression vector and transfected into cells, such as patient tumor cells to increase the ability of a cell type, tissue or tumor to bind angiostatin and inhibit local angiogenesis.

Angiostatin is effective in treating diseases or processes that are mediated by, or involve, angiogenesis. The present invention includes the method of treating an angiogenesis mediated disease with an effective amount of angiostatin, or a biologically active fragment thereof, or combinations of angiostatin fragments that collectively possess antiangiogenic activity, or angiostatin agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Angiostatin is useful in the treatment of disease of excessive or abnormal stimulation of endothelial cells. These diseases include, but are not limited to, intestinal adhesions, Crohn's disease, atherosclerosis, scleroderma, and hypertrophic scars, i.e., keloids. Angiostatin can be used as a birth control agent by preventing vascularization required for embryo implantation. Angiostatin is useful in the treatment of diseases that have angiogenesis as a pathologic consequence such as cat scratch disease (*Rochele minalia quintosa*) and ulcers (*Helicobacter pylori*).

The synthetic protein fragments of angiostatin have a variety of uses. The protein that binds to the angiostatin receptor with high specificity and avidity is radiolabeled and employed for visualization and quantitation of binding sites using autoradiographic and membrane binding techniques. This application provides important diagnostic and research tools. Knowledge of the binding properties of the angiostatin receptor facilitates investigation of the transduction mechanisms linked to the receptor.

In addition, labeling angiostatin proteins with short lived isotopes enables visualization of receptor binding sites in vivo using positron emission tomography or other modern radiographic techniques to locate tumors with angiostatin binding sites.

Systematic substitution of amino acids within these synthesized proteins yields high affinity protein agonists and antagonists to the angiostatin receptor that enhance or diminish angiostatin binding to its receptor. Such agonists are used to suppress the growth of micrometastases, thereby limiting the spread of cancer. Antagonists to angiostatin are applied in situations of inadequate vascularization, to block the inhibitory effects of angiostatin and promote angiogenesis. For example, this treatment may have therapeutic effects to promote wound healing in diabetics.

Angiostatin proteins are employed to develop affinity columns for isolation of the angiostatin receptor from cultured tumor cells. Isolation and purification of the angiostatin receptor is followed by amino acid sequencing. Using this information the gene or genes coding for the angiostatin receptor can be identified and isolated. Next, cloned nucleic acid sequences are developed for insertion into vectors capable of expressing the receptor. These techniques are well known to those skilled in the art. Transfection of the nucleic acid sequence(s) coding for angiostatin receptor into tumor cells, and expression of the receptor by the transfected tumor cells enhances the responsiveness of these cells to endogenous or exogenous angiostatin and thereby decreasing the rate of metastatic growth.

Cytotoxic agents such as ricin, are linked to angiostatin, and high affinity angiostatin protein fragments, thereby providing a tool for destruction of cells that bind angiostatin. These cells may be found in many locations, including but not limited to, micrometastases and primary tumors. Proteins linked to cytotoxic agents are infused in a manner designed to maximize delivery to the desired location. For example, ricinlinked high affinity angiostatin fragments are delivered through a cannula into vessels supplying the target site or directly into the target. Such agents are also delivered in a controlled manner through osmotic pumps coupled to infusion cannulae. A combination of angiostatin antagonists may be co-applied with stimulators of angiogenesis to increase vascularization of tissue. This therapeutic regimen provides an effective means of destroying metastatic cancer.

Angiostatin may be used in combination with other compositions and procedures for the treatment of diseases. For example, a tumor may be treated conventionally with surgery, radiation or chemotherapy combined with angiostatin and then angiostatin may be subsequently administered to the patient to extend the dormancy of micrometastases and to stabilize and inhibit the growth of any residual primary tumor. Additionally, angiostatin, angiostatin fragments, angiostatin antisera, angiostatin receptor agonists, angiostatin receptor antagonists, or combinations thereof, are combined with pharmaceutically acceptable excipients, and optionally sustained-release matrix, such as biodegradable polymers, to form therapeutic compositions.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating therapeutic composition of the present invention may be a solid, liquid or aerosol and may be administered by any known route of administration. Examples of solid therapeutic compositions include pills, creams, and implantable dosage units. The pills may be administered orally, the therapeutic creams may be administered topically. The implantable dosage unitst may be administered locally, for example at a tumor site, or which may be implanted for systemic release of the therapeutic angiogenesis-modulating composition, for example subcutaneously. Examples of liquid composition include formulations adapted for injection subcutaneously, intravenously, intraarterially, and formulations for topical and intraocular administration. Examples of aersol formulation include inhaler formulation for administration to the lungs.

The angiostatin of the present invention also can be used to generate antibodies that are specific for the inhibitor and its receptor. The antibodies can be either polyclonal antibodies or monoclonal antibodies. These antibodies that specifically bind to the angiostatin or angiostatin receptors can be used in diagnostic methods and kits that are well known to those of ordinary skill in the art to detect or quantify the angiostatin or angiostatin receptors in a body fluid or tissue. Results from these tests can be used to diagnose or predict the occurrence or recurrence of a cancer and other angiogenic mediated diseases.

The angiostatin also can be used in a diagnostic method and kit to detect and quantify antibodies capable of binding angiostatin. These kits would permit detection of circulating angiostatin antibodies which indicates the spread of micrometastases in the presence of angiostatin secreted by primary tumors in situ. Patients that have such circulating anti-angiostatin antibodies may be more likely to develop multiple tumors and cancers, and may be more likely to have recurrences of cancer after treatments or periods of remission. The Fab fragments of these anti-angiostatin antibodies may be used as antigens to generate anti-angiostatin Fab-fragment antisera which can be used to neutralize anti-angiostatin antibodies. Such a method would reduce the removal of circulating angiostatin by anti-angiostatin antibodies, thereby effectively elevating circulating angiostatin levels.

Another aspect of the present invention is a method of blocking the action of excess endogenous angiostatin. This can be done by passively immunizing a human or animal with antibodies specific for the undesired angiostatin in the system. This treatment can be important in treating abnormal ovulation, menstruation and placentation, and vasculogenesis. This provides a useful tool to examine the effects of angiostatin removal on metastatic processes. The Fab fragment of angiostatin antibodies contains the binding site for angiostatin. This fragment is isolated from angiostatin antibodies using techniques known to those skilled in the art. The Fab fragments of angiostatin antisera are used as antigens to generate production of anti-Fab fragment serum. Infusion of this antiserum against the Fab fragments of angiostatin prevents angiostatin from binding to angiostatin antibodies. Therapeutic benefit is obtained by neutralizing endogenous anti-angiostatin antibodies by blocking the binding of angiostatin to the Fab fragments of anti-angiostatin. The net effect of this treatment is to facilitate the ability of endogenous circulating angiostatin to reach target cells, thereby decreasing the spread of metastases.

It is to be understood that the present invention is contemplated to include any derivatives of the angiostatin that have endothelial inhibitory activity. The present invention includes the entire angiostatin protein, derivatives of the angiostatin protein and biologically-active fragments of the angiostatin protein. These include proteins with angiostatin activity that have amino acid substitutions or have sugars or other molecules attached to amino acid functional groups. The present invention also includes genes that code for angiostatin and the angiostatin receptor, and to proteins that are expressed by those genes.

The proteins and protein fragments with the angiostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the angiostatin may be incorporated into biodegradable polymers allowing for sustained release of the compound, the polymers being implanted in the vicinity of where drug delivery is desired, for example, at the site of a tumor or implanted so that the angiostatin is slowly released systemically. Osmotic minipumps may also be used to provide controlled delivery of high concentrations of angiostatin through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the angiostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the angiostatin can be administered. Depending upon the half-life of the angiostatin in the particular animal or human, the angiostatin can be administered between several times per day to once a week. It is to be understood that the present invention has application for both human and veterinary use. The methods of the present invention contemplate single as well as multiple administrations, given either simultaneously or over an extended period of time.

The angiostatin formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The angiostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with angiostatin proteins, or biologically functional protein fragements thereof, to provide dual therapy to the patient.

Angiogenesis inhibiting proteins of the present invention can be synthesized in a standard microchemical facility and purity checked with HPLC and mass spectrophotometry. Methods of protein synthesis, HPLC purification and mass spectrophotometry are commonly known to those skilled in these arts. Angiostatin proteins and angiostatin receptors proteins are also produced in recombinant *E. coli* or yeast expression systems, and purified with column chromatography.

Different protein fragments of the intact angiostatin molecule can be synthesized for use in several applications including, but not limited to the following; as antigens for the development of specific antisera, as agonists and antagonists active at angiostatin binding sites, as proteins to be linked to, or used in combination with, cytotoxic agents for targeted killing of cells that bind angiostatin. The amino acid sequences that comprise these proteins are selected on the basis of their position on the exterior regions of the molecule and are accessible for binding to antisera. The amino and carboxyl termini of angiostatin, as well as the mid-region of the molecule are represented separately among the fragments to be synthesized.

These protein sequences are compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules, thereby enhancing the potential for high specificity in the development of antisera, agonists and antagonists to angiostatin.

Angiostatin and angiostatin derived proteins can be coupled to other molecules using standard methods. The amino and carboxyl termini of angiostatin both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the protein. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Angiostatin proteins are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of an angiostatin protein with $^{125}I$ is accomplished using chloramine T and $Na^{125}I$ of high specific activity. The reaction is terminated with sodium metabisulfite and the mixture is desalted on disposable columns. The labeled protein is eluted from the column and fractions are collected. Aliquots are removed from each fraction and radioactivity measured in a gamma counter. In this manner, the unreacted $Na^{125}I$ is separated from the labeled angiostatin protein. The protein fractions with the highest specific radioactivity are stored for subsequent use such as analysis of the ability to bind to angiostatin antisera.

Another application of protein conjugation is for production of polyclonal antisera. For example, angiostatin proteins containing lysine residues are linked to purified bovine serum albumin using glutaraldehyde. The efficiency of the reaction is determined by measuring the incorporation of radiolabeled protein. Unreacted glutaraldehyde and protein are separated by dialysis. The conjugate is stored for subsequent use.

Antiserum against angiostatin, angiostatin analogs, protein fragments of angiostatin and the angiostatin receptor can be generated. After protein synthesis and purification, both monoclonal and polyclonal antisera are raised using established techniques known to those skilled in the art. For example, polyclonal antisera may be raised in rabbits, sheep, goats or other animals. Angiostatin proteins conjugated to a carrier molecule such as bovine serum albumin, or angiostatin itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes. The serum is removed, aliquoted, and stored at 4° C. for immediate use or at −20 to −90° C. for subsequent analysis.

All serum samples from generation of polyclonal antisera or media samples from production of monoclonal antisera are analyzed for determination of antibody titer. Titer is established through several means, for example, using dot blots and density analysis, and also with precipitation of radiolabeled protein-antibody complexes using protein A, secondary antisera, cold ethanol or charcoal-dextran followed by activity measurement with a gamma counter. The highest titer antisera are also purified on affinity columns which are commercially available. Angiostatin proteins are coupled to the gel in the affinity column. Antiserum samples are passed through the column and anti-angiostatin antibodies remain bound to the column. These antibodies are subsequently eluted, collected and evaluated for determination of titer and specificity.

The highest titer angiostatin antisera is tested to establish the following; a) optimal antiserum dilution for highest specific binding of the antigen and lowest non-specific binding, b) the ability to bind increasing amounts of angiostatin protein in a standard displacement curve, c) potential cross-reactivity with related proteins and proteins, including plasminogen and also angiostatin of related species, d) ability to detect angiostatin proteins in extracts of plasma, urine, tissues, and in cell culture media.

Kits for measurement of angiostatin, and the angiostatin receptor, are also contemplated as part of the present invention. Antisera that possess the highest titer and specificity and can detect angiostatin proteins in extracts of plasma, urine, tissues, and in cell culture media are further examined to establish easy to use kits for rapid, reliable, sensitive, and specific measurement and localization of angiostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An angiostatin RIA is illustrated below. After successful radioiodination and purification of angiostatin or an angiostatin protein, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000–2500×g at 4° C. to precipitate the complexes of antibody bound to labeled antigen. The supernatant is removed by aspiration and the radioactivity in the pellets counted in a gamma counter. The antiserum dilution that binds approximately 10 to 40% of the labeled protein after subtraction of the non-specific binding is further characterized.

Next, a dilution range (approximately 0.1 pg to 10 ng) of the angiostatin protein used for development of the antiserum is evaluated by adding known amounts of the protein to tubes containing radiolabeled protein and antiserum. After an additional incubation period, for example, 24 to 48 hours, protein A is added and the tubes centrifuged, supernatant removed and the radioactivity in the pellet counted. The displacement of the binding of radiolabeled angiostatin protein by the unlabeled angiostatin protein (standard) provides a standard curve. Several concentrations of other angiostatin protein fragments, plasminogen, angiostatin from different species, and homologous proteins are added to the assay tubes to characterize the specificity of the angiostatin antiserum.

Extracts of various tissues, including but not limited to primary and secondary tumors, Lewis lung carcinoma, cultures of angiostatin producing cells, placenta, uterus, and other tissues such as brain, liver, and intestine, are prepared using extraction techniques that have been successfully employed to extract angiostatin. After lyophilization or Speed Vac of the tisssue extracts, assay buffer is added and different aliquots are placed into the RIA tubes. Extracts of known angiostatin producing cells produce displacement curves that are parallel to the standard curve, whereas extracts of tissues that do not produce angiostatin do not displace radiolabeled angiostatin from the angiostatin antiserum. In addition, extracts of urine, plasma, and cerebrospinal fluid from animals with Lewis lung carcinoma are added to the assay tubes in increasing amounts. Parallel displacement curves indicate the utility of the angiostatin assay to measure angiostatin in tissues and body fluids.

Tissue extracts that contain angiostatin are additionally characterized by subjecting aliquots to reverse phase HPLC. Eluate fractions are collected, dried in Speed Vac, reconstituted in RIA buffer and analyzed in the angiostatin RIA. The maximal amount of angiostatin immunoreactivity is located in the fractions corresponding to the elution position of angiostatin.

The assay kit provides instructions, antiserum, angiostatin or angiostatin protein, and possibly radiolabeled angiostatin and/or reagents for precipitation of bound angiostatin-angiostatin antibody complexes. The kit is useful for the measurement of angiostatin in biological fluids and tissue extracts of animals and humans with and without tumors.

Another kit is used for localization of angiostatin in tissues and cells. This angiostatin immunohistochemistry kit provides instructions, angiostatin antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This angiostatin immunohistochemistry kit permits localization of angiostatin in tissue sections and cultured cells using both light and electron microscopy. It is used for both research and clinical purposes. For example, tumors are biopsied or collected and tissue sections cut with a microtome to examine sites of angiostatin production. Such information is useful for diagnostic and possibly therapeutic purposes in the detection and treatment of cancer. Another method to visualize sites of angiostatin biosynthesis involves radiolabeling nucleic acids for use in in situ hybridization to probe for angiostatin messenger RNA. Similarly, the angiostatin receptor can be localized, visualized and quantitated with immunohistochemistry techniques.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Choice of an animal-tumor system in which growth of metastasis is inhibited by the primary tumor and is accelerated after removal of the primary tumor.

By screening a variety of murine tumors capable of inhibiting their own metastases, a Lewis lung carcinoma was selected in which the primary tumor most efficiently inhibited lung metastasis. Syngeneic C57BI6/J six-week-old male mice were injected (subcutaneous dorsum) with $1 \times 10^6$ tumor cells. Visible tumors first appeared after 3–4 days. When tumors were approximately 1500 mm$^3$ in size, mice were randomized into two groups. The primary tumor was completely excised in the first group and left intact in the second group after a sham operation. Although tumors from 500 mm$^3$ to 3000 mm$^3$ inhibited growth of metastases, 1500 mm$^3$ was the largest primary tumor that could be safely resected with high survival and no local recurrence.

After 21 days, all mice were sacrificed and autopsied. In mice with an intact primary tumor, there were four +2 visible metastases, compared to fifty +5 metastases in the mice in which the tumor had been removed ($p<0.0001$). These data were confirmed by lung weight, which correlates closely with tumor burden, as has been previously demonstrated. There was a 400% increase in wet lung weight in the mice that had their tumors removed compared to mice in which the tumor remained intact ($p<0.0001$).

This experimental model gave reproducible data and the experiment described is reproducible. This tumor is labeled "Lewis lung carcinoma—low metastatic" (LLC-Low). The tumor also suppressed metastases in a nearly identical pattern in SCID mice, which are deficient in both B and T lymphocytes.

Example 2

Isolation of a variant of Lewis lung carcinoma tumor that is highly metastatic, whether or not the primary tumor is removed.

A highly metastatic variant of Lewis lung carcinoma arose spontaneously from the LLC-Low cell line of Example 1 in one group of mice and has been isolated according to the methods described in Example 1 and repeatedly transplanted. This tumor (LLC-High) forms more than 30 visible lung metastases whether or not the primary tumor is present.

Example 3

Size of metastases and proliferation rate of tumor cells within them. Effect of the primary tumor that inhibits metastases (LLC-Low).

C57BI6/J mice were used in all experiments. Mice were inoculated subcutaneously with LLC-Low cells, and 14 days later the primary tumor was removed in half of the mice. At 5, 10 and 15 days after the tumor had been removed, mice were sacrificed. Histological sections of lung metastases were obtained. Mice with an intact primary tumor had micrometastases in the lung which were not neovascularized. These metastases were restricted to a diameter of 12–15 cell layers and did not show a significant size increase even 15 days after tumor removal. In contrast, animals from which the primary tumor was removed, revealed large vascularized metastases as early as 5 days after operation. These metastases underwent a further 4-fold increase in volume by the 15th day after the tumor was removed (as reflected by lung weight and histology). Approximately 50% of the animals who had a primary tumor removed died of lung metastases before the end of the experiment. All animals with an intact primary tumor survived to the end of the experiment.

Replication rate of tumor cells within metastases was determined by counting nuclei stained with BrdU which had been previously injected into the mice. The high percentage of tumor cells incorporating BrdU in small, avascular metastases of animals with an intact primary tumor was equivalent to the BrdU incorporation of tumor cells in the large vascularized metastases of mice from which the primary tumor had been removed (FIG. 3). This finding suggests that the presence of a primary tumor has no direct effect on the replication rate of tumor cells within a metastasis.

In FIG. 3, the left panel shows BrdU labeling index of tumor cells in the lung in the presence or absence of a primary tumor. Before immunohistochemical staining, sections were permeabilized with 0.2M HCl for 10 minutes and digested with 1 μg/ml proteinase K (Boehringer Mannheim GmbH, Mannheim, Germany) in 0.2M Tris-HCl, 2 mM CaCl$_2$ at 37° C. for 15 minutes. Labeling index was estimated by counting percentage of positive nuclei at 250 power. The right panel of FIG. 3 depicts an analysis of total lung weight of tumors with primary tumors intact or removed 5, 10 and 15 days after operation. Animals were sacrificed 6 hours after intraperitoneal injection of BrdU (0.75 mg/mouse).

Example 4

Inhibition of angiogenesis in lung metastases in the presence of an intact primary tumor.

To measure the degree of vascularization in lung metastases, tissues were stained with antibodies against von Willebrand factor (an endothelial specific marker, available from Dako Inc., Carpenteria, Calif.). Metastases from animals with intact tumors formed a thin cuff (8–12 tumor cell layers) around existing pulmonary vessels. Except for the endothelial cells of the vessel lining, no or few cells were positive for von Willebrand factor. In contrast, lung metastases of animals 5 days after removal of the primary tumor were not only larger but were also infiltrated with capillary sprouts containing endothelial cells which stained strongly for von Willebrand factor.

In immunohistochemical analysis of the presence of endothelial cells in lung metastases, a lung metastasis with the primary lung tumor intact 19 days after inoculation, had a cuff of tumor cells around a pre-existing microvessel in the lung. The metastasis was limited to 8 to 12 cell layers. There was no evidence of neovascularization around the microvessel, and it did not contain any new microvessels. This was typical of the maximum size of an avascular pre-angiogenic metastasis.

In an immunohistochemical analysis of tissue collected five days after the primary tumor was resected (19 days after inoculation of the primary tumor), the metastasis surrounded a pre-existing vessel in the lung. In contrast, in the sample where the primary tumor was not resected, the tumor was neovascularized. Thus, an intact primary tumor inhibits formation of new capillary blood vessels in metastases, but proliferation of tumor cells within a metastasis are not affected by the primary tumor.

Example 5

A primary tumor inhibits angiogenesis of a second tumor implanted in the mouse cornea. Growth of this second tumor is inhibited.

A 0.25 to 0.5 mm$^2$ Lewis lung tumor (LLC-Low) was implanted in the mouse cornea on day 0. (Muthukkaruppan Vr., et al., Angiogenesis in the mouse cornea. *Science* 205:1416–1418, 1979) A primary tumor was formed by inoculating 1×10⁶ LLC-Low cells subcutaneously in the dorsum, either 4 or 7 days before the corneal implant; or on the day of the corneal implant; or 4 or 7 days after the corneal implant. Control mice received the corneal implant but not the subcutaneous tumor. Other control mice received the corneal implant and an inoculation of LLC-High tumor cells in the dorsum 4 days before the cornea implant. The corneas were evaluated daily by slit-lamp stereomicroscopy for the growth of the corneal tumor (measured by an ocular micrometer) and for the growth of new capillary vessels from the edge of the corneal limbus.

In control mice not bearing a primary subcutaneous tumor, a majority of corneas (6/8) developed neovascularization starting at day 6 to 7 days after corneal implantation and continuing to day 10. By day 10, the vascularized corneal tumors had reached approximately a quarter of the volume of the whole eye. In the presence of the primary subcutaneous LLC-Low tumor, the corneal implants did not become vascularized if the primary tumor was in place by at least 4 days or more before the corneal implant (Table 1). In the absence of neovascularization, corneal tumors grew slowly as thin, white, avascular discs within the cornea.

However, if the primary tumor was not implanted until 4 days after the corneal implant, corneas became vascularized and 3/3 corneal tumors grew at similar rates as the non-tumor bearing controls. In the presence of the primary subcutaneous LLC-High tumor, the majority of corneas (2/3) developed neovascularization starting at day 7 after corneal implantation and continuing to day 10. By day 10, the vascularized corneal tumors again had reached approximately a quarter of the volume of the whole eye.

TABLE 1

Inhibition of tumor angiogenesis in the cornea by a primary subcutaneous tumor. [All primary tumors are LLC-Low except (*) which is LLC-High].

| Day of eye implant | 0 | 0 | 0 | 0 | 0 | 0 | 0 |
|---|---|---|---|---|---|---|---|
| Day of primary tumor implant | −7 | −4 | −4* | 0 | none | +4 | +7 |
| Number of mice with new corneal vessels at day 10 | 2/10 | 0/9 | 2/3 | 2/3 | 6/8 | 3/3 | 2/3 |

It would be expected that 0/10 corneas would show neovascularization when the primary LLC-Low subcutaneous tumor was implanted 7 days before the eye tumor implant (i.e.−7). However, 2 of the tumors (2/10) had become necrotic because they were too large (>3 cm³).

Example 6
Primary intact tumor inhibits angiogenesis induced by a secondary subcutaneous implant of basic fibroblast growth factor (bFGF.).

Although the experiments described in Examples V and VI show that a primary tumor inhibits angiogenesis in a secondary metastasis, these studies do not reveal whether the primary tumor: (i) inhibits endothelial proliferation (or angiogenesis) directly, or (ii) indirectly by down-regulating the angiogenic activity of the metastatic tumor cells. To distinguish between these two possibilities, a focus of subcutaneous angiogenesis was induced by an implant of matrigel containing basic fibroblast growth factor (bFGF). (Passaniti A, et al., A simple, quantitative method for assessing angiogenesis and anti-angiogenic agents using reconstituted basement membrane, heparin and fibroblast growth factor. *Lab. Invest.* 67:519, 1992)

Matrigel (an extract of basement membrane proteins), containing either 25 or 50 ng/ml bFGF in the presence of heparin, was injected subcutaneously on the ventral surface of normal and tumor-bearing mice (LLC-Low). Mice were sacrificed 4 days later and hemoglobin concentration in the gel was measured to quantify blood vessel formation. It has previously been shown that the number of new vessels which enter the matrigel is correlated with hemoglobin concentration. (Folkman J., Angiogenesis and its inhibitors in "*Important Advances in Oncology* 1985", VT DeVita, S. Hellman and S. Rosenberg, editors, J. B. Lippincott, Philadelphia 1985) Some gels were also prepared for histological examination. In normal mice, matrigel pellets which contained 50 ng/ml bFGF were completely red. They were heavily invaded by new capillary vessels, and contained 2.4 g/dl hemoglobin. Matrigel which lacked bFGF was translucent and gray and contained only 0.4 g/dl hemoglobin (a 6-fold difference). In contrast, matrigel from mice with a primary tumor contained only 0.5 g/dl (FIG. 4).

The near complete inhibition of angiogenesis in this experiment suggests that the presence of a Lewis lung primary tumor can inhibit bFGF-induced angiogenesis directly.

Example 7
Transfer of serum from a tumor-bearing animal to an animal from which the primary tumor has been removed suppresses metastases.

Mice were implanted with Lewis lung carcinoma as described above. After 15 days, when tumors were approximately 1500 mm³, the mice were randomized into four groups. Three groups underwent complete surgical resection of the primary tumor; in one group the tumors were left in place (after a sham surgical procedure). The mice in the three resection groups then received daily intraperitoneal injections of saline, serum from normal nontumor bearing mice, or serum from mice with 1500 mm³ Lewis lung carcinomas. The group of mice with the tumors left intact received intraperitoneal saline injections. All mice were treated for 21 days, after which the animals were euthanized and lung metastases were counted (Table 2).

TABLE 2

| | Primary Tumor Removed | | | Primary Tumor |
|---|---|---|---|---|
| Treatment (Intraperitoneal Injections) | Saline | Serum from normal mice | Serum from tumor-bearing mice | Intact Saline Injections |
| Number of Lung Metastases: | 55 ± 5 | 50 ± 4 | 7 ± 2 | 3± 1 |

These results were confirmed by lung weight. p=<0.0001 for the difference between the two groups [(55 & 50) vs. (7 & 3)]. Similar results have been obtained using angiostatin from the urine of tumor-bearing animals.

Example 8
Bovine capillary endothelial (BCE) cell assay

BCE cells are used between passages 9 and 14 only. At day 0, BCE cells are plated onto gelatinized (1.5% gelatin in PBS at 37°, 10% $CO_2$ for 24 hours and then rinsed with 0.5 ml PBS) 24 well plates at a concentration of 12,500 cells/well. Cell counts are performed using a hemocytometer. Cells are plated in 500 μl DMEM with 10% heat-inactivated (56° C. for 20 minutes) bovine calf serum and 1% glutamine-pen-strep (GPS).

BCE cells are challenged as follows: Media is removed and replaced with 250 μl of DMEM/5% BCS/1% GPS. The sample to be tested is then added to wells. (The amount varies depending on the sample being tested) Plates are placed at 37° C./10% $CO_2$ for approximately 10 minutes. 250 μl of DMEM/5% BCS/1% GPS with 2 ng/ml bFGF is added to each well. The final media is 500 μl of DMEM/5% BCS/1% GPS/with 1 ng/ml bFGF. The plate is returned to 37° C./10% $CO_2$ incubator for 72 hours.

At day 4, cells are counted by removing the medium and then trypsinizing all wells (0.5 ml trypsin/EDTA) for 2 to 3 minutes. The suspended cells are then transferred to scintillation vials with 9.5 ml Hemetall and counted using a Coulter counter. A unit of activity is that amount of serum containing angiostatin that is capable of producing half-maximal inhibition of capillary endothelial proliferation when endothelial cells are incubated in bFGF 1 ng/ml for 72 hours.

Example 9

Serum from mice bearing the low metastatic Lewis lung tumor (LLC-Low) inhibits capillary endothelial cell proliferation in vitro.

Bovine capillary endothelial cells were stimulated by basic fibroblast growth factor (bFGF 1 ng/ml), in a 72-hour proliferation assay. The serum of tumor-bearing mice added to these cultures inhibited endothelial cell proliferation in a dose-dependent and reversible manner. Normal serum was not inhibitory (FIG. 5). Endothelial cell proliferation was inhibited in a similar manner (relative to controls) by serum obtained from tumor-bearing nu/nu mice and SCID mice. After the primary tumor was removed, angiostatin activity disappeared from the serum by 3–5 days.

Tumor-bearing serum also inhibited bovine aortic endothelial cells and endothelial cells derived from a spontaneous mouse hemangioendothelioma, (Obeso, et al., "Methods in Laboratory Investigation, A Hemangioendothelioma-derived cell line; Its use as a Model for the Study of Endothelial Cell Biology," Lab Invest., 63(2), pgs 259–269, 1990) but did not inhibit Lewis lung tumor cells, 3T3 fibroblasts, aortic smooth muscle cells, mink lung epithelium, or W138 human fetal lung fibroblasts.

Example 10

Serum from mice bearing the Lewis lung tumor (LLC-High) that does not inhibit metastases, does not inhibit capillary endothelial cell proliferation in vitro.

Serum from mice bearing a primary tumor of the LLC-High did not significantly inhibit proliferation of bFGF-stimulated bovine capillary endothelial cells relative to controls. Also, when this serum was subjected to the first two steps of purification (heparin-Sepharose chromatography and gel filtration), angiostatin activity was not found in any fractions.

Example 11

Ascites from Lewis lung carcinoma (low metastatic), also generates angiostatin serum.

Mice received intraperitoneal injections of either LLC-Low or LLC-High tumor cells ($10^6$), and one week later, 1–2 ml of bloody ascites was obtained from each of 10–20 mice. Mesenteric tumor seeding was seen. The mice were then euthanized. Serum was obtained by cardiac puncture. Serum was also obtained from normal, non-tumor-bearing mice as a control. Serum and ascites were centrifuged to remove cells, and the supernate was assayed on bovine capillary endothelial cells stimulated by bFGF (1 ng/ml) (see Example IX). Ascites originating from both tumor types stimulated significant proliferation of capillary endothelial cells (e.g., 100% proliferation) over controls after 72 hours (FIG. 6). In contrast, serum from the low metastatic mice inhibited endothelial cell proliferation (inhibition to 79% of controls). The serum from the high metastatic line was stimulatory by 200%.

These data show that the ascites of the low metastatic line contains a predominance of endothelial growth stimulator over angiostatin. This condition is analogous to a solid primary tumor. Furthermore, angiostatin activity appears in the serum, as though it were unopposed by stimulatory activity. This pattern is similar to the solid primary tumor (LLC-Low). The ascites from the high metastatic tumor (LLC-High) also appears to contain a predominance of endothelial cell stimulator, but angiostatin cannot be identified in the serum.

Example 12

Fractionation of angiostatin from serum by column chromatography and analysis of growth-inhibitory fractions by SDS-PAGE.

To purify the angiostatin(s), serum was pooled from tumor-bearing mice. The inhibitory activity, assayed according the above-described in vitro inhibitor activity assay, was sequentially chromatographed using heparin-Sepharose, Biogel AO.5 mm agarose, and several cycles of C4-reverse phase high performance liquid chromatography (HPLC). SDS-PAGE of the HPLC fraction which contained endothelial inhibitory activity, revealed a discrete band of apparent reduced $M_r$ Of 38,000 Daltons, which was purified approximately 1 million-fold (see Table 3) to a specific activity of approximately $2\times10^7$. At different stages of the purification, pooled fractions were tested with specific antibodies for the presence of known endothelial inhibitors. Platelet factor-4, thrombospondin, or transforming growth factor beta, were not found in the partially purified or purified fractions.

TABLE 3

|  | Specific activity (units*/mg) | Fold purification |
| --- | --- | --- |
| Serum | 1.69 | 1 |
| Heparin Sepharose | 14.92 | 8.8 |
| Bio-gel AO.5m | 69.96 | 41.4 |
| HPLC/C4 | $2 \times 10^7$ | $1.2 \times 10^6$ |

*A unit of activity is that amount of serum containing angiostatin that is capable of producing half-maximal inhibition of capillary endothelial proliferation when endothelial cells are incubated in bFGF 1 ng/ml for 72 hours.

Example 13

Fractionation of angiostatin from urine by column chromatography and analysis of growth-inhibitory fractions by SDS-PAGE.

Purification of the endothelial cell inhibitor(s) from serum is hampered by the small volume of serum that can be obtained from each mouse and by the large amount of protein in the serum.

Urine from tumor bearing mice was analyzed and found that it contains an inhibitor of endothelial cell proliferation that is absent from the urine of non-tumor bearing mice and from mice with LLC-high tumors. Purification of the endothelial cell inhibitory activity was carried out by the same strategy that was employed for purification of serum (described above) (FIG. 7).

FIG. 7 shows C4 reverse phase chromatography of partially purified serum or urine from tumor-bearing animals.

All fractions were assayed on bovine capillary endothelial cells with bFGF in a 72-hour proliferation assay as described in Example IX. A discrete peak of inhibition was seen in both cases eluting at 30–35% acetonitrile in fraction 23. SDS-polyacrylamide gel electrophoresis of inhibitory fraction from the third cycle of C4 reverse phase chromatography of serum from tumor-bearing animals showed a single band at about 38,000 Daltons.

Example 14
Characterization of circulating angiostatin.

Endothelial inhibition was assayed according to the procedure described in Example 9. Angiostatin was isolated on a Synchropak HPLC C4 column. (Synchrom, Inc. Lafayette, Ind.) The inhibitor was eluted at 30 to 35% acetonitrile gradient. On a sodium dodecyl sulfate polyacrylamide gel electrophoresis (PAGE) gel under reducing conditions (b-mercaptoethanol(5% v/v), the protein band with activityeluted at 38 kilodaltons. Under non-reducing reducing conditions, the protein with activity eluted at 28 kilodaltons. The activity is found at similar points whether the initial sample was isolated from urine or from serum. Activity was not detected with any other bands.

Activity associated with the bands was lost when heated (100° C. for 10 minutes) or treated with trypsin. When the band with activity was extracted with a water/chloroform mixture (1:1), the activity was found in the aqueous phase only.

Example 15
Purification of inhibitory fragments from human plasminogen:

Plasminogen lysine binding site I was obtained from Sigma Chemical Company. The preparation is purified human plasminogen after digestion with elastase. Lysine binding site I obtained in this manner is a population of proteins that contain, in aggregate, at least the first three triple-loop structures (numbers 1 through 3) in the plasmin A-chain (Kringle 1+2+3). (Sotrrup-Jensen, L., et al. in *Progress in Chemical Fibrinolysis and Thrombolysis*, Vol. 3, 191, Davidson, J. F., et al. eds. Raven Press, N.Y. 1978 and Wiman, B., et al., *Biochemica et Biophysica Acta*, 579, 142 (1979)). Plasminogen lysine binding site I (Sigma Chemical Company, St. Louis, Mo.) was resuspended in water and applied to a C4-reversed phase column that had been equilibrated with HPLC-grade water/0.1% TFA. The column was eluted with a gradient of water/0.1% TFA to acetonitrile/ 0.1% TFA and fractions were collected into polypropylene tubes. An aliquot of each was evaporated in a speed vac, resuspended with water, and applied to BCEs in a proliferation assay. This procedure was repeated two times for the inhibitory fractions using a similar gradient for elution. The inhibitory activity eluted at 30–35% acetonitrile in the final run of the C4 column. SDS-PAGE of the inhibitory fraction revealed 3 discrete bands of apparent reduced molecular mass of 40, 42.5, and 45 kd. SDS-PAGE under non-reducing conditions revealed three bands of molecular mass 30, 32.5, and 35 kd respectively.

Example 16
Extraction of inhibitory activity from SDS-PAGE

Purified inhibitory fractions from human plasminogen based purifications were resolved by SDS-PAGE under non-denaturing conditions. Areas of the gel corresponding to bands seen in neighboring lanes loaded with the same samples by silver staining were cut from the gel and incubated in 1 ml of phosphate buffered saline at 4° C. for 12 hours in polypropylene tubes. The supernatant was removed and dialyzed twice against saline for 6 hours (MWCO= 6–8000) and twice against distilled water for 6 hours. The dialysate was evaporated by vacuum centrifugation. The product was resuspended in saline and applied to bovine capillary endothelial cells stimulated by 1 ng/ml basic fibroblast growth factor in a 72 hour assay. Protein extracted from each of the three bands inhibited the capillary endothelial cells.

Example 17
Plasminogen Fragment Treatment Studies

Mice were implanted with Lewis lung carcinomas and underwent resections when the tumors were 1500–2000 mm$^3$. On the day of operation, mice were randomized into 6 groups of 6 mice each. The mice received daily intraperitoneal injections with the three purified inhibitory fragments of human plasminogen, whole human plasminogen, urine from tumor-bearing animals, urine from normal mice, or saline. One group of tumor-bearing animals that had only a sham procedure was treated with saline injections. Immediately after removal of the primary tumor, the mice receive an intraperitoneal injection of 24 μg (1.2 mg/kg/day/mouse) of the inhibitory plasminogen fragments as a loading dose. They then receive a daily intraperitoneal injections of 12 μg of the inhibitory fragment (0.6 mg/kg/day/mouse) for the duration of the experiment. Control mice receive the same dose of the whole plasminogen molecule after tumor removal. For the urine treatments, the urine of normal or tumor bearing mice is filtered, dialyzed extensively, lyophilized, and then resuspended in sterile water to obtain a 250 fold concentration. The mice are given 0.8 ml of the dialyzed urine concentrate, either from tumor bearing mice or normal mice, in two intraperitoneal injections on the day of removal of the primary tumor as a loading dose. They then receive daily intraperitoneal injections of 0.4 ml of the dialyzed and concentrated urine for the course of the experiment. Treatments were continued for 13 days at which point all mice were sacrificed and autopsied.

The results of the experiment are shown in FIGS. 8 and 9. FIG. 8 shows surface lung metastases after the 13 day treatment. Surface lung metastases refers to the number of metastases seen in the lungs of the mice at autopsy. A stereomicroscope was used to count the metastases. FIG. 8 shows the mean number of surface lung metastases that was counted and the standard error of the mean. As shown, the group of mice with the primary tumor present showed no metastases. The mice in which the primary tumor was resected and were treated with saline showed extensive metastases. The mice treated with the human derived plasminogen fragment showed no metastases. The mice treated with whole plasminogen showed extensive metastases indicating that the whole plasminogen molecule has no endothelial inhibitory activity. Those mice treated with dialyzed and concentrated urine from tumor bearing mice showed no metastases. Mice treated with concentrated urine from normal mice showed extensive metastases. When the weight of the lung was measured, similar results were obtained (FIG. 9).

Example 18
Amino acid sequence of murine and human angiostatin.

The amino acid sequence of angiostatin isolated from mouse urine and angiostatin isolated from the human lysine binding site I fragment preparation was determined on an Applied Biosystem Model 477A protein sequencer. Phenylthiohydantoin amino acid fractions were identified with an on-line ABI Model 120A HPLC. The amino acid sequence determined from the N-terminal sequence and the tryptic digests of the murine and human angiostatin indicate that the sequence of the angiostatin is similar to the sequence beginning at amino acid number 98 of murine plasminogen. Thus, the amino acid sequence of the angiostatin is a molecule comprising a protein having a molecular weight of between approximately 38 kilodaltons and 45 kilodaltons as determined by reducing polyacrylamide gel electrophoresis and having an amino acid sequence substantially similar to that of a murine plasminogen fragment beginning at amino acid number 98 of an intact murine plasminogen molecule. The beginning amino acid sequence of the murine angiostatin (SEQ ID NO:2) is shown in FIG. 1. The length of the amino acid sequence may be slightly longer or shorter than that shown in the FIG. 1.

N terminal amino acid analysis and tryptic digests of the active fraction of human lysine binding site I (See Example 15) show that the sequence of the fraction begins at approximately amino acid 97 or 99 of human plasminogen and the human angiostatin is homologous with the murine angiostatin. The beginning amino acid sequence of the human angiostatin (starting at amino acid 98) is shown in FIG. 2, (SEQ ID NO:3). The amino acid sequence of murine and human angiostatin is compared in FIG. 2 to corresponding internal amino acid sequences from plasminogen of other species including porcine, bovine, and Rhesus monkey plasminogen, indicating the presence of angiostatin in those species.

Example 19
Expression of human angiostatin in E. coli.

The pTrcHisA vector (Invitrogen) (FIG. 10) was used to obtain high-level, regulated transcription from the trc promoter for enhanced translation efficiency of eukaryotic genes in E. coli. Angiostatin is expressed fused to an N-terminal nickel-binding poly-histidine tail for one-step purification using metal affinity resins. The enterokinase cleavage recognition site in the fusion protein allows for subsequent removal of the N-terminal histidine fusion protein from the purified recombinant protein. The recombinant human angioststin protein was found to bind lysine; is cross-reactive with monoclonal antibodies specific for kringle regions 1, 2 and 3, and inhibits bFGF-driven endothelial cell proliferation in vitro.

To construct the insert, the gene fragment encoding human angiostatin is obtained from human liver mRNA which is reverse transcribed and amplified using the polymerase chain reaction (PCR) and specific primers. The product of 1131 base pairs encodes amino acids 93 to 470 of human plasminogen. The amplified fragment was cloned into the XhoI/KpnI site of pTrcHisA, and the resultant construct transformed into XL-IB (available from Stratagene) E. coli host cells. A control clone containing the plasmid vector pTrcHisA alone was transformed inot XL-1B E. coli host cells as well. This clone is referred to as the vector control clone. Both clones were purified identically as described below.

Expressing colonies were selected in the following manner. Colony lifts of E. coli transformed with the gene encoding angiostatin were grown on IPTG impregnated nitrocellulose filters and overlaid on an LB agar plate. Following IPTG induction of expression, colonies were lysed on nitrocellulose filters. The nitrocellulose lifts were blocked, rinsed and probed with two separate monoclonal antibodies (mAbs Dcd and Vap; gift of S. G. McCance and F. J. Castellino, University of Notre Dame) which recognize specific conformations of angiostatin. Strongly expressing colonies recognized by the mAbs were selected.

To identify the optimal time for maximal expression, cells were collected at various times before and after IPTG induction and exposed to repeated freeze-thaw cycles, followed by analysis with SDS-PAGE, immunoblotting and probing with mAbs Dcd and Vap.

From these, clone pTrcHisA/HAsH4 was selected. Induction with IPTG was for 4 hours after which the cell pellet was collected and resuspended in 50 mM Tris pH 8.0, 2 mM EDTA, 5% glycerol and 200 mg/ml lysozyme and stirred for 30 min. at 40° C. The slurry was centrifuged at 14,000 rpm for 25 min. and the pellet resuspended in 50 mM Tris pH 8.0, 2 mM EDTA, 5% glycerol and 0.1% DOC. This suspension was stirred for 1 hr. at 40° C., and then centrifuged at 14,000 rpm for 25 min. The supernatant fraction at this step contains expressed angiostatin. The E. coli expressed human angiostatin was found to possess the physical property of native angiostatin, that is the ability to bind lysine. The E. coli expressed angiostatin was thus purified over a lysine-sepharose (Pharmacia or Sigma) column in a single step. Elution of angiostatin from the column was with 0.2M epsilon-amino-n-caproic acid pH7.5.

Subsequent to these experiments, scale-up 10 L fermentation batches of clone pTrcHisA/HAsH4 was performed. The cells obtained from this scaled-up induction were pelleted and resuspended in 50 mM Tris pH7.5, cracked at 10,000 psi thrice chilling at 10° C. in-between passes. The lysate obtained was clarified by centrifugation at 10,000 rpm for 30 min at 40° C., and expressed angiostatin isolated over lysine-sepharose (FIG. 11).

Purified E. coli expressed human angiostatin was dialysed exhaustively against water and lyophilized. The expressed human angiostatin was resuspended in media (DMEM, 5% BCS, 1% Gentamycin/penicillin/streptomycin) to an estimated concentration of 3 ug/ml, and used in bovine capillary endothelial (BCE) cell assays in vitro, as described in EXAMPLE 8, pg.39. Similarly, the control clone containing the vector alone was treated in the identical fashion as the clone pTrcHisA/HAsH4. It was induced with IPTG identically, and the bacterial lysate used to bind lysine, eluted with 0.2M amino caproic acid, dialysed exhaustively and lyophilized. This control preparation was resuspended in media also at an estimated concentration of 3 ug/ml. The samples of recombinant angiostatin, and controls were obtained from different induction and fermentation batches as well as seperate purification runs, and were all coded at EntreMed, Maryland. BCE assays were performed with these coded samples in a blinded fashion at Children's Hospital, Boston.

The results of BCE assays of recombinant human angiostatin showed that human angiostatin expressed in E.coli inhibited the proliferation of BCE cells due to bFGF (used at 1 ng/ml) (FIG. 12). The stock recombinant angiostatin in media (at about 3 ug/ml) was used at a 1:5, 1:10 and 1:20 dilution. Percent inhibition was calculated as follows:

$$1 - \frac{\text{number of cells with angiostatin} - \text{number of cells at day 0}}{\text{number of cells with } bFGF \text{ alone} - \text{number of cells at day 0}}$$

The percent inhibition of BCE cell proliferation was comparable or higher to that of plasminogen derived angiostatin at similar concentrations. The results from a repeat run of the BCE assay are depicted in FIG. 13, where at a 1:5 dilution of the stock, recombinant angiostatin gave similar percent inhibitions to those obtained with plasminogen derived angiostatin. FIG. 13 shows the surprising result that human recombinant angiostatin protein inhibits over 60%, and as much as over 75% of BCE proliferation in culture.

Example 20
Angiostatin maintains dormancy of micrometastases by increasing the rate of apoptosis.

Following subcutaneous inoculation of C57 BL6/J mice with Lewis lung carcinoma cells ($1\times10^6$), primary tumors of approximately 1.5 cm$^3$ developed. Animals were subject to either surgical removal of the primary tumor or sham surgery. At 5, 10 and 15 days after surgery, mice were sacrificed and their lungs prepared for histological examination. Animals with resected primary tumors showed massive proliferation of micrometastases compared to sham operated controls (FIG. 14). These changes were accompanied by a significant increase in lung weight.

Analysis of tumor cell proliferation, as measured by uptake of bromo-deoxyuridine (BrdU) showed no differences between animals with intact primary tumors or resected tumors at 5, 9 and 13 days, indicating that the increase in tumor mass could not be explained by increased proliferation (FIG. 15). Accordingly, cell death was examined in these animals. Apoptosis, a process of cell death that is dependent on changes in gene expression and accounts for elimination of cells during development and in rapidly proliferating tissues such as the small intestine, was examined by immunohistochemically labeling fragmented DNA with the terminal deoxynucleotidyl transferase (TdT) technique. The apoptotic index was determined at each time of sacrifice. The removal of primary tumors caused a statistically significant increase (approximately 3 to 4 fold) in the apoptotic index at all times examined (FIG. 15).

Supporting evidence was obtained by treating mice with removed primary tumors with an exogenous suppressor of angiogenesis. This substance, TNP-1470 (O-chloroacetylcarbamoyl fumagillol, previously named AGM-1470), is an analogue of fumagillin with reported anti-angiogenic activity. Subcutaneous injection of TNP-1470 (30 mg/kg every two days) produced results that were strikingly similar to those described above for animals that had intact primary tumors. These animals displayed a lower lung weight, equivalent proliferative index and increased apoptotic index compared to saline-injected controls (FIG. 16).

These data indicate that metastases remain dormant when tumor cell proliferation is balanced by an equivalent rate of cell death. The removal of the primary tumor causes a rapid increase in the growth of metastases, probably due to the removal of angiogenesis inhibitors (angiostatin) which control metastatic growth by increasing apoptosis in tumor cells. These effects are similar to those seen following removal of primary tumors and administration of an exogenous inhibitor of angiogenesis. Taken together, these data suggest that the primary tumor releases angiostatin which maintains dormancy of micrometastases.

Example 21
Treatment of primary tumors with angiostatin in vivo.

Angiostatin was purified from human plasminogen by limited elastase digestion as described in Example 15 above. Angiostatin was resuspended in phosphate-buffered saline for administration into six week old male C57Bl6/J mice. Animals were implanted subcutaneously with $1\times10^6$ tumor cells of either the Lewis lung carcinoma or T241 fibrosarcoma. Treatment with angiostatin is begun after four days when tumors are 80–160 mm$^3$ in size. Mice received angiostatin injections in either a single injection of 40 mg/kg or two 80 mg/kg injections via intraperitoneal (ip) or subcutaneous (sc) routes. Animals were sacrificed at various times after treatment extending to 19 days.

Angiostatin, administered at a daily dose of 40 mg/kg ip, produced a highly significant inhibition of the growth of T241 primary tumors (FIG. 17). This inhibitory effect on growth was visibly evident within 2 days and increased in magnitude throughout the time course of the study. By day 18, angiostatin-treated mice had tumors that were approximately 38% of the volume of the saline injected controls. This difference was statistically significant (p<0.001, Students t-test).

Angiostatin treatment (total dose of 80 mg/kg/day, administered twice daily at 40 mg/kg ip or sc) also significantly reduced the growth rate of LLC-LM primary tumors (FIG. 17). This inhibitory effect was evident at 4 days and increased in magnitude at all subsequent times examined. On the last day of the experiment (day 19), angiostatin-treated mice possessed a mean tumor volume that was only 20% of the saline-injected controls which was significantly different (p<0.001 Students t-test).

In another series of experiments angiostatin was administered (50 mg/kg q12h) to mice implanted with T241 fibrosarcoma, Lewis lung carcinoma (LM) or reticulum cell sarcoma cells. For each tumor cell type, the mice receiving angiostatin had substantially reduced tumor size. FIG. 19 demonstrates that for T241 fibrosarcoma, the angiostatin treated mice had mean tumor volumes that were only 15% of the untreated mice at day 24. FIG. 20 demonstrates that for Lewis lung carcinoma (LM), the angiostatin treated mice had mean tumor volumes that were only 13% of the untreated mice at day 24. FIG. 21 demonstrates that for reticulum sacroma, the angiostatin treated mice had mean tumor volumes that were only 19% of the untreated mice at day 24. The data represent the average of 4 mice at each time point.

These results demonstrate that angiostatin is an extremely potent inhibitor of the growth of three different primary tumors in vivo.

Example 22
Treatment of human cell-derived primary tumors in mice with angiostatin in vivo.

The effect of angiostatin on two human tumor cell lines, human prostate carcinoma PC-3 and human breast carcinoma MDA-MB, was studied. Immunodeficient SCID mice were implanted with human tumor cells, and the mice treated with 50 mg/kg angiostatin every 12 hours essentially as described in Example 21. The results demonstrate that the angiostatin protein of the present invention is a potent inhibitor of human tumor cell growth. FIG. 22 shows that for human prostate carcinoma PC-3, the angiostatin treated mice had only 2% of the mean tumor volume compared to the untreated control mice at day 24. FIG. 23 shows that for human breast carcinoma MDA-MB, he angiostatin treated mice had only 8% of the mean tumor volume compared to the untreated control mice at day 24.

Example 23
Gene Therapy—Effect of transfection of the angiostatin gene on tumor volume.

A 1380 base pair DNA sequence for angiostatin derived from mouse plasminogen cDNA (obtained from American Type Culture Collection (ATCC)), coding for mouse plasminogen amino acids 1–460, was generated using PCR and inserted into an expression vector. The expression vector was transfected into T241 fibrosarcoma cells and the transfected cells were implanted into mice. Control mice received either non-transfected T241 cells, or T241 cells transfected with the vector only (i.e. non-angiostatin expressing transfected cells). Three angiostatin-expressing transfected cell clones were used in the experiment. Mean tumor volume determined over time. The results show the surprising and dramatic reduction in mean tumor volume in mice for the angiostatin-expressing cells clones as compared with the non-transfected and non-expressing control cells.

The mouse DNA sequence coding for mouse angiostatin protein is derived from mouse plasminogen cDNA. The mouse angiostatin encompasses mouse plasminogen kringle regions 1–4. The schematic for constructing this clone is shown in FIG. 24.

The mouse angiostatin protein clones were transfected into T241 fibrosarcoma cells using the LIPOFECTIN™ transfection system (available from Life Technologies, Gaithersburg, Md.). The LIPOFECTIN™ reagent is a 1:1 (w/w) liposome formulation of the cationic lipid N-[1-(2,3-dioleyloxy)propyl]-n,n,n-trimethylammonium chloride (DOTMA), and diolecoyl phosphotidylethanolamine (DOPE) in membrane filtered water.

The procedure for transient transfection of cells is as follows:
1. T241 cells are grown in 60 cm² tissue culture dishes, seed ≈1–2×10⁵ cells in 2 ml of the appropriate growth medium supplemented with serum.
2. Incubate the cells at 37° C. in a $CO_2$ incubator until the cells are 40–70% confluent. will usually take 18–24 h, but the time will vary among cell types. The T241 tumor cells confluency was approximately 70%.
3. Prepare the following solutions in 12×75 mm sterile tubes: Solution A: For each transfection, dilute 5 μg of DNA in 100 μl of serum-free OPTI-MEM I Reduced Serum Medium (available from Life Technologies) (tissue culture grade deionized water can also be used). Solution B: For each transfection, dilute 30 μg of LIPOFECTIN in 100 μl OPTI-MEM medium.
4. Combine the two solutions, mix gently, and incubate at room temperature for 10–15 min.
5. Wash cells twice with serum-free medium.
6. For each transfection, add 0.8 ml serum-free medium to each tube containing the LIPOFECTIN™ reagent-DNA complexes. Mix gently and overlay the complex onto cells.
7. Incubate the cells for approximately 12 h at 37° C. in a $CO_2$ incubator.
8. Replace the DNA containing medium with 1 mg/ml selection medium containing serum and incubate cells at 37° C. in a $CO_2$ incubator for a total of 48–72 h.
9. Assay cell extracts for gene activity at 48–72 h post transfection.

Transfected cells can be assayed for expression of angiostatin protein using angiostatin-specific antibodies. Alternatively, after about 10–14 days, G418 resistant colonies appeared in the CMV-angiostatin transfected T241 cells. Also, a number of clones were seen in the vector alone transfected clones but not in the untransfected clones. The G418 resistant clones were selected for their expression of angiostatin, using a immunofluorence method.

Interestingly, the in vitro cell growth T241 cells and Lewis lung cells transfected with angiostatin was not inhibited or otherwise adversely affected, as shown in FIGS. 25 and 26.

FIG. 27 depicts the results of the transfection experiment. All three of the angiostatin-expressing T241 transfected clones produced mean tumor volumes in mice that were substantially reduced relative to the tumor volume in contol mice. The mean tumor volume of the mice implanted with Clone 37 was only 13% of the control, while Clone 31 and Clone 25 tumor volumes were only 21% and 34% of the control tumor volumes, respectively. These results demonstrate that the DNA sequences coding for angiostatin can be transfected into cells, that the transfected DNA sequences are capable of expressing angiostatin protein by implanted cells, and that the expressed angiostatin fucntions in vivo to reduce tumor growth.

Example 24

Localization of in vivo site of angiostatin expression

To localize the in vivo site of expression of angiostatin protein, total RNA from various cell types, Lewis lung carcinoma cells (mouse), T241 fibrosarcoma (mouse), and Burkitt's lymphoma cells (human), both from fresh tumor or cell culture after several passages were analysed to determine the presence of angiostatin transcripts. Northern analysis of samples showed an absence of any signal hybridizing with thn sequence from all samples except that of normal mouse liver RNA showing a single signal of approximately 2.4 kb corresponding to mouse plasminogen. Northern analysis of human samles show an absence of any signal hybridizing with human angiostatin sequence from all samples except that of normal human liver RNA showing a single signal of approximately 2.4 kb corresponding to human plasminogen.

Reverse transcription polymerase chain reaction (RT-PCR) analysis showed an absence of any product from all samples probed with mouse angiostatin sequences except that of the normal mouse liver. RT-PCR analysis showed an absence of any product from all human samples probed with human angiostatin sequences except that of the normal human liver (expected size of 1050 bp for mouse and 1134 bp for human).

Thus it appears that mouse angiostatin transcripts (assuming identity with amino acids 97 to 450 of mouse plasminogen) are not produced by all the above mouse samples and human angiostatin transcripts (assuming identity with amino acids 93 to 470 of human plasminogen) are not produced by the above human samples. The positive signals obtained in normal mouse/human liver is from hybridization with plasminogen.

Example 25

Expression of Angiostatin in Yeast

The gene fragment encoding amino acids 93 to 470 of human plasminogen was cloned into the XhoI/EcoRI site of pHIL-SI(Invitrogen) which allows the secreted expression of proteins using the PHO1 secretion signal in the yeast *Pichia pastoris*. Similarly, the gene fragment encoding amino acids 93 to 470 of human plasminogen was cloned into the SnaBI/EcoRI site of pPIC9 (Invitrogen) which allows the secreted expression of proteins using the a-factor secretion signal in the yeast *Pichia pastoris*. The expressed human angiostatin proteins in these systems will have many advantages over those expressed in *E. coli* such as protein processing, protein folding and posttranslational modification inclusive of glycosylation.

Expression of gene in *P. pastoris*: is described in) Sreekrishna, K. et al. (1988) High level expression of heterologous proteins in methylotropic yeast *Pichia pastoris*. J. Basic Microbiol. 29 (4): 265–278, and Clare, J. J. et al. (1991) Production of epidermal growth factor in yeast: High-level secretion using *Pichia pastoris* strains containing multiple gene copies, Gene 105:205–212, both of which are hereby incorporated herein by reference.

Example 26

Expression of angiostatin proteins in transgenic animals and plants

Transgenic animals such as of the bovine or procine family are created which express the angiostatin gene transcript. The transgenic animal express angiostatin protein for example in the milk of these animals. Additionally edible transgenic plants which express the angiostatin gene transcript are constructed.

Constructing transgenic animals that express foreign DNA is described in Smith H. Phytochrome transgenics: functional, ecological and biotechnical applications, Semin. Cell. Biol. 1994 5(5):315–325, which is hereby incorporated herein by reference.

Example 27
Characterization of Endothelial Cell Proliferation Inhibiting Angiostatin Fragments The following example characterizes the activity of individual and combinational angiostatin fragments. The data suggests that a functional difference exists among individual kringle structures, and potent anti-endothelial, and hence anti-angiogenic, activity can be obtained from such protein fragments of angiostatin.

As used herein, "angiostatin fragment" means a protein derivative of angiostain, or plasminogen, having an endothelial cell proliferation inhibiting activity. Angiostatin fragments are useful for treating angiogenic-mediated diseases or conditions. For example, angiostatin fragments can be used to inhibit or suppress tumor growth. The amino acid sequence of such an angiostatin fragment, for example, can be selected from a portion of murine plasminogen (SEQ ID NO:1), murine angiostatin (SEQ ID NO:2); human angiostatin (SEQ ID NO:3), Rhesus angiostatin (SEQ ID NO:4), porcine angiostatin (SEQ ID NO:5), and bovine angiostatin (SEQ ID NO:6), unless indicated otherwise by the context in which it is used.

As used herein, "kringle 1" means a protein derivative of plasminogen having an endothelial cell inhibiting activity or anti-angiogenic activity, and having an amino acid sequence comprising a sequence homologous to kringle 1, exemplified by, but not limited to that of murine kringle 1 (SEQ ID NO:7), human kringle 1 (SEQ ID NO:8), Rhesus kringle 1 (SEQ ID NO:9), porcine kringle 1 (SEQ ID NO:10), and bovine kringle 1 (SEQ ID NO: 11), unless indicated otherwise by the context in which it is used. Murine kringle 1 (SEQ ID NO:7) corresponds to amino acid positions 103 to 181 (inclusive) of murine plasminogen of SEQ ID NO:1, and corresponds to amino acid positions 6 to 84 (inclusive) of murine angiostatin of SEQ ID NO:2. Human kringle 1 (SEQ ID NO:8), Rhesus kringle 1 (SEQ ID NO:9), porcine kringle 1 (SEQ ID NO:10), and bovine kringle 1 (SEQ ID NO:11) correspond to amino acid positions 6 to 84 (inclusive) of angiostatin of SEQ ID NO:3, SEQ ID NO:4, SEQ ID NO:5, and SEQ ID NO:6, respectively.

As used herein, "kringle 2" means a protein derivative of plasminogen having an endothelial cell inhibiting activity or anti-angiogenic activity, and having an amino acid sequence comprising a sequence homologous to kringle 2, exemplified by, but not limited to that of murine kringle 2 (SEQ ID NO:12), human kringle 2 (SEQ ID NO:13), Rhesus kringle 2 (SEQ ID NO:14), porcine kringle 2 (SEQ ID NO:15), and bovine kringle 2 (SEQ ID NO:16), unless indicated otherwise by the context in which it is used. Murine kringle 2 (SEQ ID NO:12) corresponds to amino acid positions 185 to 262 (inclusive) of murine plasminogen of SEQ ID NO:1, and corresponds to amino acid positions 88 to 165 (inclusive) of murine angiostatin of SEQ ID NO:2. Human kringle 2 (SEQ ID NO:13), Rhesus kringle 2 (SEQ ID NO:14), porcine kringle 2 (SEQ ID NO:15), and bovine kringle 2 (SEQ ID NO: 16) correspond to amino acid positions 88 to 165 (inclusive) of angiostatin of SEQ ID NO:3, SEQ ID NO:4, SEQ ID NO:5, and SEQ ID NO:6, respectively.

As used herein, "kringle 3" means a protein derivative of plasminogen having an endothelial cell inhibiting activity or anti-angiogenic activity, and having an amino acid sequence comprising a sequence homologous to kringle 3, exemplified by, but not limited to that of murine kringle 3 (SEQ ID NO:17), human kringle 3 (SEQ ID NO:18), Rhesus kringle 3 (SEQ ID NO:19), porcine kringle 3 (SEQ ID NO:20), and bovine kringle 3 (SEQ ID NO:21). Murine kringle 3 (SEQ ID NO:17) corresponds to amino acid positions 275 to 352 (inclusive) of murine plasminogen of SEQ ID NO:1, and corresponds to amino acid positions 178 to 255 (inclusive) of murine angiostatin of SEQ ID NO:2. Human kringle 3 (SEQ ID NO:18), Rhesus kringle 3 (SEQ ID NO:19), porcine kringle 3 (SEQ ID NO:20), and bovine kringle 3 (SEQ ID NO:21) correspond to amino acid positions 178 to 255 (inclusive) of angiostatin of SEQ ID NO:3, SEQ ID NO:4, SEQ ID NO:5, and SEQ ID NO:6, respectively.

As used herein, "kringle 4" means a protein derivative of plasminogen having an endothelial cell inhibiting activity or anti-angiogenic activity, and having an amino acid sequence comprising a sequence homologous to kringle 4, exemplified by, but not limited to that of murine kringle 4 (SEQ ID NO:22) and human kringle 4 (SEQ ID NO:23), unless indicated otherwise by the context in which it is used. Murine kringle 4 (SEQ ID NO:22) corresponds to amino acid positions 377 to 454 (inclusive) of murine plasminogen of SEQ ID NO: 1.

As used herein, "kringle 2–3" means a protein derivative of plasminogen having an endothelial cell inhibiting activity or anti-angiogenic activity, and having an amino acid sequence comprising a sequence homologous to kringle 2–3, exemplified by, but not limited to that of murine kringle 2–3 (SEQ ID NO:24), human kringle 2–3 (SEQ ID NO:25), Rhesus kringle 2–3 (SEQ ID NO:26), porcine kringle 2–3 (SEQ ID NO:27), and bovine kringle 2–3 (SEQ ID NO:28), unless indicated otherwise by the context in which it is used. Murine kringle 2–3 (SEQ ID NO:24) corresponds to amino acid positions 185 to 352 (inclusive) of murine plasminogen of SEQ ID NO:1, and corresponds to amino acid positions 88 to 255 (inclusive) of murine angiostatin of SEQ ID NO:2. Human kringle 2–3 (SEQ ID NO:25), Rhesus kringle 2–3 (SEQ ID NO:26), porcine kringle 2–3 (SEQ ID NO:27), and bovine kringle 2–3 (SEQ ID NO:28) correspond to amino acid positions 88 to 255 (inclusive) of angiostatin of SEQ ID NO:3, SEQ ID NO:4, SEQ ID NO:5, and SEQ ID NO:6, respectively.

As used herein, "kringle 1–3" means a protein derivative of plasminogen having an endothelial cell inhibiting activity or anti-angiogenic activity, and having an amino acid sequence comprising a sequence homologous to kringle 1–3, exemplified by, but not limited to that of murine kringle 1–3 (SEQ ID NO:29), human kringle 1 (SEQ ID NO:30), Rhesus kringle 1–3 (SEQ ID NO:31), porcine kringle 1–3 (SEQ ID NO:32), and bovine kringle 1–3 (SEQ ID NO:33), unless indicated otherwise by the context in which it is used. Murine kringle 1–3 (SEQ ID NO:29) corresponds to amino acid positions 103 to 352 (inclusive) of murine plasminogen of SEQ ID NO:1, and corresponds to amino acid positions 6 to 255 (inclusive) of murine angiostatin of SEQ ID NO:2. Human kringle 1–3 (SEQ ID NO:30), Rhesus kringle 1–3 (SEQ ID NO:31), porcine kringle 1–3 (SEQ ID NO:32), and bovine kringle 1–3 (SEQ ID NO:33) correspond to amino acid positions 6 to 255 (inclusive) of angiostatin of SEQ ID NO:3, SEQ ID NO:4, SEQ ID NO:5, and SEQ ID NO:6, respectively.

As used herein, "kringle 1–2" means a protein derivative of plasminogen having an endothelial cell inhibiting activity or anti-angiogenic activity, and having an amino acid sequence comprising a sequence homologous to kringle 1–2, exemplified by, but not limited to that of murine kringle 1–2 (SEQ ID NO:34), human kringle 1–2 (SEQ ID NO:35), Rhesus kringle 1–2 (SEQ ID NO:36), porcine kringle 1–2 (SEQ ID NO:37), and bovine kringle 1–2 (SEQ ID NO:38), unless indicated otherwise by the context in which it is used. Murine kringle 1–2 (SEQ ID NO:34) corresponds to amino acid positions 103 to 262 (inclusive) of murine plasminogen of SEQ ID NO:1, and corresponds to amino acid positions 6 to 165 (inclusive) of murine angiostatin of SEQ ID NO:2. Human kringle 1–2 (SEQ ID NO:35), Rhesus kringle 1–2 (SEQ ID NO:36), porcine kringle 1–2 (SEQ ID NO:37), and bovine kringle 1–2 (SEQ ID NO:38) correspond to amino acid positions 6 to 165 (inclusive) of angiostatin of SEQ ID NO:3, SEQ ID NO:4, SEQ ID NO:5, and SEQ ID NO:6, respectively.

As used herein, "kringle 1–4" means a protein derivative of plasminogen having an endothelial cell inhibiting activity or anti-angiogenic activity, and having an amino acid sequence comprising a sequence homologous to kringle 1–4, exemplified by, but not limited to that of murine kringle 1–4 (SEQ ID NO:39) and human kringle 1–4 (SEQ ID NO:40), unless indicated otherwise by the context in which it is used. Murine kringle 1–4 (SEQ ID NO:39) corresponds to amino acid positions 103 to 454 (inclusive) of murine plasminogen of SEQ ID NO: 1.

Kringle 1, kringle 2, kringle 3, kringle 4, kringle 2–3, kringle 1–3, kringle 1–2 and kringle 1–4 amino acid sequences are respectively homologous to the specific kringle sequences identified above. Preferably, the amino acid sequences have a degree of homology to the disclosed sequences of at least 60%, more preferably at least 70%, and more preferably at least 80%. It should be understood that a variety of amino acid substitutions, additions, deletions or other modifications to the above listed fragments may be made to improve or modify the endothelial cell proliferation inhibiting activity or anti-angiogenic activity of the angiostatin fragments. Such modifications are not intended to exceed the scope and spirit of the claims. For example, to avoid homodimerization by formation of inter-kringle disulfide bridges, the cysteine residues C4 in recombinant human kringle 2 (SEQ ID NO:13) and C42 in recombinant kringle 3 (SEQ ID NO:18) were mutated to serines. Furthermore, it is understood that a variety of amino acid substitutions, additions, deletions or other modifications can be made in the above identified angiostatin fragments, which do not significantly alter the fragments' endothelial cell proliferation inhibiting activity, and which are, therefore, not intended to exceed the scope of the claims. By "not significantly alter" is meant that the angiostatin fragment has at least 60%, more preferably at least 70%, and more preferably at least 80% of the endothelial cell proliferation inhibiting activity compared to that of the closest homologous angiostatin fragment disclosed herein.

Gene Construction and Expression

A PCR-based method was used to generate the cDNA fragments coding for kringle 1 (K1), kringle 2 (K2), kringle 3 (K3), kringle 4 (K4) and kringle 2–3 (K2–3) of human plasminogen (HPg). Recombinant kringle 1 (rK1), kringle 2 (rK2), kringle 3 (rK3), kringle 4 (rK4) and kringle 2–3 (rK2–3) 3) were expressed in *E. coli* as previously described (Menhart, N., Shel, L. C., Kelly, R. F., and Castellino, F. J. (1991) *Biochem.* 30, 1948–1957; Marti, D., Schaller, J., Ochensberger, B., and Rickli, E. E. (1994) *Eur. J. Biochem.* 219, 455–462; Söhndel, S., Hu, C.-K., Marti, D., Affolter, M., Schaller, J., Llinas, M., and Rickli, E. E. (1996) *Biochem.*, in press; Rejante, M. R., Byeon, I.-J. L., and Llinas, M. (1991) *Biochem.* 30, 11081–11092). To avoid homodimerization by formation of inter-kringle disulfide bridges as shown in FIG. 32B, the cysteine residues C169 and rK2 and C297 in rK3 were mutated to serines as seen in SEQ ID NO.s 13 and 18, at positions 4 and 42, respectively. (Söhndel, S., Hu, C.-K., Marti, D., Affolter, M., Schaller, J., Llinas, M., and Rickli, E. E. (1996) *Biochem.* in press). The rK3 and rK2–3 contained an N-terminal hexa-histidine tag which was used for protein purification (not shown).

Proteolytic Digestion

The fragments of K1–3, K1–4 and K4 were prepared by digestion of Lys-HPg (Abbott Labs) with porcine elastase (Sigma) as previously described (Powell, J. R., and Castellino, F. J. (1983) *Biochem.* 22, 923–927). Briefly, 1.5 mg elastase was incubated at room temperature with 200 mg of human plasminogen in 50 mM Tris-HCl pH 8.0 overnight with shaking. The reaction was terminated by the addition of diisopropyl fluorophosphate (DFP) (Sigma) to a final concentration of 1 mM. The mixture was rocked for an additional 30 minutes at room temperature and dialyzed overnight against 50 mM Tris-HCl, pH 8.0.

Protein Purification

Recombinant K1 was expressed in DH5α *E. coli* bacterial cells using a pSTII plasmid vector. This protein was purified to homogeneity by chromatography using lysine-Sepharose 4B (Pharmacia) and Mono Q (BioRad) columns. *E. coli* bacterial cells (strain HB101) expressing rK2 and rK3 were grown to an $OD_{600}$ of approximately 0.8 at 3° C. in 2× YT medium containing 100 mg/ml ampicillin and 25 mg/ml kanamycin. IPTG (isopropyl-b-D-thiogalactopyranoside) was added to a final concentration of 1 mM and cells were grown for an additional 4.5 hours at 37° C. to induce the production of recombinant proteins. The cells were harvested by centrifugation and the pellets were stored at −80° C. The thawed cell lysates were re-suspended in the extraction buffer (6M guanidine hydrochloride in 0.1M sodium phosphate, pH 8.0). The suspension was centrifuged at 15,000×g for 30 minutes and b-mercaptoethanol was added to the supernatant at a final concentration of 10 mM. The supernatant was then loaded on a $Ni^{2+}$-NTA agarose column (1.5 cm×5 cm) pre-equilibrated with the extraction buffer. The column was washed successively with extraction buffer at pH 8.0 and pH 6.3, respectively. Recombinant K2 and K3 were eluted with extraction buffer at pH 50.

The proteolytically cleaved fragments of K1–3, K1–4 and K4 were purified using a lysine-Sepharose 4B column (2.5 cm×15 cm) equilibrated with 50 mM Tris-HCl, pH 8.0 until an absorbance at 180 nm reached 0.005. The absorbed kringle fragments were eluted with Tris buffer containing 200 mM ε-aminocaproic acid, pH 8.0. The eluted samples were the dialyzed overnight against 20 mM Tris-HCl, pH 5.0, and were applied to a BioRad Mono-S column equilibrated with the same buffer. The fragments of K4, K1–3 and K1–4 were eluted with 0–20%, 20–50% and 50–70% step-gradients of 20 mM phosphate/1M KCl, pH 5.0. Most K1–3 and K1–4 fragments were eluted from the column with 0.5M KCl as determined by SDS-PAGE. All fractions were dialyzed overnight against 20 mM Tris-HCl, pH 8.0. After dialysis, K1–3 and K1–4 fragments were further purified using a heparin-Sepharose column (5 cm×10 cm) (Sigma) pre-equilibrated with 20 mM Tris-HCl buffer, pH 8.0. The K1–3 fragment was eluted with 350 mM KCl and K1–4 was recovered from the flow-through fraction. The purified kringle fragments were analyzed on SDS-gels follows by silver-staining, by Western immunoblotting analysis with anti-human K4 and K1–3 polyclonal antibodies, and by amino-terminal sequencing analysis.

In vitro re-folding

The re-folding of rK2, rK3 and rK2–3 was performed according to a standard protocol (Cleary, S., Mulkerrin, M. G., and Kelley, R. R. (1989) *Biochem.* 28, 1884–1891). The purified proteins were adjusted to pH 8.0 and dithiotreitol (DTT) was added to a final concentration of 5 mM. After an overnight incubation, the solution was diluted with 4 volumes of 50 mM Tris-HCl, pH 8.0, containing 1.25 mM reduced glutathione. After 1 hour of incubation, oxidized glutathione was added to a final concentration of 1.25 mM and incubated for 6 hours at 4° C. The renatured protein was dialyzed initially against $H_2O$ for 2 days and for an additional two days against 50 mM phosphate-buffered saline, pH 8.0. The solution was then loaded onto a lysine-Bio-Gel column (2 cm×13 cm) equilibrated with the same phosphate-buffered saline. The column was washed with phosphate-buffered saline and protein was eluted with a phosphate buffer containing 50 mM 6-AHA (6-aminohexanoic acid). Reverse-phase HPLC was performed on an Aquapore Butyl column (2.1×100 mm, widepore 30 nm, 7 mm, Applied Biosystems) and a Hewlett Packard liquid chromatography was used with acetonitrile gradients.

Reduction and Alkylation

The reduction and alkylation of kringle fragments were performed according to a standard protocol (Cao, Y., and Pettersson, R. F., (1990) *Growth Factors* 3, 1013). Approximately 20–80 mg of purified proteins in 300–500 ml DME medium in the absence of serum were incubated at room temperature with 15 ml of 0.5M DTT for 15 minutes. After incubation, 30 ml of 0.5M iodoacetamide was added to the reaction. The protein solution was dialyzed at 4° C. overnight initially against 20 volumes of DMEM. The solution was further dialyzed at 4° C. for an additional 4 hours against 20 volumes of fresh DMEM. After dialysis, the samples were analyzed on a SDS-gel and assayed for their inhibitory activities on endothelial cell proliferation.

Endothelial Proliferation Assay

Bovine capillary endothelial (BCE) cells were isolated as previously described (Folkman, J., Haudenschild, C. C., and Zetter, B. R. (1979) *Proc. Natl. Acad. Sci USA.* 76, 5217–5121) and maintained in DMEM supplemented with 10% heat-inactivated bovine calf serum (BCS), antibiotics, and 3 ng/ml recombinant human bFGF (Scios Nova, Mountainview, Calif.). Monolayers of BCE cells growing in 6-well plates were dispersed in a 0.05% trypsin solution. Cells were resuspended with DMEM containing 10% BCS. Approximately 12,500 cells in 0.5 ml were added to each well of gelatinized 24-well tissue culture plates and incubated at 37° C. (in 10% $CO_2$) for 24 hours. The medium was replaced with 500 ml of fresh DMEM containing 5% BCS and samples of individual or combinatorial kringle fragments in triplicates were added to each well. After 30 minutes of incubation, bFGF was added to a final concentration of 1 ng/ml. After 72 hours of incubation, cells were trypsinized, re-suspended in Hematall (Fisher Scientific, Pittsburg, Pa.) and counted with a Coulter counter.

Purification and Characterization of Kringle Fragment of Human Plasminogen

Figure 29:
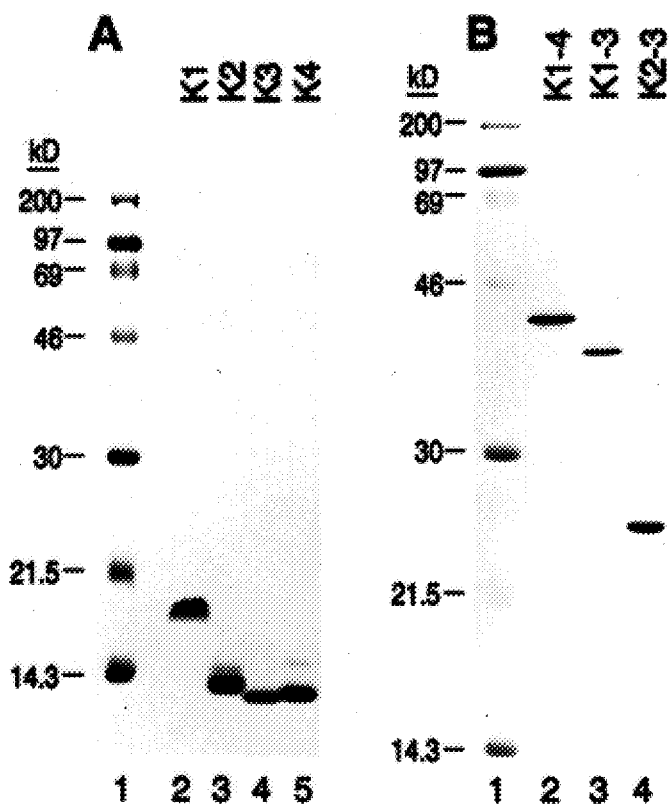

The cDNA fragments coding for individual kringles (K1, K2, K3, and K4) and kringles 2–3 (K2–3) of human plasminogen were amplified by a PCR-based method (FIG. 28). The PCR-amplified cDNA fragments were cloned into a bacterial expression vector. Recombinant proteins expressed from *Escherichia coli* were refolded in vitro and were purified to >98% homogeneity using HPLC-coupled chromatography (FIG. 29). Under reducing conditions, recombinant K2, K3 and K4 migrated with molecular weights of 12–13 kDa (FIG. 29A, lanes 2–4), corresponding to the predicted molecular weights of each kringle fragment. Recombinant K1 migrating with a higher molecular weight of 17 kDa was identified by SDS-gel electrophoresis. The fragments of K1–4 and K1–3 were obtained by proteolytic digestion of human Lys-plasminogen (Lys-HPg) with elastase as previously described (Powell, J. R., and Castellino, F. J. (1983) *Biochem.* 22, 923–927; Brockway, W. J., and Castellino, F. J. (1972) *Arch. Biochem. Biophys*). These two fragments (FIG. 29B, lanes 1 and 2) with predicted molecular weights of 43 kDa and 35 kDa, respectively, were also purified to homogeneity. N-terminal amino acid sequence analysis of the purified fragments yielded an identical sequence, -YLSE-, followed by SEQ ID NO:30 and SEQ ID NO:40, for K1–3 and K1–4, respectively. The N-terminal sequence for K4 produced -VVQD- with approximately 20% -VQD-, followed by SEQ ID NO:23, each of which is predicted from the expected sequence beginning with Valine[176] and Valinel[177] of human angiostatin (SEQ ID NO: 3).

Anti-Endothelial Cell Proliferative Activity of Individual Kringles

Individual recombinant kringle fragments of angiostatin were assayed for the inhibitory activities on bovine capillary endothelial (BCE) cell growth stimulated by bFGF. As shown in FIG. 30A, rKl inhibited BCE cell proliferation in a dose-dependent fashion. The concentration of rK1 required to reach 50% inhibition ($ED_{50}$) was about 320 nM (Table 4). In contrast, rK4 exhibited little or no inhibitory effect on endothelial cell proliferation. Recombinant K2 and rK3, two non-lysine binding kringle fragments, also produced a dose-dependent inhibition of endothelial cell proliferation (FIG. 30B). However, the inhibitory potency of rK2 was substantially lower than rK1 and rK3 ($ED_{50}$=460) (FIG. 30 and Table 4). No cytotoxicity or distinct morphology associated with apoptotic endothelial cells such as rounding, detachment, and fragmentation of cells could be detected, even after incubation with a high concentration of these kringle fragments. These data suggest that the anti-endothelial growth activity of angiostatin may be shared by fragments of K1, K2 and K3, and lesser so by K4.

TABLE 4

Inhibitory activity on capillary endothelial cell proliferation.

| Fragments | $ED_{50}$(nM) |
|---|---|
| Kringle 1 | 320 |
| Kringle 2 | — |
| Kringle 3 | 460 |
| Kringle 4 | — |
| Kringle 2–3 | — |
| Kringle 1–3 | 70 |
| Kringle 1–4 (Angiostantin) | 135 |

Anti-Endothelial Cell Proliferative Activity of K1–3 and K1–4 Fragments

To evaluate the anti-endothelial cell proliferative effect of combined kringle fragments, purified proteolytic fragments of human K1–4 , K1–3 and rK2–3 were assayed on BCE cells. In agreement with previous findings (O'Reilly, M. S., Holmgren, L., Shing, Y., Chen, C., Rosenthal, R. A., Moses, J., Lane, W. S., Cao, Y., Sage, E. H., and Folkman, J. (1994) *Cell* 79, 315–328), BCE cell proliferation, as shown in FIG. 31, was significantly inhibited by angiostatin-like fragment K1–4 ($ED_{50}$=135 nM) (Table 4). An increase of anti-endothelial growth activity was obtained with K1–3 fragment (ED$_{50}$=70 nM) (Table 4). The inhibition of endothelial cell proliferation occurred in a dose-dependent manner. These results indicate that removal of K4 from angiostatin potentiates anti-endothelial growth activity.

Additive Inhibition by rK2 and rK3

The fragment of rK2–3 displayed only weak inhibitory activity which was similar to that of rK2 alone (FIG. 31). However, both rK2 and rK3 inhibited endothelial cell proliferation (FIG. 30B). This finding suggested that the inhibitory effect of K3 was hidden in the structure of K2–3. Previous structural studies showed that an inter-kringle disulfide bond was present between K2 (cysteine$^{169}$) and K3 (cysteine$^{297}$) of human plasminogen, corresponding to cysteine$^{91}$ and cysteine$^{219}$ of SEQ ID NO: 3 (Sóhndel, S., Hu, C.-K., Marti, D., Affolter, M., Schaller, J., Llinas, M., and Rickli, E. E. (1996) *Biochem.* in press) See FIG. 32B. The inhibitory effect of rK2 and rK3 in combination was tested. Interestingly, an additive inhibition was seen when individual rK2 and rK3 fragments were added together to BCE cells. See FIG. 32A. These results imply that it is preferable to open the interdisulfide bridge between K2 and K3 in order to obtain the maximal inhibitory effect of K2–3.

Appropriate Folding of Kringle Structures is Required for the Anti-Endothelial Activity of Angiostatin To study whether the folding of kringle structures is required for the anti-endothelial proliferation activity, native angiostatin was reduced with DTT and assayed on bovine capillary endothelial cells. After reduction, angiostatin was further alkylated with iodoacetamide and analyzed by SDS gel electrophoresis. As shown in FIG. 34A, the DTT-treated protein migrated at a higher position with molecular weight of about 42 kDa (lane 2) as compared to the native angiostatin with molecular weight of 33 kDa (lane 1), suggesting that angiostatin was completely reduced. The anti-proliferation activity of angiostatin was largely abolished after reduction (FIG. 34B). From these results, we conclude that the correct folding of angiostatin through the intra-kringle disulfide bonds is preferable to maintain its potent effect on inhibition of endothelial cell proliferation.

Amino acid sequence alignment of the kringle domains of human plasminogen shows that K1, K2, K3 and K4 display identical gross architecture and remarkable sequence homology (56–82% identify) as seen in FIG. 35. Among these structures, the high-affinity lysine binding kringle, K1, is the most potent inhibitory segment of endothelial cell proliferation. Of interest, the intermediate-affinity lysine binding fragment, K4, lacks inhibitory activity. These data suggest that the lysine binding site of the kringle structures may not be directly involved in the inhibitory activity. The amino acid conservation and functional divergence of these kringle structures provide an ideal system to study the role mutations caused by DNA replication during evolution. Similar divergent activities relative to the regulation of angiogenesis exhibited by a group of structurally related proteins are also found in the -C-X-C- chemokine and prolactin-growth hormone families (Maione, T. E., Gray, G. S., Petro, A. J., Hunt, A. L., and Donner, S. I. (1990) *Science* 247, 77–79.; Koch, A. E., Polverini, P. J., Kunkel, S. L., Harlow, L. A., DiPietro, L. A., Elner, V. M., Elner, S. J., and Strieter, R. M. (1992) *Science* 258, 1798–1801.; Cao, Y., Chen, C., Weatherbee, J. A., Tsang, M., and Folkman, J. (1995) *J. Exp. Med.* 182, 2069–2077.; Strieter, R. M., Polverini, P. J., Arenberg, D. A., and Kunkel, S. L. (1995) *Shock* 4, 155–160.; Jackson, D., Volpert, O. V., Bouck, N., and Linzer, D. I. H. (1994) *Science* 266, 1581–1584).

Further sequence analysis reveals that K4 contains two positively charged lysine residues adjacent to cysteines 22 and 78 (FIG. 35). $^{1}$H nuclear magnetic resonance (NMR) analysis shows that these 4 lysines, together with lysine 57, form the core of a positively charged domain in K4 (Llinas M, unpublished data), whereas other kringle structures lack such a positively charged domain. Whether this lysine-enriched domain contributes to the loss of inhibitory activity of kringle 4 of human plasminogen remains to be studied. K4 was previously reported to stimulate proliferation of other cell types and to increase the release of intracellular calcium (Donate, L. E., Gherardi, E., Srinivasan, N., Sowdhamini, R., Aporicio, S., and Blundell, T. L. (1994) *Prot. Sci.* 3, 2378–2394). The fact that removal of K4 from angiostatin potentiates its inhibitory activity on endothelial cells suggests that this structure may prevent some of the inhibitory effect of K1–3.

The mechanism underlying how angiostatin and its related kringle fragments specifically inhibit endothelial cell growth remains uncharacterized. It is not yet clear whether the inhibition is mediated by a receptor that is specifically expressed in proliferating endothelial cells, or if angiostatin is internalized by endothelial cells and subsequently inhibits cell proliferation. Alternatively, angiostatin may interact with an endothelial cell adhesion receptor such as integrin $a_vb_3$, blocking integrin-mediated angiogenesis (Brooks, P. C., Montgomery, A. M., Rosenfeld, M., Reisfeld R. A., Hu, T. Klier, G., and Cheresh, D. A. (1994) *Cell* 79, 1157–1164). Of interest, Friedlander et. al. (Friedlander, M., Brooks, P. C., Shaffer, R. W., Kincaid, C. M., Varner, J. A., and Cheresh, D. A. (1995) 270, 1502) reported recently that in vivo angiogenesis in cornea or chorioallantoic membrane models (induced by bFGF and by tumor necrosis factor) was $a_vb_3$ integrin dependent. However, angiogenesis stimulated by VEGF, transforming growth factor a, or phorbol esters was dependent on $a_vb_5$. Antibodies to the individual integrins specifically blocked one of these pathways, and a cyclic protein antagonist of both integrins blocked angiogenesis induced by each cytokine (Friedlander, M., Brooks, P. C., Shaffer, R. W., Kincaid, C. M., Varner, J. A., and Cheresh, D. A. (1995) 270, 1502). Because bFGF- and VEGF- induced angiogenesis are inhibited by angiostatin, it may block a common pathway for these integrin-mediated angiogenesis.

An increasing number of endogenous angiogenesis inhibitors have been identified in the last few decades (Folkman, J. (1995) *N. Engl. J. Med.* 333, 1757–1763). Of the nine characterized endothelial cell suppressors, several inhibitors are proteolytic fragments. For example, the 16 kDa N-terminal fragment of human prolactin inhibits endothelial cell proliferation and blocks angiogenesis in vivo (Clapp, C., Martial, J. A., Guzman, R. C., Rentierdelrue, F., and Weiner, R. I. (1993) *Endorinology* 133, 1292–1299). In a recent paper, D'Angelo et. al. reported that the antiangiogenic 16 kDa N-terminal fragment inhibited the activation of mitogen-activated protein kinase (MAPK) by VEGF and bFGF in capillary endothelial cells (D'Angelo, G., Struman, I., Martial, J., and Weiner, R. (1995) *Proc. Natl. Acad. Sci.* 92, 6374–6378). Similar to angiostatin, the intact parental molecule of prolactin does not inhibit endothelial cell proliferation nor is it an angiogenesis inhibitor. Platelet factor 4 (PF-4) inhibits angiogenesis at high concentrations (Maione, T. E., Gray, G. S., Petro, A. J., Hunt, A. L., and Donner, S. I. (1990) Science 247, 77–79; Cao, Y., Chen, C., Weatherbee, J. A., Tsang, M., and Folkman, J. (1995) *J. Exp. Med.* 182, 2069–2077). However, the N-terminally truncated proteolytically cleaved PF-4 fragment exhibits a 30- to 50-fold increase in its anti-proliferative activity over the intact PF-4 molecule (Gupta, S. K., Hassel, T., and Singh, J. P. (1995) *Proc. Natl. Acad. Sci.* 92, 7799–7803). Smaller protein fragments of fibronectin, murine epidermal growth factor, and thrombospondin have also been shown to specifically inhibit endothelial cell growth (Homandberg, G. A., Williams, J. E., Grant, D., Schumacher, B., and Eisenstein, R. (1985) *Am. J. Pathol.* 120, 327–332; Nelson, J., Allen, W. E., Scott, W. N., Bailie, J. R., Walker, B., McFerran, N. V., and Wilson, D. J. (1995) *Cancer Res.* 55, 3772–3776; Tolsma, S. S., Volpert, O. V., Good, D. J., Frazer, W. A., Polverini, P. J., and Bouck, N. (1993) *J. Cell Biol.* 122, 497–511). Proteolytic processing of a large protein may change the conformational structure of the original molecule or expose new epitopes that are antiangiogenic. Thus, protease(s) may play a critical role in the regulation of angiogenesis. To date, little is known about the regulation of these protease activities in vivo.

The data also show that the disulfide bond mediated folding of the kringle structures in angiostatin is preferable to maintain its inhibitory activity on endothelial cell growth. Kringle structures analogous to those in plasminogen are also found in a variety of other proteins. For example, apolipoprotein (a) has as many as 37 repeats of plasminogen kringle 4 (McLean, J. W., Tomlinson, J. E., Kuang, W.-J., Eaton, D. L., Chen, E. Y., Fless, G. M., Scanu, A. M., and Lawn, R. M. (1987) *Nature* 330, 132–137). The amino terminal portion of pro thrombin also contains two kringles that are homologous to those of plasminogen (Walz, D. A., Hewett-Emmett, D., and Seegers, W. H. (1977) *Proc. Natl. Acad. Sci.* 74, 1969–1973). Urokinase has been shown to possess a kringle structure that shares extensive homology with plasminogen (Gunzler, W. A., J., S. G., Otting, F., Kim, S.-M. A., Frankus, E., and Flohe, L. (1982) *Hoppe-Seyler's A. Physiol. Chem.* 363, 1155–1165). In addition, surfactant protein B and hepatocyte growth factor (HGF), also carry kringle structures (Johansson, J., Curstedt, T., and J örnvall., H. (1991) *Biochem.* 30, 6917–6921; Lukker, N. A., Presta, L. G., and Godowski, P. J. (1994) *Prot. Engin.* 7, 895–903).

Example 28
Suppression of Metastases and of Endothelial Cell Proliferation by Angiostatin Fragments The following example characterizes the activity of additional angiostatin fragments. The data suggests that potent anti-endothelial and tumor suppressive activity can be obtained from such protein fragments of angiostatin.

As used herein, "kringle 1–4BKLS" means a protein derivative of plasminogen having an endothelial cell inhibiting activity, and having an amino acid sequence comprising a sequence homologous to kringle 1–4BKLS, exemplified by, but not limited to that of murine kringle 1–4BKLS (SEQ ID NO:41), and human kringle 1–4BKLS (SEQ ID NO:42), unless indicated otherwise by the context in which it is used. Murine kringle 1–4BKLS (SEQ ID NO:41) corresponds to amino acid positions 93 to 470 (inclusive) of murine plasminogen of SEQ ID NO:1. This example demonstrates that an "angiostatin fragment" can be a plasminogen fragment and encompass an amino acid sequence larger than the angiostatin presented in SEQ ID NO:3, for example, and still have therapeutic endothelial cell proliferation inhibiting activity or anti-angiogenic activity.

A kringle 1–4BLKS amino acid sequence is homologous to the specific kringle 1–4BLKS sequences identified above. Preferably, the amino acid sequences have a degree of homology to the disclosed sequences of at least 60%, more preferably at least 70%, and more preferably at least 80%. It should be understood that a variety of amino acid substitutions, deletions and other modifications to the above listed fragments may be made to improve or modify the endothelial cell inhibiting activity of the fragments. Such modifications are not intended to exceed the scope and spirit of the claims. Furthermore, it is understood that a variety of silent amino acid substitutions, additions, or deletions can be made in the above identified kringle fragments, which do not significantly alter the fragments' endothelial cell inhibiting activity, and which are, therefore, not intended to exceed the scope of the claims.

Cloning of Angiostatin in *Pichia pastoris*

Sequences encoding angiostatin were amplified by PCR using Vent polymerase (New England Biolabs) and primers #154 (5'-ATCGCTCGAGCGTTATTTGAAAAGAAA GTG-3') (SEQ ID NO:43) and #151 (5'-ATCGGAATTCAAGCAGGACAACAGGCGG-3') (SEQ ID NO:44) containing linkers XhoI and Eco R1 respectively and using the plasmid pTrcHis/HAs as template. This plasmid contained sequences encoding amino acids 93 to 470 of human plasminogen (SEQ ID NO:42) for cloning into the Xho I/ECo R1 site of pHIL-S1 expression vector using the *P. pastoris* native secretion signal PHO 1. This same sequence was amplified in the same manner using primers #156 (5'-ATCGTACGTATTATTTGAAAAGAAAGTG-3') (SEQ ID NO:45) and #151 containing linkers Sna B1 and Eco RI respectively, for cloning into the Sna B1/ECo R1 site of expression vector pP1C9 with the alpha-factor secretory signal. The products of the amplifications were gel purified, linkers were digested with the appropriate enzymes, and again purified using gene-clean (Bio 101). These gene fragments were ligated into the appropriate vectors. Resultant clones were selected and plasmid preparations of clones were obtained and linearized to generate His$^+$ Mut$^s$ and His$^+$ Mut+ recombinant strains when transformed into *P. pastoris* host strain GS115. Integration was confirmed by PCR.

Both His$^+$ and His$^+$ Mut$^+$ recombinants were induced with methanol and screened for high expression of angiostatin using Coomassie stained SDS-PAGE gels and immunoblots using mouse monoclonal antibody against kringles 1 to 3 (Castellino, Enzyme Research Laboratories, Inc., South Bend, Ind.). From these, a GS115 transformed *P. pastoris* clone pHIL-S1/HAs18 was selected and phenotypically characterized as His$^+$ Mut$^s$.

Expression of PHIL-S1/HAs18

Expression of angiostatin from pHIL-S1/HAs18 was typical for a His$^+$ Mut$^s$ clone. At induction in baffled shake flasks, 1 L of OD$_{600}$ cells were cultured in 150 ml of buffered methanol complex medium containing 1% yeast extract, 2% peptone, 100 mM potassium phosphate pH 6.0, 1.34% yeast nitrogen base with ammonium sulfate, 0.00004% biotin and 0.5% methanol, in a 1 L baffled flask. Cells were constantly shaken at 30° C., 250 rpm. Methanol was batch fed at 24 hour intervals by addition of absolute methanol to a final of 0.5%. After 120 hours cells were spun at 5,000 rpm for 10 minutes, and supernatants were stored at −70° C. until used.

Purification of Angiostatin From *P. pastoris* Fermentation Broth by Lysine-Sepharose Chromatography All procedures are carried out at 4° C. Crude fermentation broth, typically 200 ml, containing angiostatin was clarified by centrifugation at 14,000×g and concentrated by Centriprep 30 (amicon) 30 kDa molecular weight cutoff membrane to approximately one-fourth the original volume. One volume of 50 mM phosphate buffer, pH 7.5, was added to the concentrated sample which was again concentrated by Centriprep to one-fourth the original sample volume. The sample was again diluted volume:volume with 50 mM sodium phosphate buffer, pH 7.5. 60 g lysine-sepharose 4B (Pharmacia) was resuspended in 500 ml ice-cold 50 mM phosphate buffer, pH 7.5 and used to pack a 48×100 mm column (~180 ml packed volume). The column was washed overnight with 7.5 column volumes (CV) of 50 mM sodium phosphate buffer, pH 7.5, at a flow rate of 1.5 ml/min. The sample was pumped onto the column at a flow rate of 1.5 ml/min and the column washed with 1.5 CV of 50 mM sodium phosphate, pH 7.5, at a flow rate of 3 ml/min. The column was then washed with 1.5 CV phosphate-buffered saline, pH 7.4, at a flow rate of 3 ml/min: angiostatin was then eluted with 0.2M ε-amino-n-caproic acid, pH 7.4 at a flow rate of 3 ml/min. Fractions containing significant absorbance were pooled and dialyzed for 24–48 hours against deionized water and lyophilized. A typical recovery from a 100 mg total protein load is 10 mg angiostatin. Columns were regenerated using 5 column volumes of 50 mM sodium phosphate/1M NaCl, pH 7.5.

Bovine Capillary Endothelial Cell Proliferation Assay

Bovine capillary endothelial cells were obtained as previously described. The cells are maintained in DMEM containing 3 mg/ml of recombinant human bFGF (Scios Nova, Mountainview, Calif.), supplemented with 10% heat-inactivated bovine calf serum, 100 U/ml penicillin, 100 mg/ml streptomycin, and 0.25 mg/ml fungizone (BioWhittaker) in 75 cm² cell-culture flasks. The assay was performed as described previously.

Animal Studies

Six to eight week old male C57BI/6J mice (Jackson Laboratories) were inoculated subcutaneously with murine Lewis lung carcinoma-low metastatic (LLC-LM) line (1×10⁶ cells/injection). Approximately 14 days after implantation, when primary tumor reached 1.5 cm³, animals were anaesthetized with methoxyflurane and primary tumors were surgically excised. The incision site was closed with simple interrupted sutures. Half the animals in this group received a loading dose (3 mg/kg by the subcutaneous route) of recombinant or plasminogen derived angiostatin subcutaneously immediately after surgery, followed by daily inoculations of 1.5 mg/kg for 14 days. A control group of mice received an equal volume of PBS every day for 14 days following surgery. All mice were sacrificed 14 days after primary tumor removal (28 days after tumor implantation), lungs were removed and weighed, and surface metastases were counted with stereomicroscope.

Characteristics of Recombinant Human Angiostatin Fragments

A gene fragment encoding human angiostatin including kringles 1 to 4 of human plasminogen that contains a total of 26 cysteines, was expressed in *Pichia pastoris*, the methylotropic yeast. *P. pastoris* expressed angiostatin binds lysine sepharose and can be specifically eluted by ε-amino caproic acid. This demonstrates that fully functional epsilon amino caproic acid-binding kringle(s), which are physical properties of kringle 1 and 4 of plasminogen (Sottrup-Jensen, L. et al., *Progress in Chemical Fibrinolysis and Thrombolysis*, Vol. 3 (1978) Ravens Press, N.Y. p. 191), can be expressed and secreted by *P. pastoris* and purified by techniques that do not require refolding (FIG. 36A and B). Expressed angiostatin from *P. pastoris* as well as angiostatin purified by elastase cleavage of plasminogen were recognized by a conformationally dependent monoclonal antibody against kringle 1 to 3 (Castellino, Enzyme Research Laboratories, Inc., South Bend, Ind.) (FIG. 36B). This antibody fails to recognize reduced forms of plasminogen or angiostatin.

*P. pastoris* expressed angiostatin is seen as a doublet that migrates at 49 kDa and 51.5 kDa on denatured unreduced SDS-PAGE Coomassie stained gels. *P. pastoris* expressed proteins are post-translationally modified with the majority of N-linked glycosylation of the high-mannose type and insignificant O-linked glycosylation. To evaluate the possibility of glycosylation in *P. pastoris* expressed angiostatin, we digested the recombinant angiostatin with endoglycosidase H specific for high mannose structures, causing the 51.5 kDa band to migrate identically with the band at 49 kDa (FIG. 37A and B). O-glycanase digestion with prior neuraminidase treatment to remove sialic acid residues, did not change the pattern of migration of the doublet (data not shown). These results indicate that *P. pastoris* expressed angiostatin in two forms: (1) with an N-linked complex chain probably of the structure:

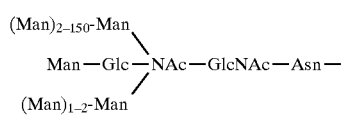

and (2) without any glycosylation.

Inhibition of Bovine Capillary Endothelial Cells In Vitro

To determine if recombinantly expressed angiostatin had the potential for antiangiogenic activity, BCEs were cultured in the presence of bFGF to determine if the addition of purified recombinant angiostatin would inhibit the proliferation of BCEs. Purified *P. pastoris*-expressed angiostatin inhibited the bFGF-driven proliferation of bovine endothelial cells in vitro (FIG. 38B) in a dose dependent manner (FIG. 38C). At 1 ug/ml of recombinant angiostatin, inhibition was 80%. The 50% inhibition was equivalent to that obtained with angiostatin derived from elastase cleavage of human plasminogen.

Suppression of Metastases In Vivo

The transplantable murine LLC (LM) line from which angiostatin was first identified was used. When implanted subcutaneously in syngenic C57B1/6J mice, these tumors grow rapidly, producing >1.5 cm³ tumors within 14 days. Following primary tumor resection, the micometastases in the lungs grow exponentially, to completely cover the surface of the lung. These metastases are highly vascularized by day 14 after primary tumor resection. If the primary tumor is left on, the micrometastases remain dormant and are not macroscopically visible. Recombinant angiostatin was administered systemically to mice following primary tumor resection to test the suppression of the growth of metastases. *P. pastoris* expressed angiostatin administered systemically at 30 ug/mouse/day inhibited the growth of metastases as quantitated by scoring of surface metastases (FIG. 39A) and total lung weight (FIG. 39B). The weights of lungs of mice that had primary tumors resected and that received daily doses of recombinant angiostatin or angiostatin obtained from elastase cleavage of plasminogen were of comparable to those of normal mice (190 to 200 mg). Lungs of mice that had their primary tumors resected and subsequently treated with daily doses of recombinant angiostatin were pink with minimal numbers of unvascularized micrometastases (FIG. 40). In contrast, the mice treated with saline after primary tumor resection had lungs covered with vascularized metastases (FIG. 41). Also of notable importance was an absence of systemic or local toxicity caused by *P. pastoris* expressed angiostatin at the dosage and regimen used in this study. There was no evidence of inflammation or bleeding in all treated mice.

Angiostatin protein expressed by *P. pastoris* possesses two important physical characteristics of the natural protein: (1) it is recognized by a conformationally dependent monoclonal antibody raised against kringle 1 to 3 of human plasminogen (FIG. 36B) and (2) it binds lysine (FIG. 36A and B). These properties indicated that the recombinant angiostatin protein was expressed with a conformation that mimics the native molecule. *P. pastoris* expressed angiostatin protein inhibits the proliferation of bovine capillary endothelial cells stimulated by bFGF in vitro (FIG. 38). when administered systemically, the recombinant angiostatin maintained the otherwise lethal metastastic Lewis lung carcinoma in a suppressed state (FIG. 39A and B and FIG. 40).

Preliminary data shows the absence of a detectable transcript for angiostatin in Lewis lung tumors freshly resected from mice or in LLC cells after 4 passages in in vitro culture. Plasminogen, produced by the liver, is maintained in circulation at a stable plasma concentration of 1.6±0.2 $\mu$M. It is possible that LLC-LM tumors produce an enzyme that cleaves plasminogen, bound or in circulation, to produce angiostatin. Alternatively inflammatory cells attracted to the tumor site could produce such an enzyme.

It is intriguing that both *P. pastoris* as well as native human plasminogen is produced in a glycosylated and a non-glycosylated form. In the case of human plasminogen, a single transcript for a single gene can produce both forms. The molecular mechanism of differential post-translational modifications of human plasminogen, as well as that seen in TPA are unknown.

Angiostatin is highly expressed by *P. pastoris*. Supernatants contain 100 mg/L of the protein. Therefore, the quantities required for clinical trials should be straightforward to produce and purify using standard technology well-known to those skilled in the art. The development of this expression system, and the demonstration of the in vitro and in vivo activity of purified recombinant angiostatin against metastases provided the foundation for assessment of the capacity of these fragments to inhibit tumor growth and prolong life in cancer patients and others suffering from angiogenic-mediated disease.

It should be understood that the foregoing relates only to preferred embodiments of the present invention, and that numerous modifications or alterations may be made therein without departing from the spirit and the scope of the invention as set forth in the appended claims.

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 812 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( v i i ) IMMEDIATE SOURCE:
        ( B ) CLONE: Plasminogen ( x i ) SEQUENCE DESCRIPTION: SEQ ID NO:1:

```
Met  Asp  His  Lys  Glu  Val  Ile  Leu  Leu  Phe  Leu  Leu  Leu  Leu  Lys  Pro
 1              5                        10                       15

Gly  Gln  Gly  Asp  Ser  Leu  Asp  Gly  Tyr  Ile  Ser  Thr  Gln  Gly  Ala  Ser
              20                        25                  30

Leu  Phe  Ser  Leu  Thr  Lys  Lys  Gln  Leu  Ala  Ala  Gly  Gly  Val  Ser  Asp
          35                       40                  45

Cys  Leu  Ala  Lys  Cys  Glu  Gly  Glu  Thr  Asp  Phe  Val  Cys  Arg  Ser  Phe
     50                      55                     60

Gln  Tyr  His  Ser  Lys  Glu  Gln  Gln  Cys  Val  Ile  Met  Ala  Glu  Asn  Ser
 65                      70                     75                       80

Lys  Thr  Ser  Ser  Ile  Ile  Arg  Met  Arg  Asp  Val  Ile  Leu  Phe  Glu  Lys
                85                       90                       95

Arg  Val  Tyr  Leu  Ser  Glu  Cys  Lys  Thr  Gly  Ile  Gly  Asn  Gly  Tyr  Arg
              100                      105                      110

Gly  Thr  Met  Ser  Arg  Thr  Lys  Ser  Gly  Val  Ala  Cys  Gln  Lys  Trp  Gly
```

|     | 115 |     |     |     | 120 |     |     |     | 125 |     |     |     |
|-----|-----|-----|-----|-----|-----|-----|-----|-----|-----|-----|-----|-----|
| Ala | Thr 130 | Phe | Pro | His | Val | Pro 135 | Asn | Tyr | Ser | Pro | Thr 140 | His | Pro | Asn |
| Glu 145 | Gly | Leu | Glu | Glu 150 | Asn | Tyr | Cys | Arg | Asn 155 | Pro | Asp | Asn | Glu | Gln 160 |
| Gly | Pro | Trp | Cys | Tyr 165 | Thr | Thr | Asp | Pro | Lys 170 | Arg | Tyr | Asp | Tyr 175 | Cys |
| Asn | Ile | Pro | Glu 180 | Cys | Glu | Glu | Cys 185 | Met | Tyr | Cys | Ser | Gly 190 | Glu | Lys |
| Tyr | Glu | Gly 195 | Lys | Ile | Ser | Lys | Thr 200 | Met | Ser | Gly | Leu | Asp 205 | Cys | Gln | Ala |
| Trp | Asp 210 | Ser | Gln | Ser | Pro | His 215 | Ala | His | Gly | Tyr | Ile 220 | Pro | Ala | Lys | Phe |
| Pro 225 | Ser | Lys | Asn | Leu | Lys 230 | Met | Asn | Tyr | Cys | His 235 | Asn | Pro | Asp | Gly | Glu 240 |
| Pro | Arg | Pro | Trp | Cys 245 | Phe | Thr | Thr | Asp | Pro 250 | Thr | Lys | Arg | Trp | Glu 255 | Tyr |
| Cys | Asp | Ile | Pro 260 | Arg | Cys | Thr | Thr | Pro 265 | Pro | Pro | Pro | Ser 270 | Pro | Thr |
| Tyr | Gln | Cys 275 | Leu | Lys | Gly | Arg | Gly 280 | Glu | Asn | Tyr | Arg | Gly 285 | Thr | Val | Ser |
| Val | Thr 290 | Val | Ser | Gly | Lys | Thr 295 | Cys | Gln | Arg | Trp | Ser 300 | Glu | Gln | Thr | Pro |
| His 305 | Arg | His | Asn | Arg | Thr 310 | Pro | Glu | Asn | Phe | Pro 315 | Cys | Lys | Asn | Leu | Glu 320 |
| Glu | Asn | Tyr | Cys | Arg 325 | Asn | Pro | Asp | Gly | Glu 330 | Thr | Ala | Pro | Trp | Cys 335 | Tyr |
| Thr | Thr | Asp | Ser 340 | Gln | Leu | Arg | Trp | Glu 345 | Tyr | Cys | Glu | Ile | Pro 350 | Ser | Cys |
| Glu | Ser | Ser 355 | Ala | Ser | Pro | Asp | Gln 360 | Ser | Asp | Ser | Ser | Val 365 | Pro | Pro | Glu |
| Glu | Gln | Thr 370 | Pro | Val | Val | Gln 375 | Glu | Cys | Tyr | Gln | Ser 380 | Asp | Gly | Gln | Ser |
| Tyr 385 | Arg | Gly | Thr | Ser | Ser 390 | Thr | Thr | Ile | Thr | Gly 395 | Lys | Lys | Cys | Gln | Ser 400 |
| Trp | Ala | Ala | Met | Phe 405 | Pro | His | Arg | His | Ser 410 | Lys | Thr | Pro | Glu | Asn | Phe 415 |
| Pro | Asp | Ala | Gly 420 | Leu | Glu | Met | Asn | Tyr 425 | Cys | Arg | Asn | Pro | Asp 430 | Gly | Asp |
| Lys | Gly | Pro 435 | Trp | Cys | Tyr | Thr | Thr 440 | Asp | Pro | Ser | Val | Arg 445 | Trp | Glu | Tyr |
| Cys | Asn 450 | Leu | Lys | Arg | Cys | Ser 455 | Glu | Thr | Gly | Gly | Ser 460 | Val | Val | Glu | Leu |
| Pro 465 | Thr | Val | Ser | Gln | Glu 470 | Pro | Ser | Gly | Pro | Ser 475 | Asp | Ser | Glu | Thr | Asp 480 |
| Cys | Met | Tyr | Gly | Asn 485 | Gly | Lys | Asp | Tyr | Arg 490 | Gly | Lys | Thr | Ala | Val 495 | Thr |
| Ala | Ala | Gly | Thr 500 | Pro | Cys | Gln | Gly | Trp 505 | Ala | Ala | Gln | Glu | Pro 510 | His | Arg |
| His | Ser | Ile 515 | Phe | Thr | Pro | Gln | Thr 520 | Asn | Pro | Arg | Ala | Asp 525 | Leu | Glu | Lys |
| Asn | Tyr 530 | Cys | Arg | Asn | Pro | Asp 535 | Gly | Asp | Val | Asn | Gly 540 | Pro | Trp | Cys | Tyr |

| | | | | | | | | | | | | | | | |
|---|---|---|---|---|---|---|---|---|---|---|---|---|---|---|---|
| Thr | Thr | Asn | Pro | Arg | Lys | Leu | Tyr | Asp | Tyr | Cys | Asp | Ile | Pro | Leu | Cys |
| 545 | | | | | 550 | | | | 555 | | | | | | 560 |
| Ala | Ser | Ala | Ser | Ser | Phe | Glu | Cys | Gly | Lys | Pro | Gln | Val | Glu | Pro | Lys |
| | | | | 565 | | | | | 570 | | | | | 575 | |
| Lys | Cys | Pro | Gly | Arg | Val | Val | Gly | Cys | Val | Ala | Asn | Pro | His | Ser | |
| | | | 580 | | | | | 585 | | | | 590 | | | |
| Trp | Pro | Trp | Gln | Ile | Ser | Leu | Arg | Thr | Arg | Phe | Thr | Gly | Gln | His | Phe |
| | | | 595 | | | | 600 | | | | | 605 | | | |
| Cys | Gly | Gly | Thr | Leu | Ile | Ala | Pro | Glu | Trp | Val | Leu | Thr | Ala | Ala | His |
| | | 610 | | | | 615 | | | | | 620 | | | | |
| Cys | Leu | Glu | Lys | Ser | Ser | Arg | Pro | Glu | Phe | Tyr | Lys | Val | Ile | Leu | Gly |
| 625 | | | | | 630 | | | | 635 | | | | | | 640 |
| Ala | His | Glu | Glu | Tyr | Ile | Arg | Gly | Leu | Asp | Val | Gln | Glu | Ile | Ser | Val |
| | | | | 645 | | | | | 650 | | | | | 655 | |
| Ala | Lys | Leu | Ile | Leu | Glu | Pro | Asn | Asn | Arg | Asp | Ile | Ala | Leu | Leu | Lys |
| | | | 660 | | | | | 665 | | | | | 670 | | |
| Leu | Ser | Arg | Pro | Ala | Thr | Ile | Thr | Asp | Lys | Val | Ile | Pro | Ala | Cys | Leu |
| | | 675 | | | | | 680 | | | | | 685 | | | |
| Pro | Ser | Pro | Asn | Tyr | Met | Val | Ala | Asp | Arg | Thr | Ile | Cys | Tyr | Ile | Thr |
| | 690 | | | | | 695 | | | | | 700 | | | | |
| Gly | Trp | Gly | Glu | Thr | Gln | Gly | Thr | Phe | Gly | Ala | Gly | Arg | Leu | Lys | Glu |
| 705 | | | | | 710 | | | | | 715 | | | | | 720 |
| Ala | Gln | Leu | Pro | Val | Ile | Glu | Asn | Lys | Val | Cys | Asn | Arg | Val | Glu | Tyr |
| | | | | 725 | | | | | 730 | | | | | 735 | |
| Leu | Asn | Asn | Arg | Val | Lys | Ser | Thr | Glu | Leu | Cys | Ala | Gly | Gln | Leu | Ala |
| | | | 740 | | | | | 745 | | | | | 750 | | |
| Gly | Gly | Val | Asp | Ser | Cys | Gln | Gly | Asp | Ser | Gly | Gly | Pro | Leu | Val | Cys |
| | | 755 | | | | | 760 | | | | | 765 | | | |
| Phe | Glu | Lys | Asp | Lys | Tyr | Ile | Leu | Gln | Gly | Val | Thr | Ser | Trp | Gly | Leu |
| | | 770 | | | | | 775 | | | | | 780 | | | |
| Gly | Cys | Ala | Arg | Pro | Asn | Lys | Pro | Gly | Val | Tyr | Val | Arg | Val | Ser | Arg |
| 785 | | | | | 790 | | | | | 795 | | | | | 800 |
| Phe | Val | Asp | Trp | Ile | Glu | Arg | Glu | Met | Arg | Asn | Asn | | | | |
| | | | | 805 | | | | | 810 | | | | | | |

(2) INFORMATION FOR SEQ ID NO:2:

(i) SEQUENCE CHARACTERISTICS:
        (A) LENGTH: 339 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Murine (vii) IMMEDIATE SOURCE:
        (B) CLONE: Angiostatin fragment (xi) SEQUENCE DESCRIPTION: SEQ ID NO:2:

| | | | | | | | | | | | | | | | |
|---|---|---|---|---|---|---|---|---|---|---|---|---|---|---|---|
| Val | Tyr | Leu | Ser | Glu | Cys | Lys | Thr | Gly | Ile | Gly | Asn | Gly | Tyr | Arg | Gly |
| 1 | | | | 5 | | | | | 10 | | | | | 15 | |
| Thr | Met | Ser | Arg | Thr | Lys | Ser | Gly | Val | Ala | Cys | Gln | Lys | Trp | Gly | Ala |

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 20  |     |     |     | 25  |     |     |     | 30  |     |     |
| Thr | Phe | Pro | His | Val | Pro | Asn | Tyr | Ser | Pro | Ser | Thr | His | Pro | Asn | Glu |
|     |     | 35  |     |     |     |     |     | 40  |     |     |     | 45  |     |     |
| Gly | Leu | Glu | Glu | Asn | Tyr | Cys | Arg | Asn | Pro | Asp | Asn | Asp | Glu | Gln | Gly |
|     | 50  |     |     |     |     | 55  |     |     |     |     | 60  |     |     |     |     |
| Pro | Trp | Cys | Tyr | Thr | Thr | Asp | Pro | Asp | Lys | Arg | Tyr | Asp | Tyr | Cys | Asn |
| 65  |     |     |     |     | 70  |     |     |     |     | 75  |     |     |     |     | 80  |
| Ile | Pro | Glu | Cys | Glu | Glu | Glu | Cys | Met | Tyr | Cys | Ser | Gly | Glu | Lys | Tyr |
|     |     |     |     | 85  |     |     |     | 90  |     |     |     |     |     | 95  |     |
| Glu | Gly | Lys | Ile | Ser | Lys | Thr | Met | Ser | Gly | Leu | Asp | Cys | Gln | Ala | Trp |
|     |     |     | 100 |     |     |     |     | 105 |     |     |     |     | 110 |     |     |
| Asp | Ser | Gln | Ser | Pro | His | Ala | His | Gly | Tyr | Ile | Pro | Ala | Lys | Phe | Pro |
|     |     | 115 |     |     |     |     | 120 |     |     |     |     |     | 125 |     |     |
| Ser | Lys | Asn | Leu | Lys | Met | Asn | Tyr | Cys | His | Asn | Pro | Asp | Gly | Glu | Pro |
|     | 130 |     |     |     |     | 135 |     |     |     |     | 140 |     |     |     |     |
| Arg | Pro | Trp | Cys | Phe | Thr | Thr | Asp | Pro | Thr | Lys | Arg | Trp | Glu | Tyr | Cys |
| 145 |     |     |     |     | 150 |     |     |     |     | 155 |     |     |     |     | 160 |
| Asp | Ile | Pro | Arg | Cys | Thr | Thr | Pro | Pro | Pro | Pro | Ser | Pro | Thr | Tyr |     |
|     |     |     |     | 165 |     |     |     |     | 170 |     |     |     | 175 |     |     |
| Gln | Cys | Leu | Lys | Gly | Arg | Gly | Glu | Asn | Tyr | Arg | Gly | Thr | Val | Ser | Val |
|     |     |     | 180 |     |     |     |     | 185 |     |     |     |     | 190 |     |     |
| Thr | Val | Ser | Gly | Lys | Thr | Cys | Gln | Arg | Trp | Ser | Glu | Gln | Thr | Pro | His |
|     |     | 195 |     |     |     |     | 200 |     |     |     |     | 205 |     |     |     |
| Arg | His | Asn | Arg | Thr | Pro | Glu | Asn | Phe | Pro | Cys | Lys | Asn | Leu | Glu | Glu |
|     |     | 210 |     |     |     |     | 215 |     |     |     | 220 |     |     |     |     |
| Asn | Tyr | Cys | Arg | Asn | Pro | Asp | Gly | Glu | Thr | Ala | Pro | Trp | Cys | Tyr | Thr |
| 225 |     |     |     |     | 230 |     |     |     |     | 235 |     |     |     |     | 240 |
| Thr | Asp | Ser | Gln | Leu | Arg | Trp | Glu | Tyr | Cys | Glu | Ile | Pro | Ser | Cys | Glu |
|     |     |     |     | 245 |     |     |     |     | 250 |     |     |     |     | 255 |     |
| Ser | Ser | Ala | Ser | Pro | Asp | Gln | Ser | Asp | Ser | Ser | Val | Pro | Pro | Glu | Glu |
|     |     |     | 260 |     |     |     |     | 265 |     |     |     |     | 270 |     |     |
| Gln | Thr | Pro | Val | Val | Gln | Glu | Cys | Tyr | Gln | Ser | Asp | Gly | Gln | Ser | Tyr |
|     |     | 275 |     |     |     |     | 280 |     |     |     |     | 285 |     |     |     |
| Arg | Gly | Thr | Ser | Ser | Thr | Thr | Ile | Thr | Gly | Lys | Lys | Cys | Gln | Ser | Trp |
|     | 290 |     |     |     |     | 295 |     |     |     |     | 300 |     |     |     |     |
| Ala | Ala | Met | Phe | Pro | His | Arg | His | Ser | Lys | Thr | Pro | Glu | Asn | Phe | Pro |
| 305 |     |     |     |     | 310 |     |     |     |     | 315 |     |     |     |     | 320 |
| Asp | Ala | Gly | Leu | Glu | Met | Asn | Tyr | Cys | Arg | Asn | Pro | Asp | Gly | Asp | Lys |
|     |     |     |     | 325 |     |     |     |     | 330 |     |     |     |     | 335 |     |
| Gly | Pro | Trp |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 339 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens (v i i) IMMEDIATE SOURCE:
  (B) CLONE: Angiostatin fragment (x i) SEQUENCE DESCRIPTION: SEQ ID NO:3:

| Val | Tyr | Leu | Ser | Glu | Cys | Lys | Thr | Gly | Asn | Gly | Lys | Asn | Tyr | Arg | Gly |
|---|---|---|---|---|---|---|---|---|---|---|---|---|---|---|---|
| 1 | | | | 5 | | | | | 10 | | | | | 15 | |
| Thr | Met | Ser | Lys | Thr | Lys | Asn | Gly | Ile | Thr | Cys | Gln | Lys | Trp | Ser | Ser |
| | | | 20 | | | | | 25 | | | | | 30 | | |
| Thr | Ser | Pro | His | Arg | Pro | Arg | Phe | Ser | Pro | Ala | Thr | His | Pro | Ser | Glu |
| | | 35 | | | | | 40 | | | | | 45 | | | |
| Gly | Leu | Glu | Glu | Asn | Tyr | Cys | Arg | Asn | Pro | Asp | Asn | Asp | Pro | Gln | Gly |
| | | 50 | | | | | 55 | | | | 60 | | | | |
| Pro | Trp | Cys | Tyr | Thr | Thr | Asp | Pro | Glu | Lys | Arg | Tyr | Asp | Tyr | Cys | Asp |
| 65 | | | | | 70 | | | | | 75 | | | | | 80 |
| Ile | Leu | Glu | Cys | Glu | Glu | Glu | Cys | Met | His | Cys | Ser | Gly | Glu | Asn | Tyr |
| | | | | 85 | | | | | 90 | | | | | 95 | |
| Asp | Gly | Lys | Ile | Ser | Lys | Thr | Met | Ser | Gly | Leu | Glu | Cys | Gln | Ala | Trp |
| | | | 100 | | | | | 105 | | | | | 110 | | |
| Asp | Ser | Gln | Ser | Pro | His | Ala | His | Gly | Tyr | Ile | Pro | Ser | Lys | Phe | Pro |
| | | | 115 | | | | | 120 | | | | | 125 | | |
| Asn | Lys | Asn | Leu | Lys | Lys | Asn | Tyr | Cys | Arg | Asn | Pro | Asp | Arg | Glu | Leu |
| | | 130 | | | | | 135 | | | | | 140 | | | |
| Arg | Pro | Trp | Cys | Phe | Thr | Thr | Asp | Pro | Asn | Lys | Arg | Trp | Glu | Leu | Cys |
| 145 | | | | | 150 | | | | | 155 | | | | | 160 |
| Asp | Ile | Pro | Arg | Cys | Thr | Thr | Pro | Pro | Pro | Ser | Ser | Gly | Pro | Thr | Tyr |
| | | | | 165 | | | | | 170 | | | | | 175 | |
| Gln | Cys | Leu | Lys | Gly | Thr | Gly | Glu | Asn | Tyr | Arg | Gly | Asn | Val | Ala | Val |
| | | | 180 | | | | | 185 | | | | | 190 | | |
| Thr | Val | Ser | Gly | His | Thr | Cys | Gln | His | Trp | Ser | Ala | Gln | Thr | Pro | His |
| | | 195 | | | | | 200 | | | | | 205 | | | |
| Thr | His | Asn | Arg | Thr | Pro | Glu | Asn | Phe | Pro | Cys | Lys | Asn | Leu | Asp | Glu |
| | | 210 | | | | | 215 | | | | 220 | | | | |
| Asn | Tyr | Cys | Arg | Asn | Pro | Asp | Gly | Lys | Arg | Ala | Pro | Trp | Cys | His | Thr |
| 225 | | | | | 230 | | | | | 235 | | | | | 240 |
| Thr | Asn | Ser | Gln | Val | Arg | Trp | Glu | Tyr | Cys | Lys | Ile | Pro | Ser | Cys | Asp |
| | | | | 245 | | | | | 250 | | | | | 255 | |
| Ser | Ser | Pro | Val | Ser | Thr | Glu | Gln | Leu | Ala | Pro | Thr | Ala | Pro | Pro | Glu |
| | | | 260 | | | | | 265 | | | | | 270 | | |
| Leu | Thr | Pro | Val | Val | Gln | Asp | Cys | Tyr | His | Gly | Asp | Gly | Gln | Ser | Tyr |
| | | 275 | | | | | 280 | | | | | 285 | | | |
| Arg | Gly | Thr | Ser | Ser | Thr | Thr | Thr | Thr | Gly | Lys | Lys | Cys | Gln | Ser | Trp |
| | | 290 | | | | | 295 | | | | | 300 | | | |
| Ser | Ser | Met | Thr | Pro | His | Arg | His | Gln | Lys | Thr | Pro | Glu | Asn | Tyr | Pro |
| 305 | | | | | 310 | | | | | 315 | | | | | 320 |
| Asn | Ala | Gly | Leu | Thr | Met | Asn | Tyr | Cys | Arg | Asn | Pro | Asp | Ala | Asp | Lys |
| | | | | 325 | | | | | 330 | | | | | 335 | |
| Gly | Pro | Trp | | | | | | | | | | | | | |

(2) INFORMATION FOR SEQ ID NO:4:

(i) SEQUENCE CHARACTERISTICS:
    (A) LENGTH: 339 amino acids
    (B) TYPE: amino acid
    (C) STRANDEDNESS:
    (D) TOPOLOGY: linear (ii) MOLECULE TYPE: protein (iii) HYPOTHETICAL: NO (vi) ORIGINAL SOURCE:
(A) ORGANISM: Rhesus monkey (vii) IMMEDIATE SOURCE:
(B) CLONE: Angiostatin fragment (xi) SEQUENCE DESCRIPTION: SEQ ID NO:4:

| | | | | | | | | | | | | | | |
|---|---|---|---|---|---|---|---|---|---|---|---|---|---|---|
| Val | Tyr | Leu | Ser | Glu | Cys | Lys | Thr | Gly | Asn | Gly | Lys | Asn | Tyr | Arg | Gly |
| 1 | | | | 5 | | | | | 10 | | | | | 15 | |
| Thr | Met | Ser | Lys | Thr | Arg | Thr | Gly | Ile | Thr | Cys | Gln | Lys | Trp | Ser | Ser |
| | | | 20 | | | | | 25 | | | | | 30 | | |
| Thr | Ser | Pro | His | Arg | Pro | Thr | Phe | Ser | Pro | Ala | Thr | His | Pro | Ser | Glu |
| | | 35 | | | | | 40 | | | | | 45 | | | |
| Gly | Leu | Glu | Glu | Asn | Tyr | Cys | Arg | Asn | Pro | Asp | Asn | Asp | Gly | Gln | Gly |
| | 50 | | | | | 55 | | | | | 60 | | | | |
| Pro | Trp | Cys | Tyr | Thr | Thr | Asp | Pro | Glu | Glu | Arg | Phe | Asp | Tyr | Cys | Asp |
| 65 | | | | | 70 | | | | | 75 | | | | | 80 |
| Ile | Pro | Glu | Cys | Glu | Asp | Glu | Cys | Met | His | Cys | Ser | Gly | Glu | Asn | Tyr |
| | | | | 85 | | | | | 90 | | | | | 95 | |
| Asp | Gly | Lys | Ile | Ser | Lys | Thr | Met | Ser | Gly | Leu | Glu | Cys | Gln | Ala | Trp |
| | | | 100 | | | | | 105 | | | | | 110 | | |
| Asp | Ser | Gln | Ser | Pro | His | Ala | His | Gly | Tyr | Ile | Pro | Ser | Lys | Phe | Pro |
| | | 115 | | | | | 120 | | | | | 125 | | | |
| Asn | Lys | Asn | Leu | Lys | Lys | Asn | Tyr | Cys | Arg | Asn | Pro | Asp | Gly | Glu | Pro |
| | 130 | | | | | 135 | | | | | 140 | | | | |
| Arg | Pro | Trp | Cys | Phe | Thr | Thr | Asp | Pro | Asn | Lys | Arg | Trp | Glu | Leu | Cys |
| 145 | | | | | 150 | | | | | 155 | | | | | 160 |
| Asp | Ile | Pro | Arg | Cys | Thr | Thr | Pro | Pro | Pro | Ser | Ser | Gly | Pro | Thr | Tyr |
| | | | | 165 | | | | | 170 | | | | | 175 | |
| Gln | Cys | Leu | Lys | Gly | Thr | Gly | Glu | Asn | Tyr | Arg | Gly | Asp | Val | Ala | Val |
| | | | 180 | | | | | 185 | | | | | 190 | | |
| Thr | Val | Ser | Gly | His | Thr | Cys | His | Gly | Trp | Ser | Ala | Gln | Thr | Pro | His |
| | | 195 | | | | | 200 | | | | | 205 | | | |
| Thr | His | Asn | Arg | Thr | Pro | Glu | Asn | Phe | Pro | Cys | Lys | Asn | Leu | Asp | Glu |
| | 210 | | | | | 215 | | | | | 220 | | | | |
| Asn | Tyr | Cys | Arg | Asn | Pro | Asp | Gly | Glu | Lys | Ala | Pro | Trp | Cys | Tyr | Thr |
| 225 | | | | | 230 | | | | | 235 | | | | | 240 |
| Thr | Asn | Ser | Gln | Val | Arg | Trp | Glu | Tyr | Cys | Lys | Ile | Pro | Ser | Cys | Glu |
| | | | | 245 | | | | | 250 | | | | | 255 | |
| Ser | Ser | Pro | Val | Ser | Thr | Glu | Pro | Leu | Asp | Pro | Thr | Ala | Pro | Pro | Glu |
| | | | 260 | | | | | 265 | | | | | 270 | | |
| Leu | Thr | Pro | Val | Val | Gln | Glu | Cys | Tyr | His | Gly | Asp | Gly | Gln | Ser | Tyr |
| | | 275 | | | | | 280 | | | | | 285 | | | |
| Arg | Gly | Thr | Ser | Ser | Thr | Thr | Thr | Thr | Gly | Lys | Lys | Cys | Gln | Ser | Trp |
| | 290 | | | | | 295 | | | | | 300 | | | | |
| Ser | Ser | Met | Thr | Pro | His | Trp | His | Glu | Lys | Thr | Pro | Glu | Asn | Phe | Pro |
| 305 | | | | | 310 | | | | | 315 | | | | | 320 |
| Asn | Ala | Gly | Leu | Thr | Met | Asn | Tyr | Cys | Arg | Asn | Pro | Asp | Ala | Asp | Lys |
| | | | | 325 | | | | | 330 | | | | | 335 | |
| Gly | Pro | Trp | | | | | | | | | | | | | |

(2) INFORMATION FOR SEQ ID NO:5:

( i ) SEQUENCE CHARACTERISTICS:
    ( A ) LENGTH: 339 amino acids
    ( B ) TYPE: amino acid
    ( C ) STRANDEDNESS:
    ( D ) TOPOLOGY: linear ( i i ) MOLECULE TYPE: protein ( i i i ) HYPOTHETICAL: NO ( v i ) ORIGINAL SOURCE:
    ( A ) ORGANISM: Porcine ( v i i ) IMMEDIATE SOURCE:
    ( B ) CLONE: Angiostatin fragment ( x i ) SEQUENCE DESCRIPTION: SEQ ID NO:5:

```
Ile Tyr Leu Ser Glu Cys Lys Thr Gly Asn Gly Lys Asn Tyr Arg Gly
 1               5                  10                  15

Thr Thr Ser Lys Thr Lys Ser Gly Val Ile Cys Gln Lys Trp Ser Val
            20                  25                  30

Ser Ser Pro His Ile Pro Lys Tyr Ser Pro Glu Lys Phe Pro Leu Ala
        35                  40                  45

Gly Leu Glu Glu Asn Tyr Cys Arg Asn Pro Asp Asn Asp Glu Lys Gly
    50                  55                  60

Pro Trp Cys Tyr Thr Thr Asp Pro Glu Thr Arg Phe Asp Tyr Cys Asp
65                  70                  75                  80

Ile Pro Glu Cys Glu Asp Glu Cys Met His Cys Ser Gly Glu His Tyr
                85                  90                  95

Glu Gly Lys Ile Ser Lys Thr Met Ser Gly Ile Glu Cys Gln Ser Trp
                100                 105                 110

Gly Ser Gln Ser Pro His Ala His Gly Tyr Leu Pro Ser Lys Phe Pro
            115                 120                 125

Asn Lys Asn Leu Lys Met Asn Tyr Cys Arg Asn Pro Asp Gly Glu Pro
130                 135                 140

Arg Pro Trp Cys Phe Thr Thr Asp Pro Asn Lys Arg Trp Glu Phe Cys
145                 150                 155                 160

Asp Ile Pro Arg Cys Thr Thr Pro Pro Pro Thr Ser Gly Pro Thr Tyr
                165                 170                 175

Gln Cys Leu Lys Gly Arg Gly Glu Asn Tyr Arg Gly Thr Val Ser Val
            180                 185                 190

Thr Ala Ser Gly His Thr Cys Gln Arg Trp Ser Ala Gln Ser Pro His
            195                 200                 205

Lys His Asn Arg Thr Pro Glu Asn Phe Pro Cys Lys Asn Leu Glu Glu
        210                 215                 220

Asn Tyr Cys Arg Asn Pro Asp Gly Glu Thr Ala Pro Trp Cys Tyr Thr
225                 230                 235                 240

Thr Asp Ser Glu Val Arg Trp Asp Tyr Cys Lys Ile Pro Ser Cys Gly
                245                 250                 255

Ser Ser Thr Thr Ser Thr Glu His Leu Asp Ala Pro Val Pro Pro Glu
            260                 265                 270

Gln Thr Pro Val Ala Gln Asp Cys Tyr Arg Gly Asn Gly Glu Ser Tyr
        275                 280                 285

Arg Gly Thr Ser Ser Thr Thr Ile Thr Gly Arg Lys Cys Gln Ser Trp
        290                 295                 300

Val Ser Met Thr Pro His Arg His Glu Lys Thr Pro Gly Asn Phe Pro
305                 310                 315                 320

Asn Ala Gly Leu Thr Met Asn Tyr Cys Arg Asn Pro Asp Ala Asp Lys
            325                 330                 335
```

Ser Pro Trp (2) INFORMATION FOR SEQ ID NO:6:

(i) SEQUENCE CHARACTERISTICS:
        (A) LENGTH: 339 amino acids
        (B) TYPE: amino acid
        (C) STRANDEDNESS:
        (D) TOPOLOGY: linear (ii) MOLECULE TYPE: protein (iii) HYPOTHETICAL: NO (vi) ORIGINAL SOURCE:
        (A) ORGANISM: Bovine (vii) IMMEDIATE SOURCE:
        (B) CLONE: Angiostatin fragment (xi) SEQUENCE DESCRIPTION: SEQ ID NO:6:

```
Ile Tyr Leu Leu Glu Cys Lys Thr Gly Asn Gly Gln Thr Tyr Arg Gly
 1               5                  10                  15
Thr Thr Ala Glu Thr Lys Ser Gly Val Thr Cys Gln Lys Trp Ser Ala
            20                  25                  30
Thr Ser Pro His Val Pro Lys Phe Ser Pro Glu Lys Phe Pro Leu Ala
            35                  40                  45
Gly Leu Glu Glu Asn Tyr Cys Arg Asn Pro Asp Asn Asp Glu Asn Gly
 50                  55                  60
Pro Trp Cys Tyr Thr Thr Asp Pro Asp Lys Arg Tyr Asp Tyr Cys Asp
 65                  70                  75                  80
Ile Pro Glu Cys Glu Asp Lys Cys Met His Cys Ser Gly Glu Asn Tyr
                    85                  90                  95
Glu Gly Lys Ile Ala Lys Thr Met Ser Gly Arg Asp Cys Gln Ala Trp
                100                 105                 110
Asp Ser Gln Ser Pro His Ala His Gly Tyr Ile Pro Ser Lys Phe Pro
            115                 120                 125
Asn Lys Asn Leu Lys Met Asn Tyr Cys Arg Asn Pro Asp Gly Glu Pro
    130                 135                 140
Arg Pro Trp Cys Phe Thr Thr Asp Pro Gln Lys Arg Trp Glu Phe Cys
145                 150                 155                 160
Asp Ile Pro Arg Cys Thr Thr Pro Pro Pro Ser Ser Gly Pro Lys Tyr
                165                 170                 175
Gln Cys Leu Lys Gly Thr Gly Lys Asn Tyr Gly Gly Thr Val Ala Val
            180                 185                 190
Thr Glu Ser Gly His Thr Cys Gln Arg Trp Ser Glu Gln Thr Pro His
            195                 200                 205
Lys His Asn Arg Thr Pro Glu Asn Phe Pro Cys Lys Asn Leu Glu Glu
    210                 215                 220
Asn Tyr Cys Arg Asn Pro Asp Gly Glu Lys Ala Pro Trp Cys Tyr Thr
225                 230                 235                 240
Thr Asn Ser Glu Val Arg Trp Glu Tyr Cys Thr Ile Pro Ser Cys Glu
                245                 250                 255
Ser Ser Pro Leu Ser Thr Glu Arg Met Asp Val Pro Val Pro Pro Glu
            260                 265                 270
Gln Thr Pro Val Pro Gln Asp Cys Tyr His Gly Asn Gly Gln Ser Tyr
            275                 280                 285
Arg Gly Thr Ser Ser Thr Thr Ile Thr Gly Arg Lys Cys Gln Ser Trp
290                 295                 300
```

| Ser | Ser | Met | Thr | Pro | His | Arg | His | Leu | Lys | Thr | Pro | Glu | Asn | Tyr | Pro |
| 305 | | | | | 310 | | | | | 315 | | | | | 320 |

| Asn | Ala | Gly | Leu | Thr | Met | Asn | Tyr | Cys | Arg | Asn | Pro | Asp | Ala | Asp | Lys |
| | | | | 325 | | | | | 330 | | | | | 335 | |

| Ser | Pro | Trp |

(2) INFORMATION FOR SEQ ID NO:7:

(i) SEQUENCE CHARACTERISTICS:
        (A) LENGTH: 79 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Murine (vii) IMMEDIATE SOURCE:
        (B) CLONE: K1

(xi) SEQUENCE DESCRIPTION: SEQ ID NO:7:

| Cys | Lys | Thr | Gly | Ile | Gly | Asn | Gly | Tyr | Arg | Gly | Thr | Met | Ser | Arg | Thr |
| 1 | | | | 5 | | | | | 10 | | | | | 15 | |

| Lys | Ser | Gly | Val | Ala | Cys | Gln | Lys | Trp | Gly | Ala | Thr | Phe | Pro | His | Val |
| | | | 20 | | | | | 25 | | | | | 30 | | |

| Pro | Asn | Tyr | Ser | Pro | Ser | Thr | His | Pro | Asn | Glu | Gly | Leu | Glu | Glu | Asn |
| | | 35 | | | | | 40 | | | | | 45 | | | |

| Tyr | Cys | Arg | Asn | Pro | Asp | Asn | Asp | Glu | Gln | Gly | Pro | Trp | Cys | Tyr | Thr |
| | 50 | | | | | 55 | | | | | 60 | | | | |

| Thr | Asp | Pro | Asp | Lys | Arg | Tyr | Asp | Tyr | Cys | Asn | Ile | Pro | Glu | Cys |
| 65 | | | | | 70 | | | | | 75 | | | | |

(2) INFORMATION FOR SEQ ID NO:8:

(i) SEQUENCE CHARACTERISTICS:
        (A) LENGTH: 79 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (vii) IMMEDIATE SOURCE:
        (B) CLONE: K1

(xi) SEQUENCE DESCRIPTION: SEQ ID NO:8:

| Cys | Lys | Thr | Gly | Asn | Gly | Lys | Asn | Tyr | Arg | Gly | Thr | Met | Ser | Lys | Thr |
| 1 | | | | 5 | | | | | 10 | | | | | 15 | |

| Lys | Asn | Gly | Ile | Thr | Cys | Gln | Lys | Trp | Ser | Ser | Thr | Ser | Pro | His | Arg |
| | | | 20 | | | | | 25 | | | | | 30 | | |

|    |     |     |     |     |     |     |     |     |     |     |     |     |     |     |
|----|-----|-----|-----|-----|-----|-----|-----|-----|-----|-----|-----|-----|-----|-----|
| Pro | Arg | Phe | Ser | Pro | Ala | Thr | His | Pro | Ser | Glu | Gly | Leu | Glu | Glu | Asn |
|     | 35  |     |     |     |     | 40  |     |     |     |     | 45  |     |     |     |

```
Pro  Arg  Phe  Ser  Pro  Ala  Thr  His  Pro  Ser  Glu  Gly  Leu  Glu  Glu  Asn
     35                      40                      45

Tyr  Cys  Arg  Asn  Pro  Asp  Asn  Asp  Pro  Gln  Gly  Pro  Trp  Cys  Tyr  Thr
     50                      55                      60

Thr  Asp  Pro  Glu  Lys  Arg  Tyr  Asp  Tyr  Cys  Asp  Ile  Leu  Glu  Cys
65                       70                      75
```

( 2 ) INFORMATION FOR SEQ ID NO:9:

( i ) SEQUENCE CHARACTERISTICS:
        ( A ) LENGTH: 79 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rhesus monkey ( v i i ) IMMEDIATE SOURCE:
        ( B ) CLONE: K1

( x i ) SEQUENCE DESCRIPTION: SEQ ID NO:9:

```
Cys  Lys  Thr  Gly  Asn  Gly  Lys  Asn  Tyr  Arg  Gly  Thr  Met  Ser  Lys  Thr
1                    5                      10                      15

Arg  Thr  Gly  Ile  Thr  Cys  Gln  Lys  Trp  Ser  Ser  Thr  Ser  Pro  His  Arg
                20                      25                      30

Pro  Thr  Phe  Ser  Pro  Ala  Thr  His  Pro  Ser  Glu  Gly  Leu  Glu  Glu  Asn
          35                      40                      45

Tyr  Cys  Arg  Asn  Pro  Asp  Asn  Asp  Gly  Gln  Gly  Pro  Trp  Cys  Tyr  Thr
     50                      55                      60

Thr  Asp  Pro  Glu  Glu  Arg  Phe  Asp  Tyr  Cys  Asp  Ile  Pro  Glu  Cys
65                       70                      75
```

( 2 ) INFORMATION FOR SEQ ID NO:10:

( i ) SEQUENCE CHARACTERISTICS:
        ( A ) LENGTH: 79 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porcine ( v i i ) IMMEDIATE SOURCE:
        ( B ) CLONE: K1

( x i ) SEQUENCE DESCRIPTION: SEQ ID NO:10:

```
Cys  Lys  Thr  Gly  Asn  Gly  Lys  Asn  Tyr  Arg  Gly  Thr  Thr  Ser  Lys  Thr
1                    5                      10                      15

Lys  Ser  Gly  Val  Ile  Cys  Gln  Lys  Trp  Ser  Val  Ser  Ser  Pro  His  Ile
                20                      25                      30
```

|  | Pro | Lys | Tyr | Ser | Pro | Glu | Lys | Phe | Pro | Leu | Ala | Gly | Leu | Glu | Glu | Asn |
|---|---|---|---|---|---|---|---|---|---|---|---|---|---|---|---|---|
|  |  |  | 35 |  |  |  | 40 |  |  |  |  |  | 45 |  |  |  |

|  | Tyr | Cys | Arg | Asn | Pro | Asp | Asn | Asp | Glu | Lys | Gly | Pro | Trp | Cys | Tyr | Thr |
|---|---|---|---|---|---|---|---|---|---|---|---|---|---|---|---|---|
|  |  | 50 |  |  |  | 55 |  |  |  |  |  | 60 |  |  |  |  |

|  | Thr | Asp | Pro | Glu | Thr | Arg | Phe | Asp | Tyr | Cys | Asp | Ile | Pro | Glu | Cys |
|---|---|---|---|---|---|---|---|---|---|---|---|---|---|---|---|
|  | 65 |  |  |  |  | 70 |  |  |  |  | 75 |  |  |  |  |

(2) INFORMATION FOR SEQ ID NO:11:

(i) SEQUENCE CHARACTERISTICS:
        (A) LENGTH: 79 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Bovine (vii) IMMEDIATE SOURCE:
        (B) CLONE: K1

(xi) SEQUENCE DESCRIPTION: SEQ ID NO:11:

|  | Cys | Lys | Thr | Gly | Asn | Gly | Gln | Thr | Tyr | Arg | Gly | Thr | Thr | Ala | Glu | Thr |
|---|---|---|---|---|---|---|---|---|---|---|---|---|---|---|---|---|
|  | 1 |  |  |  | 5 |  |  |  |  | 10 |  |  |  |  | 15 |  |

|  | Lys | Ser | Gly | Val | Thr | Cys | Gln | Lys | Trp | Ser | Ala | Thr | Ser | Pro | His | Val |
|---|---|---|---|---|---|---|---|---|---|---|---|---|---|---|---|---|
|  |  |  |  | 20 |  |  |  |  | 25 |  |  |  |  | 30 |  |  |

|  | Pro | Lys | Phe | Ser | Pro | Glu | Lys | Phe | Pro | Leu | Ala | Gly | Leu | Glu | Glu | Asn |
|---|---|---|---|---|---|---|---|---|---|---|---|---|---|---|---|---|
|  |  |  | 35 |  |  |  | 40 |  |  |  |  |  | 45 |  |  |  |

|  | Tyr | Cys | Arg | Asn | Pro | Asp | Asn | Asp | Glu | Asn | Gly | Pro | Trp | Cys | Tyr | Thr |
|---|---|---|---|---|---|---|---|---|---|---|---|---|---|---|---|---|
|  |  | 50 |  |  |  | 55 |  |  |  |  |  | 60 |  |  |  |  |

|  | Thr | Asp | Pro | Asp | Lys | Arg | Tyr | Asp | Tyr | Cys | Asp | Ile | Pro | Glu | Cys |
|---|---|---|---|---|---|---|---|---|---|---|---|---|---|---|---|
|  | 65 |  |  |  |  | 70 |  |  |  |  | 75 |  |  |  |  |

(2) INFORMATION FOR SEQ ID NO:12:

(i) SEQUENCE CHARACTERISTICS:
        (A) LENGTH: 78 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Murine (vii) IMMEDIATE SOURCE:
        (B) CLONE: K2

(xi) SEQUENCE DESCRIPTION: SEQ ID NO:12:

|  | Cys | Met | Tyr | Cys | Ser | Gly | Glu | Lys | Tyr | Glu | Gly | Lys | Ile | Ser | Lys | Thr |
|---|---|---|---|---|---|---|---|---|---|---|---|---|---|---|---|---|
|  | 1 |  |  |  | 5 |  |  |  |  | 10 |  |  |  |  | 15 |  |

|  | Met | Ser | Gly | Leu | Asp | Cys | Gln | Ala | Trp | Asp | Ser | Gln | Ser | Pro | His | Ala |
|---|---|---|---|---|---|---|---|---|---|---|---|---|---|---|---|---|
|  |  |  |  | 20 |  |  |  |  | 25 |  |  |  |  | 30 |  |  |

```
His Gly Tyr Ile Pro Ala Lys Phe Pro Ser Lys Asn Leu Lys Met Asn
          35                  40                  45

Tyr Cys His Asn Pro Asp Gly Glu Pro Arg Pro Trp Cys Phe Thr Thr
     50                  55                  60

Asp Pro Thr Lys Arg Trp Glu Tyr Cys Asp Ile Pro Arg Cys
 65                  70                  75
```

(2) INFORMATION FOR SEQ ID NO:13:

(i) SEQUENCE CHARACTERISTICS:
        (A) LENGTH: 78 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapien (vii) IMMEDIATE SOURCE:
        (B) CLONE: K2

(xi) SEQUENCE DESCRIPTION: SEQ ID NO:13:

```
Cys Met His Ser Ser Gly Glu Asn Tyr Asp Gly Lys Ile Ser Lys Thr
 1               5                  10                  15

Met Ser Gly Leu Glu Cys Gln Ala Trp Asp Ser Gln Ser Pro His Ala
          20                  25                  30

His Gly Tyr Ile Pro Ser Lys Phe Pro Asn Lys Asn Leu Lys Lys Asn
          35                  40                  45

Tyr Cys Arg Asn Pro Asp Arg Glu Leu Arg Pro Trp Cys Phe Thr Thr
     50                  55                  60

Asp Pro Asn Lys Arg Trp Glu Leu Cys Asp Ile Pro Arg Cys
 65                  70                  75
```

(2) INFORMATION FOR SEQ ID NO:14:

(i) SEQUENCE CHARACTERISTICS:
        (A) LENGTH: 78 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rhesus monkey (vii) IMMEDIATE SOURCE:
        (B) CLONE: K2

(xi) SEQUENCE DESCRIPTION: SEQ ID NO:14:

```
Cys Met His Cys Ser Gly Glu Asn Tyr Asp Gly Lys Ile Ser Lys Thr
 1               5                  10                  15

Met Ser Gly Leu Glu Cys Gln Ala Trp Asp Ser Gln Ser Pro His Ala
          20                  25                  30
```

|   |   |   |   |   |   |   |   |   |   |   |   |   |   |   |
|---|---|---|---|---|---|---|---|---|---|---|---|---|---|---|
| His | Gly | Tyr<br>35 | Ile | Pro | Ser | Lys | Phe<br>40 | Pro | Asn | Lys | Asn | Leu<br>45 | Lys | Lys | Asn |
| Tyr | Cys<br>50 | Arg | Asn | Pro | Asp | Gly<br>55 | Glu | Pro | Arg | Pro | Trp<br>60 | Cys | Phe | Thr | Thr |
| Asp<br>65 | Pro | Asn | Lys | Arg | Trp<br>70 | Glu | Leu | Cys | Asp | Ile<br>75 | Pro | Arg | Cys |

( 2 ) INFORMATION FOR SEQ ID NO:15:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porcine ( v i i ) IMMEDIATE SOURCE:
        ( B ) CLONE: K2

( x i ) SEQUENCE DESCRIPTION: SEQ ID NO:15:

|   |   |   |   |   |   |   |   |   |   |   |   |   |   |   |   |
|---|---|---|---|---|---|---|---|---|---|---|---|---|---|---|---|
| Cys<br>1 | Met | His | Cys | Ser<br>5 | Gly | Glu | His | Tyr | Glu<br>10 | Gly | Lys | Ile | Ser | Lys<br>15 | Thr |
| Met | Ser | Gly | Ile<br>20 | Glu | Cys | Gln | Ser | Trp<br>25 | Gly | Ser | Gln | Ser | Pro<br>30 | His | Ala |
| His | Gly | Tyr<br>35 | Leu | Pro | Ser | Lys | Phe<br>40 | Pro | Asn | Lys | Asn | Leu<br>45 | Lys | Met | Asn |
| Tyr | Cys<br>50 | Arg | Asn | Pro | Asp | Gly<br>55 | Glu | Pro | Arg | Pro | Trp<br>60 | Cys | Phe | Thr | Thr |
| Asp<br>65 | Pro | Asn | Lys | Arg | Trp<br>70 | Glu | Phe | Cys | Asp | Ile<br>75 | Pro | Arg | Cys |

( 2 ) INFORMATION FOR SEQ ID NO:16:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Bovine ( v i i ) IMMEDIATE SOURCE:
        ( B ) CLONE: K2

( x i ) SEQUENCE DESCRIPTION: SEQ ID NO:16:

|   |   |   |   |   |   |   |   |   |   |   |   |   |   |   |   |
|---|---|---|---|---|---|---|---|---|---|---|---|---|---|---|---|
| Cys<br>1 | Met | His | Cys | Ser<br>5 | Gly | Glu | Asn | Tyr | Glu<br>10 | Gly | Lys | Ile | Ala | Lys<br>15 | Thr |
| Met | Ser | Gly | Arg<br>20 | Asp | Cys | Gln | Ala | Trp<br>25 | Asp | Ser | Gln | Ser | Pro<br>30 | His | Ala |

-continued

```
His  Gly  Tyr  Ile  Pro  Ser  Lys  Phe  Pro  Asn  Lys  Asn  Leu  Lys  Met  Asn
          35                       40                  45

Tyr  Cys  Arg  Asn  Pro  Asp  Gly  Glu  Pro  Arg  Pro  Trp  Cys  Phe  Thr  Thr
     50                       55                       60

Asp  Pro  Gln  Lys  Arg  Trp  Glu  Phe  Cys  Asp  Ile  Pro  Arg  Cys
65                       70                  75
```

( 2 ) INFORMATION FOR SEQ ID NO:17:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( v i i ) IMMEDIATE SOURCE:
        ( B ) CLONE: K3

( x i ) SEQUENCE DESCRIPTION: SEQ ID NO:17:

```
Cys  Leu  Lys  Gly  Arg  Gly  Glu  Asn  Tyr  Arg  Gly  Thr  Val  Ser  Val  Thr
1                   5                       10                      15

Val  Ser  Gly  Lys  Thr  Cys  Gln  Arg  Trp  Ser  Glu  Gln  Thr  Pro  His  Arg
          20                       25                       30

His  Asn  Arg  Thr  Pro  Glu  Asn  Phe  Pro  Cys  Lys  Asn  Leu  Glu  Glu  Asn
          35                       40                       45

Tyr  Cys  Arg  Asn  Pro  Asp  Gly  Glu  Thr  Ala  Pro  Trp  Cys  Tyr  Thr  Thr
     50                       55                       60

Asp  Ser  Gln  Leu  Arg  Trp  Glu  Tyr  Cys  Glu  Ile  Pro  Ser  Cys
65                       70                       75
```

( 2 ) INFORMATION FOR SEQ ID NO:18:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K3

( x i ) SEQUENCE DESCRIPTION: SEQ ID NO:18:

```
Cys  Leu  Lys  Gly  Thr  Gly  Glu  Asn  Tyr  Arg  Gly  Asn  Val  Ala  Val  Thr
1                   5                       10                      15

Val  Ser  Gly  His  Thr  Cys  Gln  His  Trp  Ser  Ala  Gln  Thr  Pro  His  Thr
          20                       25                       30
```

His Asn Arg Thr Pro Glu Asn Phe Pro Ser Lys Asn Leu Asp Glu Asn
            35                      40                      45

Tyr Cys Arg Asn Pro Asp Gly Lys Arg Ala Pro Trp Cys His Thr Thr
    50                      55                      60

Asn Ser Gln Val Arg Trp Glu Tyr Cys Lys Ile Pro Ser Cys
65                      70                      75

( 2 ) INFORMATION FOR SEQ ID NO:19:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rhesus monkey ( v i i ) IMMEDIATE SOURCE:
        ( B ) CLONE: K3

( x i ) SEQUENCE DESCRIPTION: SEQ ID NO:19:

Cys Leu Lys Gly Thr Gly Glu Asn Tyr Arg Gly Asp Val Ala Val Thr
1                   5                       10                      15

Val Ser Gly His Thr Cys His Gly Trp Ser Ala Gln Thr Pro His Thr
            20                      25                      30

His Asn Arg Thr Pro Glu Asn Phe Pro Cys Lys Asn Leu Asp Glu Asn
            35                      40                      45

Tyr Cys Arg Asn Pro Asp Gly Glu Lys Ala Pro Trp Cys Tyr Thr Thr
    50                      55                      60

Asn Ser Gln Val Arg Trp Glu Tyr Cys Lys Ile Pro Ser Cys
65                      70                      75

( 2 ) INFORMATION FOR SEQ ID NO:20:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porcine ( v i i ) IMMEDIATE SOURCE:
        ( B ) CLONE: K3

( x i ) SEQUENCE DESCRIPTION: SEQ ID NO:20:

Cys Leu Lys Gly Arg Gly Glu Asn Tyr Arg Gly Thr Val Ser Val Thr
1                   5                       10                      15

Ala Ser Gly His Thr Cys Gln Arg Trp Ser Ala Gln Ser Pro His Lys
            20                      25                      30

```
         His Asn Arg Thr Pro Glu Asn Phe Pro Cys Lys Asn Leu Glu Glu Asn
                     35                  40                  45

Tyr Cys Arg Asn Pro Asp Gly Glu Thr Ala Pro Trp Cys Tyr Thr Thr
             50                  55                  60

Asp Ser Glu Val Arg Trp Asp Tyr Cys Lys Ile Pro Ser Cys
         65                  70                  75
```

( 2 ) INFORMATION FOR SEQ ID NO:21:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Bovine ( v i i ) IMMEDIATE SOURCE:
        ( B ) CLONE: K3

( x i ) SEQUENCE DESCRIPTION: SEQ ID NO:21:

```
         Cys Leu Lys Gly Thr Gly Lys Asn Tyr Gly Gly Thr Val Ala Val Thr
         1               5                  10                  15

Glu Ser Gly His Thr Cys Gln Arg Trp Ser Glu Gln Thr Pro His Lys
                     20                  25                  30

His Asn Arg Thr Pro Glu Asn Phe Pro Cys Lys Asn Leu Glu Glu Asn
                     35                  40                  45

Tyr Cys Arg Asn Pro Asp Gly Glu Lys Ala Pro Trp Cys Tyr Thr Thr
             50                  55                  60

Asn Ser Glu Val Arg Trp Glu Tyr Cys Thr Ile Pro Ser Cys
         65                  70                  75
```

( 2 ) INFORMATION FOR SEQ ID NO:22:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( v i i ) IMMEDIATE SOURCE:
        ( B ) CLONE: K4

( x i ) SEQUENCE DESCRIPTION: SEQ ID NO:22:

```
         Cys Tyr Gln Ser Asp Gly Gln Ser Tyr Arg Gly Thr Ser Ser Thr Thr
         1               5                  10                  15

Ile Thr Gly Lys Lys Cys Gln Ser Trp Ala Ala Met Phe Pro His Arg
                     20                  25                  30
```

-continued

```
His Ser Lys Thr Pro Glu Asn Phe Pro Asp Ala Gly Leu Glu Met Asn
        35                  40                  45

Tyr Cys Arg Asn Pro Asp Gly Asp Lys Gly Pro Trp Cys Tyr Thr Thr
    50                  55                  60

Asp Pro Ser Val Arg Trp Glu Tyr Cys Asn Leu Lys Arg Cys
65                  70                  75
```

( 2 ) INFORMATION FOR SEQ ID NO:23:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K4

( x i ) SEQUENCE DESCRIPTION: SEQ ID NO:23:

```
Cys Tyr His Gly Asp Gly Gln Ser Tyr Arg Gly Thr Ser Ser Thr Thr
1               5                   10                  15

Thr Thr Gly Lys Lys Cys Gln Ser Trp Ser Ser Met Thr Pro His Arg
            20                  25                  30

His Gln Lys Thr Pro Glu Asn Tyr Pro Asn Ala Gly Leu Thr Met Asn
        35                  40                  45

Tyr Cys Arg Asn Pro Asp Ala Asp Lys Gly Pro Trp Cys Phe Thr Thr
    50                  55                  60

Asp Pro Ser Val Arg Trp Glu Tyr Cys Asn Leu Lys Lys Cys
65                  70                  75
```

( 2 ) INFORMATION FOR SEQ ID NO:24:

( i ) SEQUENCE CHARACTERISTICS:
        ( A ) LENGTH: 168 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( v i i ) IMMEDIATE SOURCE:
        ( B ) CLONE: K2-3

( x i ) SEQUENCE DESCRIPTION: SEQ ID NO:24:

```
Cys Met Tyr Cys Ser Gly Glu Lys Tyr Glu Gly Lys Ile Ser Lys Thr
1               5                   10                  15

Met Ser Gly Leu Asp Cys Gln Ala Trp Asp Ser Gln Ser Pro His Ala
            20                  25                  30
```

His Gly Tyr Ile Pro Ala Lys Phe Pro Ser Lys Asn Leu Lys Met Asn
            35                  40              45

Tyr Cys His Asn Pro Asp Gly Glu Pro Arg Pro Trp Cys Phe Thr Thr
    50              55                  60

Asp Pro Thr Lys Arg Trp Glu Tyr Cys Asp Ile Pro Arg Cys Thr Thr
65              70              75                              80

Pro Pro Pro Pro Pro Ser Pro Thr Tyr Gln Cys Leu Lys Gly Arg Gly
                85                  90                      95

Glu Asn Tyr Arg Gly Thr Val Ser Val Thr Val Ser Gly Lys Thr Cys
            100             105                     110

Gln Arg Trp Ser Glu Gln Thr Pro His Arg His Asn Arg Thr Pro Glu
        115                 120                 125

Asn Phe Pro Cys Lys Asn Leu Glu Glu Asn Tyr Cys Arg Asn Pro Asp
    130                 135                 140

Gly Glu Thr Ala Pro Trp Cys Tyr Thr Thr Asp Ser Gln Leu Arg Trp
145                 150                 155                     160

Glu Tyr Cys Glu Ile Pro Ser Cys
                165

(2) INFORMATION FOR SEQ ID NO:25:

(i) SEQUENCE CHARACTERISTICS:
        (A) LENGTH: 168 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (vii) IMMEDIATE SOURCE:
        (B) CLONE: K2-3

(xi) SEQUENCE DESCRIPTION: SEQ ID NO:25:

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
            35                  40              45

Tyr Cys Arg Asn Pro Asp Arg Glu Leu Arg Pro Trp Cys Phe Thr Thr
    50              55                  60

Asp Pro Asn Lys Arg Trp Glu Leu Cys Asp Ile Pro Arg Cys Thr Thr
65              70              75                              80

Pro Pro Pro Ser Ser Gly Pro Thr Tyr Gln Cys Leu Lys Gly Thr Gly
                85                  90                      95

Glu Asn Tyr Arg Gly Asn Val Ala Val Thr Val Ser Gly His Thr Cys
            100             105                     110

Gln His Trp Ser Ala Gln Thr Pro His Thr His Asn Arg Thr Pro Glu
        115                 120                 125

Asn Phe Pro Cys Lys Asn Leu Asp Glu Asn Tyr Cys Arg Asn Pro Asp
    130                 135                 140

Gly Lys Arg Ala Pro Trp Cys His Thr Thr Asn Ser Gln Val Arg Trp

|   | 145 |   |   |   | 150 |   |   |   | 155 |   |   |   | 160 |
|---|---|---|---|---|---|---|---|---|---|---|---|---|---|

Glu Tyr Cys Lys Ile Pro Ser Cys
                165

(2) INFORMATION FOR SEQ ID NO:26:

(i) SEQUENCE CHARACTERISTICS:
        (A) LENGTH: 168 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rhesus monkey (vii) IMMEDIATE SOURCE:
        (B) CLONE: K2-3

(xi) SEQUENCE DESCRIPTION: SEQ ID NO:26:

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Gly Glu Pro Arg Pro Trp Cys Phe Thr Thr
    50                  55                  60

Asp Pro Asn Lys Arg Trp Glu Leu Cys Asp Ile Pro Arg Cys Thr Thr
65                  70                  75                  80

Pro Pro Pro Ser Ser Gly Pro Thr Tyr Gln Cys Leu Lys Gly Thr Gly
                85                  90                  95

Glu Asn Tyr Arg Gly Asp Val Ala Val Thr Val Ser Gly His Thr Cys
            100                 105                 110

His Gly Trp Ser Ala Gln Thr Pro His Thr His Asn Arg Thr Pro Glu
        115                 120                 125

Asn Phe Pro Cys Lys Asn Leu Asp Glu Asn Tyr Cys Arg Asn Pro Asp
    130                 135                 140

Gly Glu Lys Ala Pro Trp Cys Tyr Thr Thr Asn Ser Gln Val Arg Trp
145                 150                 155                 160

Glu Tyr Cys Lys Ile Pro Ser Cys
                165

(2) INFORMATION FOR SEQ ID NO:27:

(i) SEQUENCE CHARACTERISTICS:
        (A) LENGTH: 168 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
(A) ORGANISM: Porcine (vii) IMMEDIATE SOURCE:
(B) CLONE: K2-3

(xi) SEQUENCE DESCRIPTION: SEQ ID NO:27:

| Cys | Met | His | Cys | Ser | Gly | Glu | His | Tyr | Glu | Gly | Lys | Ile | Ser | Lys | Thr |
|---|---|---|---|---|---|---|---|---|---|---|---|---|---|---|---|
| 1 | | | | 5 | | | | | 10 | | | | | 15 | |
| Met | Ser | Gly | Ile | Glu | Cys | Gln | Ser | Trp | Gly | Ser | Gln | Ser | Pro | His | Ala |
| | | | 20 | | | | 25 | | | | | 30 | | | |
| His | Gly | Tyr | Leu | Pro | Ser | Lys | Phe | Pro | Asn | Lys | Asn | Leu | Lys | Met | Asn |
| | | 35 | | | | | 40 | | | | | 45 | | | |
| Tyr | Cys | Arg | Asn | Pro | Asp | Gly | Glu | Pro | Arg | Pro | Trp | Cys | Phe | Thr | Thr |
| | 50 | | | | | 55 | | | | | 60 | | | | |
| Asp | Pro | Asn | Lys | Arg | Trp | Glu | Phe | Cys | Asp | Ile | Pro | Arg | Cys | Thr | Thr |
| 65 | | | | | 70 | | | | | 75 | | | | | 80 |
| Pro | Pro | Pro | Thr | Ser | Gly | Pro | Thr | Tyr | Gln | Cys | Leu | Lys | Gly | Arg | Gly |
| | | | | 85 | | | | | 90 | | | | | 95 | |
| Glu | Asn | Tyr | Arg | Gly | Thr | Val | Ser | Val | Thr | Ala | Ser | Gly | His | Thr | Cys |
| | | | 100 | | | | | 105 | | | | | 110 | | |
| Gln | Arg | Trp | Ser | Ala | Gln | Ser | Pro | His | Lys | His | Asn | Arg | Thr | Pro | Glu |
| | | 115 | | | | | 120 | | | | | 125 | | | |
| Asn | Phe | Pro | Cys | Lys | Asn | Leu | Glu | Glu | Asn | Tyr | Cys | Arg | Asn | Pro | Asp |
| | 130 | | | | | 135 | | | | | 140 | | | | |
| Gly | Glu | Thr | Ala | Pro | Trp | Cys | Tyr | Thr | Thr | Asp | Ser | Glu | Val | Arg | Trp |
| 145 | | | | | 150 | | | | | 155 | | | | | 160 |
| Asp | Tyr | Cys | Lys | Ile | Pro | Ser | Cys | | | | | | | | |
| | | | | 165 | | | | | | | | | | | |

(2) INFORMATION FOR SEQ ID NO:28:

(i) SEQUENCE CHARACTERISTICS:
(A) LENGTH: 168 amino acids
(B) TYPE: amino acid
(C) STRANDEDNESS:
(D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
(A) ORGANISM: Bovine (vii) IMMEDIATE SOURCE:
(B) CLONE: K2-3

(xi) SEQUENCE DESCRIPTION: SEQ ID NO:28:

| Cys | Met | His | Cys | Ser | Gly | Glu | Asn | Tyr | Glu | Gly | Lys | Ile | Ala | Lys | Thr |
|---|---|---|---|---|---|---|---|---|---|---|---|---|---|---|---|
| 1 | | | | 5 | | | | | 10 | | | | | 15 | |
| Met | Ser | Gly | Arg | Asp | Cys | Gln | Ala | Trp | Asp | Ser | Gln | Ser | Pro | His | Ala |
| | | | 20 | | | | 25 | | | | | 30 | | | |
| His | Gly | Tyr | Ile | Pro | Ser | Lys | Phe | Pro | Asn | Lys | Asn | Leu | Lys | Met | Asn |
| | | 35 | | | | | 40 | | | | | 45 | | | |
| Tyr | Cys | Arg | Asn | Pro | Asp | Gly | Glu | Pro | Arg | Pro | Trp | Cys | Phe | Thr | Thr |
| | 50 | | | | | 55 | | | | | 60 | | | | |
| Asp | Pro | Gln | Lys | Arg | Trp | Glu | Phe | Cys | Asp | Ile | Pro | Arg | Cys | Thr | Thr |
| 65 | | | | | 70 | | | | | 75 | | | | | 80 |

-continued

| | | | | | | | | | | | | | | |
|---|---|---|---|---|---|---|---|---|---|---|---|---|---|---|
| Pro | Pro | Pro | Ser | Ser<br>85 | Gly | Pro | Lys | Tyr | Gln<br>90 | Cys | Leu | Lys | Gly | Thr<br>95 | Gly |
| Lys | Asn | Tyr | Gly<br>100 | Gly | Thr | Val | Ala | Val<br>105 | Thr | Glu | Ser | Gly | His<br>110 | Thr | Cys |
| Gln | Arg | Trp<br>115 | Ser | Glu | Gln | Thr | Pro<br>120 | His | Lys | His | Asn | Arg<br>125 | Thr | Pro | Glu |
| Asn | Phe<br>130 | Pro | Cys | Lys | Asn | Leu<br>135 | Glu | Glu | Asn | Tyr | Cys<br>140 | Arg | Asn | Pro | Asp |
| Gly<br>145 | Glu | Lys | Ala | Pro | Trp<br>150 | Cys | Tyr | Thr | Thr | Asn<br>155 | Ser | Glu | Val | Arg | Trp<br>160 |
| Glu | Tyr | Cys | Thr | Ile<br>165 | Pro | Ser | Cys | | | | | | | | |

(2) INFORMATION FOR SEQ ID NO:29:

(i) SEQUENCE CHARACTERISTICS:
        (A) LENGTH: 250 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Murine (vii) IMMEDIATE SOURCE:
        (B) CLONE: K1-3

(xi) SEQUENCE DESCRIPTION: SEQ ID NO:29:

| | | | | | | | | | | | | | | |
|---|---|---|---|---|---|---|---|---|---|---|---|---|---|---|
| Cys<br>1 | Lys | Thr | Gly | Ile<br>5 | Gly | Asn | Gly | Tyr | Arg<br>10 | Gly | Thr | Met | Ser | Arg<br>15 | Thr |
| Lys | Ser | Gly | Val<br>20 | Ala | Cys | Gln | Lys | Trp<br>25 | Gly | Ala | Thr | Phe | Pro<br>30 | His | Val |
| Pro | Asn | Tyr<br>35 | Ser | Pro | Ser | Thr | His<br>40 | Pro | Asn | Glu | Gly | Leu<br>45 | Glu | Glu | Asn |
| Tyr | Cys<br>50 | Arg | Asn | Pro | Asp | Asn<br>55 | Asp | Glu | Gln | Gly | Pro<br>60 | Trp | Cys | Tyr | Thr |
| Thr<br>65 | Asp | Pro | Asp | Lys | Arg<br>70 | Tyr | Asp | Tyr | Cys | Asn<br>75 | Ile | Pro | Glu | Cys | Glu<br>80 |
| Glu | Glu | Cys | Met | Tyr<br>85 | Cys | Ser | Gly | Glu | Lys<br>90 | Tyr | Glu | Gly | Lys | Ile<br>95 | Ser |
| Lys | Thr | Met | Ser<br>100 | Gly | Leu | Asp | Cys | Gln<br>105 | Ala | Trp | Asp | Ser | Gln<br>110 | Ser | Pro |
| His | Ala | His<br>115 | Gly | Tyr | Ile | Pro | Ala<br>120 | Lys | Phe | Pro | Ser | Lys<br>125 | Asn | Leu | Lys |
| Met | Asn | Tyr<br>130 | Cys | His | Asn | Pro | Asp<br>135 | Gly | Glu | Pro | Arg | Pro<br>140 | Trp | Cys | Phe |
| Thr<br>145 | Thr | Asp | Pro | Thr | Lys<br>150 | Arg | Trp | Glu | Tyr | Cys<br>155 | Asp | Ile | Pro | Arg | Cys<br>160 |
| Thr | Thr | Pro | Pro | Pro<br>165 | Pro | Pro | Ser | Pro | Thr<br>170 | Tyr | Gln | Cys | Leu | Lys<br>175 | Gly |
| Arg | Gly | Glu | Asn<br>180 | Tyr | Arg | Gly | Thr | Val<br>185 | Ser | Val | Thr | Val | Ser<br>190 | Gly | Lys |

```
Thr Cys Gln Arg Trp Ser Glu Gln Thr Pro His Arg His Asn Arg Thr
        195                 200                 205

Pro Glu Asn Phe Pro Cys Lys Asn Leu Glu Glu Asn Tyr Cys Arg Asn
    210                 215                 220

Pro Asp Gly Glu Thr Ala Pro Trp Cys Tyr Thr Thr Asp Ser Gln Leu
225                 230                 235                 240

Arg Trp Glu Tyr Cys Glu Ile Pro Ser Cys
                245                 250
```

( 2 ) INFORMATION FOR SEQ ID NO:30:

( i ) SEQUENCE CHARACTERISTICS:
        ( A ) LENGTH: 250 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K1-3

( x i ) SEQUENCE DESCRIPTION: SEQ ID NO:30:

```
Cys Lys Thr Gly Asn Gly Lys Asn Tyr Arg Gly Thr Met Ser Lys Thr
1               5                   10                  15

Lys Asn Gly Ile Thr Cys Gln Lys Trp Ser Ser Thr Ser Pro His Arg
                20                  25                  30

Pro Arg Phe Ser Pro Ala Thr His Pro Ser Glu Gly Leu Glu Glu Asn
            35                  40                  45

Tyr Cys Arg Asn Pro Asp Asn Asp Pro Gln Gly Pro Trp Cys Tyr Thr
    50                  55                  60

Thr Asp Pro Glu Lys Arg Tyr Asp Tyr Cys Asp Ile Leu Glu Cys Glu
65                  70                  75                  80

Glu Glu Cys Met His Cys Ser Gly Glu Asn Tyr Asp Gly Lys Ile Ser
                85                  90                  95

Lys Thr Met Ser Gly Leu Glu Cys Gln Ala Trp Asp Ser Gln Ser Pro
            100                 105                 110

His Ala His Gly Tyr Ile Pro Ser Lys Phe Pro Asn Lys Asn Leu Lys
        115                 120                 125

Lys Asn Tyr Cys Arg Asn Pro Asp Arg Glu Leu Arg Pro Trp Cys Phe
    130                 135                 140

Thr Thr Asp Pro Asn Lys Arg Trp Glu Leu Cys Asp Ile Pro Arg Cys
145                 150                 155                 160

Thr Thr Pro Pro Pro Ser Ser Gly Pro Thr Tyr Gln Cys Leu Lys Gly
                165                 170                 175

Thr Gly Glu Asn Tyr Arg Gly Asn Val Ala Val Thr Val Ser Gly His
            180                 185                 190

Thr Cys Gln His Trp Ser Ala Gln Thr Pro His Thr His Asn Arg Thr
        195                 200                 205

Pro Glu Asn Phe Pro Cys Lys Asn Leu Asp Glu Asn Tyr Cys Arg Asn
    210                 215                 220

Pro Asp Gly Lys Arg Ala Pro Trp Cys His Thr Thr Asn Ser Gln Val
```

5,837,682

225 230 235 240

Arg Trp Glu Tyr Cys Lys Ile Pro Ser Cys
          245                       250

(2) INFORMATION FOR SEQ ID NO:31:

(i) SEQUENCE CHARACTERISTICS:
        (A) LENGTH: 250 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rhesus monkey (vii) IMMEDIATE SOURCE:
        (B) CLONE: K1-3

(xi) SEQUENCE DESCRIPTION: SEQ ID NO:31:

Cys Lys Thr Gly Asn Gly Lys Asn Tyr Arg Gly Thr Met Ser Lys Thr
1               5                   10                  15

Arg Thr Gly Ile Thr Cys Gln Lys Trp Ser Ser Thr Ser Pro His Arg
            20                  25                  30

Pro Thr Phe Ser Pro Ala Thr His Pro Ser Glu Gly Leu Glu Glu Asn
        35                  40              45

Tyr Cys Arg Asn Pro Asp Asn Asp Gly Gln Gly Pro Trp Cys Tyr Thr
    50              55                      60

Thr Asp Pro Glu Glu Arg Phe Asp Tyr Cys Asp Ile Pro Glu Cys Glu
65              70                  75                      80

Asp Glu Cys Met His Cys Ser Gly Glu Asn Tyr Asp Gly Lys Ile Ser
                85                  90                  95

Lys Thr Met Ser Gly Leu Glu Cys Gln Ala Trp Asp Ser Gln Ser Pro
            100                 105                 110

His Ala His Gly Tyr Ile Pro Ser Lys Phe Pro Asn Lys Asn Leu Lys
        115                 120                 125

Lys Asn Tyr Cys Arg Asn Pro Asp Gly Glu Pro Arg Pro Trp Cys Phe
    130                 135                 140

Thr Thr Asp Pro Asn Lys Arg Trp Glu Leu Cys Asp Ile Pro Arg Cys
145             150                 155                 160

Thr Thr Pro Pro Pro Ser Ser Gly Pro Thr Tyr Gln Cys Leu Lys Gly
                165                 170                 175

Thr Gly Glu Asn Tyr Arg Gly Asp Val Ala Val Thr Val Ser Gly His
            180                 185                 190

Thr Cys His Gly Trp Ser Ala Gln Thr Pro His Thr His Asn Arg Thr
        195                 200                 205

Pro Glu Asn Phe Pro Cys Lys Asn Leu Asp Glu Asn Tyr Cys Arg Asn
    210                 215                 220

Pro Asp Gly Glu Lys Ala Pro Trp Cys Tyr Thr Thr Asn Ser Gln Val
225                 230                 235                 240

Arg Trp Glu Tyr Cys Lys Ile Pro Ser Cys
          245                       250

(2) INFORMATION FOR SEQ ID NO:32:

( i ) SEQUENCE CHARACTERISTICS:
  ( A ) LENGTH: 250 amino acids
  ( B ) TYPE: amino acid
  ( C ) STRANDEDNESS:
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
  ( A ) ORGANISM: Porcine ( v i i ) IMMEDIATE SOURCE:
  ( B ) CLONE: K1-3

( x i ) SEQUENCE DESCRIPTION: SEQ ID NO:32:

| Cys | Lys | Thr | Gly | Asn | Gly | Lys | Asn | Tyr | Arg | Gly | Thr | Thr | Ser | Lys | Thr |
|---|---|---|---|---|---|---|---|---|---|---|---|---|---|---|---|
| 1 | | | | 5 | | | | | 10 | | | | | 15 | |
| Lys | Ser | Gly | Val | Ile | Cys | Gln | Lys | Trp | Ser | Val | Ser | Ser | Pro | His | Ile |
| | | | 20 | | | | 25 | | | | | | 30 | | |
| Pro | Lys | Tyr | Ser | Pro | Glu | Lys | Phe | Pro | Leu | Ala | Gly | Leu | Glu | Glu | Asn |
| | | 35 | | | | | 40 | | | | | 45 | | | |
| Tyr | Cys | Arg | Asn | Pro | Asp | Asn | Asp | Glu | Lys | Gly | Pro | Trp | Cys | Tyr | Thr |
| | 50 | | | | | 55 | | | | | 60 | | | | |
| Thr | Asp | Pro | Glu | Thr | Arg | Phe | Asp | Tyr | Cys | Asp | Ile | Pro | Glu | Cys | Glu |
| 65 | | | | | 70 | | | | | 75 | | | | | 80 |
| Asp | Glu | Cys | Met | His | Cys | Ser | Gly | Glu | His | Tyr | Glu | Gly | Lys | Ile | Ser |
| | | | | 85 | | | | | 90 | | | | | 95 | |
| Lys | Thr | Met | Ser | Gly | Ile | Glu | Cys | Gln | Ser | Trp | Gly | Ser | Gln | Ser | Pro |
| | | | | 100 | | | | 105 | | | | | 110 | | |
| His | Ala | His | Gly | Tyr | Leu | Pro | Ser | Lys | Phe | Pro | Asn | Lys | Asn | Leu | Lys |
| | | | 115 | | | | 120 | | | | | 125 | | | |
| Met | Asn | Tyr | Cys | Arg | Asn | Pro | Asp | Gly | Glu | Pro | Arg | Pro | Trp | Cys | Phe |
| | 130 | | | | | 135 | | | | | 140 | | | | |
| Thr | Thr | Asp | Pro | Asn | Lys | Arg | Trp | Glu | Phe | Cys | Asp | Ile | Pro | Arg | Cys |
| 145 | | | | | 150 | | | | | 155 | | | | | 160 |
| Thr | Thr | Pro | Pro | Pro | Thr | Ser | Gly | Pro | Thr | Tyr | Gln | Cys | Leu | Lys | Gly |
| | | | | 165 | | | | | 170 | | | | | 175 | |
| Arg | Gly | Glu | Asn | Tyr | Arg | Gly | Thr | Val | Ser | Val | Thr | Ala | Ser | Gly | His |
| | | | 180 | | | | | 185 | | | | | | 190 | |
| Thr | Cys | Gln | Arg | Trp | Ser | Ala | Gln | Ser | Pro | His | Lys | His | Asn | Arg | Thr |
| | | | 195 | | | | | 200 | | | | 205 | | | |
| Pro | Glu | Asn | Phe | Pro | Cys | Lys | Asn | Leu | Glu | Glu | Asn | Tyr | Cys | Arg | Asn |
| | | 210 | | | | | 215 | | | | 220 | | | | |
| Pro | Asp | Gly | Glu | Thr | Ala | Pro | Trp | Cys | Tyr | Thr | Thr | Asp | Ser | Glu | Val |
| 225 | | | | | 230 | | | | | 235 | | | | | 240 |
| Arg | Trp | Asp | Tyr | Cys | Lys | Ile | Pro | Ser | Cys | | | | | | |
| | | | | 245 | | | | | 250 | | | | | | |

( 2 ) INFORMATION FOR SEQ ID NO:33:

( i ) SEQUENCE CHARACTERISTICS:
  ( A ) LENGTH: 250 amino acids
  ( B ) TYPE: amino acid
  ( C ) STRANDEDNESS:
  ( D ) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
    (A) ORGANISM: Bovine (v i i) IMMEDIATE SOURCE:
    (B) CLONE: K1-3

(x i) SEQUENCE DESCRIPTION: SEQ ID NO:33:

| Cys | Lys | Thr | Gly | Asn | Gly | Gln | Thr | Tyr | Arg | Gly | Thr | Thr | Ala | Glu | Thr |
|---|---|---|---|---|---|---|---|---|---|---|---|---|---|---|---|
| 1 | | | | 5 | | | | | 10 | | | | | 15 | |
| Lys | Ser | Gly | Val | Thr | Cys | Gln | Lys | Trp | Ser | Ala | Thr | Ser | Pro | His | Val |
| | | | 20 | | | | 25 | | | | | | 30 | | |
| Pro | Lys | Phe | Ser | Pro | Glu | Lys | Phe | Pro | Leu | Ala | Gly | Leu | Glu | Glu | Asn |
| | | 35 | | | | | 40 | | | | | 45 | | | |
| Tyr | Cys | Arg | Asn | Pro | Asp | Asn | Asp | Glu | Asn | Gly | Pro | Trp | Cys | Tyr | Thr |
| | 50 | | | | | 55 | | | | | 60 | | | | |
| Thr | Asp | Pro | Asp | Lys | Arg | Tyr | Asp | Tyr | Cys | Asp | Ile | Pro | Glu | Cys | Glu |
| 65 | | | | | 70 | | | | | 75 | | | | | 80 |
| Asp | Lys | Cys | Met | His | Cys | Ser | Gly | Glu | Asn | Tyr | Glu | Gly | Lys | Ile | Ala |
| | | | | 85 | | | | | 90 | | | | | 95 | |
| Lys | Thr | Met | Ser | Gly | Arg | Asp | Cys | Gln | Ala | Trp | Asp | Ser | Gln | Ser | Pro |
| | | | 100 | | | | | 105 | | | | | 110 | | |
| His | Ala | His | Gly | Tyr | Ile | Pro | Ser | Lys | Phe | Pro | Asn | Lys | Asn | Leu | Lys |
| | | 115 | | | | | 120 | | | | | 125 | | | |
| Met | Asn | Tyr | Cys | Arg | Asn | Pro | Asp | Gly | Glu | Pro | Arg | Pro | Trp | Cys | Phe |
| | 130 | | | | | 135 | | | | | 140 | | | | |
| Thr | Thr | Asp | Pro | Gln | Lys | Arg | Trp | Glu | Phe | Cys | Asp | Ile | Pro | Arg | Cys |
| 145 | | | | | 150 | | | | | 155 | | | | | 160 |
| Thr | Thr | Pro | Pro | Pro | Ser | Ser | Gly | Pro | Lys | Tyr | Gln | Cys | Leu | Lys | Gly |
| | | | | 165 | | | | | 170 | | | | | 175 | |
| Thr | Gly | Lys | Asn | Tyr | Gly | Gly | Thr | Val | Ala | Val | Thr | Glu | Ser | Gly | His |
| | | | 180 | | | | | 185 | | | | | 190 | | |
| Thr | Cys | Gln | Arg | Trp | Ser | Glu | Gln | Thr | Pro | His | Lys | His | Asn | Arg | Thr |
| | | 195 | | | | | 200 | | | | | 205 | | | |
| Pro | Glu | Asn | Phe | Pro | Cys | Lys | Asn | Leu | Glu | Glu | Asn | Tyr | Cys | Arg | Asn |
| | 210 | | | | | 215 | | | | | 220 | | | | |
| Pro | Asp | Gly | Glu | Lys | Ala | Pro | Trp | Cys | Tyr | Thr | Thr | Asn | Ser | Glu | Val |
| 225 | | | | | 230 | | | | | 235 | | | | | 240 |
| Arg | Trp | Glu | Tyr | Cys | Thr | Ile | Pro | Ser | Cys | | | | | | |
| | | | | 245 | | | | | 250 | | | | | | |

(2) INFORMATION FOR SEQ ID NO:34:

(i) SEQUENCE CHARACTERISTICS:
    (A) LENGTH: 160 amino acids
    (B) TYPE: amino acid
    (C) STRANDEDNESS:
    (D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
(A) ORGANISM: Murine (v i i) IMMEDIATE SOURCE:
(B) CLONE: K1-2

(x i) SEQUENCE DESCRIPTION: SEQ ID NO:34:

| Cys | Lys | Thr | Gly | Ile | Gly | Asn | Gly | Tyr | Arg | Gly | Thr | Met | Ser | Arg | Thr |
|---|---|---|---|---|---|---|---|---|---|---|---|---|---|---|---|
| 1 | | | | 5 | | | | | 10 | | | | | 15 | |
| Lys | Ser | Gly | Val | Ala | Cys | Gln | Lys | Trp | Gly | Ala | Thr | Phe | Pro | His | Val |
| | | | 20 | | | | 25 | | | | | | 30 | | |
| Pro | Asn | Tyr | Ser | Pro | Ser | Thr | His | Pro | Asn | Glu | Gly | Leu | Glu | Glu | Asn |
| | | 35 | | | | | 40 | | | | | 45 | | | |
| Tyr | Cys | Arg | Asn | Pro | Asp | Asn | Asp | Glu | Gln | Gly | Pro | Trp | Cys | Tyr | Thr |
| | 50 | | | | | 55 | | | | | 60 | | | | |
| Thr | Asp | Pro | Asp | Lys | Arg | Tyr | Asp | Tyr | Cys | Asn | Ile | Pro | Glu | Cys | Glu |
| 65 | | | | | 70 | | | | | 75 | | | | | 80 |
| Glu | Glu | Cys | Met | Tyr | Cys | Ser | Gly | Glu | Lys | Tyr | Glu | Gly | Lys | Ile | Ser |
| | | | | 85 | | | | | 90 | | | | | 95 | |
| Lys | Thr | Met | Ser | Gly | Leu | Asp | Cys | Gln | Ala | Trp | Asp | Ser | Gln | Ser | Pro |
| | | | 100 | | | | | 105 | | | | | 110 | | |
| His | Ala | His | Gly | Tyr | Ile | Pro | Ala | Lys | Phe | Pro | Ser | Lys | Asn | Leu | Lys |
| | | 115 | | | | | 120 | | | | | 125 | | | |
| Met | Asn | Tyr | Cys | His | Asn | Pro | Asp | Gly | Glu | Pro | Arg | Pro | Trp | Cys | Phe |
| | 130 | | | | | 135 | | | | | 140 | | | | |
| Thr | Thr | Asp | Pro | Thr | Lys | Arg | Trp | Glu | Tyr | Cys | Asp | Ile | Pro | Arg | Cys |
| 145 | | | | | 150 | | | | | 155 | | | | | 160 |

(2) INFORMATION FOR SEQ ID NO:35:

(i) SEQUENCE CHARACTERISTICS:
(A) LENGTH: 160 amino acids
(B) TYPE: amino acid
(C) STRANDEDNESS:
(D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
(A) ORGANISM: Homo sapiens (v i i) IMMEDIATE SOURCE:
(B) CLONE: K1-2

(x i) SEQUENCE DESCRIPTION: SEQ ID NO:35:

| Cys | Lys | Thr | Gly | Asn | Gly | Lys | Asn | Tyr | Arg | Gly | Thr | Met | Ser | Lys | Thr |
|---|---|---|---|---|---|---|---|---|---|---|---|---|---|---|---|
| 1 | | | | 5 | | | | | 10 | | | | | 15 | |
| Lys | Asn | Gly | Ile | Thr | Cys | Gln | Lys | Trp | Ser | Ser | Thr | Ser | Pro | His | Arg |
| | | | 20 | | | | 25 | | | | | | 30 | | |
| Pro | Arg | Phe | Ser | Pro | Ala | Thr | His | Pro | Ser | Glu | Gly | Leu | Glu | Glu | Asn |
| | | 35 | | | | | 40 | | | | | 45 | | | |
| Tyr | Cys | Arg | Asn | Pro | Asp | Asn | Asp | Pro | Gln | Gly | Pro | Trp | Cys | Tyr | Thr |
| | 50 | | | | | 55 | | | | | 60 | | | | |
| Thr | Asp | Pro | Glu | Lys | Arg | Tyr | Asp | Tyr | Cys | Asp | Ile | Leu | Glu | Cys | Glu |
| 65 | | | | | 70 | | | | | 75 | | | | | 80 |
| Glu | Glu | Cys | Met | His | Cys | Ser | Gly | Glu | Asn | Tyr | Asp | Gly | Lys | Ile | Ser |

| | | | | 85 | | | | 90 | | | | 95 | | |
|---|---|---|---|---|---|---|---|---|---|---|---|---|---|---|
| Lys | Thr | Met | Ser<br>100 | Gly | Leu | Glu | Cys | Gln<br>105 | Ala | Trp | Asp | Ser | Gln<br>110 | Ser | Pro |
| His | Ala | His<br>115 | Gly | Tyr | Ile | Pro | Ser<br>120 | Lys | Phe | Pro | Asn | Lys<br>125 | Asn | Leu | Lys |
| Lys | Asn<br>130 | Tyr | Cys | Arg | Asn | Pro<br>135 | Asp | Arg | Glu | Leu | Arg<br>140 | Pro | Trp | Cys | Phe |
| Thr<br>145 | Thr | Asp | Pro | Asn | Lys<br>150 | Arg | Trp | Glu | Leu | Cys<br>155 | Asp | Ile | Pro | Arg | Cys<br>160 |

( 2 ) INFORMATION FOR SEQ ID NO:36:

( i ) SEQUENCE CHARACTERISTICS:
        ( A ) LENGTH: 160 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rhesus monkey ( v i i ) IMMEDIATE SOURCE:
        ( B ) CLONE: K1-2

( x i ) SEQUENCE DESCRIPTION: SEQ ID NO:36:

| Cys<br>1 | Lys | Thr | Gly | Asn<br>5 | Gly | Lys | Asn | Tyr | Arg<br>10 | Gly | Thr | Met | Ser | Lys<br>15 | Thr |
|---|---|---|---|---|---|---|---|---|---|---|---|---|---|---|---|
| Arg | Thr | Gly | Ile<br>20 | Thr | Cys | Gln | Lys | Trp<br>25 | Ser | Ser | Thr | Ser | Pro<br>30 | His | Arg |
| Pro | Thr | Phe<br>35 | Ser | Pro | Ala | Thr | His<br>40 | Pro | Ser | Glu | Gly | Leu<br>45 | Glu | Glu | Asn |
| Tyr | Cys<br>50 | Arg | Asn | Pro | Asp | Asn<br>55 | Asp | Gly | Gln | Gly | Pro<br>60 | Trp | Cys | Tyr | Thr |
| Thr<br>65 | Asp | Pro | Glu | Glu | Arg<br>70 | Phe | Asp | Tyr | Cys | Asp<br>75 | Ile | Pro | Glu | Cys | Glu<br>80 |
| Asp | Glu | Cys | Met | His<br>85 | Cys | Ser | Gly | Glu | Asn<br>90 | Tyr | Asp | Gly | Lys | Ile<br>95 | Ser |
| Lys | Thr | Met | Ser<br>100 | Gly | Leu | Glu | Cys | Gln<br>105 | Ala | Trp | Asp | Ser | Gln<br>110 | Ser | Pro |
| His | Ala | His<br>115 | Gly | Tyr | Ile | Pro | Ser<br>120 | Lys | Phe | Pro | Asn | Lys<br>125 | Asn | Leu | Lys |
| Lys | Asn<br>130 | Tyr | Cys | Arg | Asn | Pro<br>135 | Asp | Gly | Glu | Pro | Arg<br>140 | Pro | Trp | Cys | Phe |
| Thr<br>145 | Thr | Asp | Pro | Asn | Lys<br>150 | Arg | Trp | Glu | Leu | Cys<br>155 | Asp | Ile | Pro | Arg | Cys<br>160 |

( 2 ) INFORMATION FOR SEQ ID NO:37:

( i ) SEQUENCE CHARACTERISTICS:
        ( A ) LENGTH: 160 amino acids
        ( B ) TYPE: amino acid
        ( C ) STRANDEDNESS:
        ( D ) TOPOLOGY: linear ( i i ) MOLECULE TYPE: protein (i i i) HYPOTHETICAL: NO (i v) ANTI-SENSE: NO (v) FRAGMENT TYPE: N-terminal (v i) ORIGINAL SOURCE:
 (A) ORGANISM: Porcine (v i i) IMMEDIATE SOURCE:
 (B) CLONE: K1-2

(x i) SEQUENCE DESCRIPTION: SEQ ID NO:37:

```
Cys Lys Thr Gly Asn Gly Lys Asn Tyr Arg Gly Thr Thr Ser Lys Thr
1               5                   10                  15

Lys Ser Gly Val Ile Cys Gln Lys Trp Ser Val Ser Ser Pro His Ile
            20              25                  30

Pro Lys Tyr Ser Pro Glu Lys Phe Pro Leu Ala Gly Leu Glu Glu Asn
        35              40                  45

Tyr Cys Arg Asn Pro Asp Asn Asp Glu Lys Gly Pro Trp Cys Tyr Thr
    50              55                  60

Thr Asp Pro Glu Thr Arg Phe Asp Tyr Cys Asp Ile Pro Glu Cys Glu
65              70                  75                  80

Asp Glu Cys Met His Cys Ser Gly Glu His Tyr Glu Gly Lys Ile Ser
                85                  90                  95

Lys Thr Met Ser Gly Ile Glu Cys Gln Ser Trp Gly Ser Gln Ser Pro
            100             105                 110

His Ala His Gly Tyr Leu Pro Ser Lys Phe Pro Asn Lys Asn Leu Lys
        115             120                 125

Met Asn Tyr Cys Arg Asn Pro Asp Gly Glu Pro Arg Pro Trp Cys Phe
    130             135                 140

Thr Thr Asp Pro Asn Lys Arg Trp Glu Phe Cys Asp Ile Pro Arg Cys
145             150                 155                 160
```

(2) INFORMATION FOR SEQ ID NO:38:

(i) SEQUENCE CHARACTERISTICS:
  (A) LENGTH: 160 amino acids
  (B) TYPE: amino acid
  (C) STRANDEDNESS:
  (D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
  (A) ORGANISM: Bovine (v i i) IMMEDIATE SOURCE:
  (B) CLONE: K1-2

(x i) SEQUENCE DESCRIPTION: SEQ ID NO:38:

```
Cys Lys Thr Gly Asn Gly Gln Thr Tyr Arg Gly Thr Thr Ala Glu Thr
1               5                   10                  15

Lys Ser Gly Val Thr Cys Gln Lys Trp Ser Ala Thr Ser Pro His Val
            20              25                  30

Pro Lys Phe Ser Pro Glu Lys Phe Pro Leu Ala Gly Leu Glu Glu Asn
        35              40                  45

Tyr Cys Arg Asn Pro Asp Asn Asp Glu Asn Gly Pro Trp Cys Tyr Thr
    50              55                  60
```

| | | | | | | | | | | | | | | | |
|---|---|---|---|---|---|---|---|---|---|---|---|---|---|---|---|
| Thr<br>65 | Asp | Pro | Asp | Lys | Arg<br>70 | Tyr | Asp | Tyr | Cys | Asp<br>75 | Ile | Pro | Glu | Cys | Glu<br>80 |
| Asp | Lys | Cys | Met | His<br>85 | Cys | Ser | Gly | Glu | Asn<br>90 | Tyr | Glu | Gly | Lys | Ile<br>95 | Ala |
| Lys | Thr | Met | Ser<br>100 | Gly | Arg | Asp | Cys | Gln<br>105 | Ala | Trp | Asp | Ser | Gln<br>110 | Ser | Pro |
| His | Ala | His<br>115 | Gly | Tyr | Ile | Pro | Ser<br>120 | Lys | Phe | Pro | Asn | Lys<br>125 | Asn | Leu | Lys |
| Met | Asn<br>130 | Tyr | Cys | Arg | Asn | Pro<br>135 | Asp | Gly | Glu | Pro | Arg<br>140 | Pro | Trp | Cys | Phe |
| Thr<br>145 | Thr | Asp | Pro | Gln | Lys<br>150 | Arg | Trp | Glu | Phe | Cys<br>155 | Asp | Ile | Pro | Arg | Cys<br>160 |

( 2 ) INFORMATION FOR SEQ ID NO:39:

( i ) SEQUENCE CHARACTERISTICS:
        ( A ) LENGTH: 352 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Murine ( v i i ) IMMEDIATE SOURCE:
        ( B ) CLONE: K1-4

( x i ) SEQUENCE DESCRIPTION: SEQ ID NO:39:

| | | | | | | | | | | | | | | | |
|---|---|---|---|---|---|---|---|---|---|---|---|---|---|---|---|
| Cys<br>1 | Lys | Thr | Gly | Ile<br>5 | Gly | Asn | Gly | Tyr | Arg<br>10 | Gly | Thr | Met | Ser | Arg<br>15 | Thr |
| Lys | Ser | Gly | Val<br>20 | Ala | Cys | Gln | Lys | Trp<br>25 | Gly | Ala | Thr | Phe | Pro<br>30 | His | Val |
| Pro | Asn | Tyr<br>35 | Ser | Pro | Ser | Thr | His<br>40 | Pro | Asn | Glu | Gly | Leu<br>45 | Glu | Glu | Asn |
| Tyr | Cys<br>50 | Arg | Asn | Pro | Asp | Asn<br>55 | Asp | Glu | Gln | Gly | Pro<br>60 | Trp | Cys | Tyr | Thr |
| Thr<br>65 | Asp | Pro | Asp | Lys | Arg<br>70 | Tyr | Asp | Tyr | Cys | Asn<br>75 | Ile | Pro | Glu | Cys | Glu<br>80 |
| Glu | Glu | Cys | Met | Tyr<br>85 | Cys | Ser | Gly | Glu | Lys<br>90 | Tyr | Glu | Gly | Lys | Ile<br>95 | Ser |
| Lys | Thr | Met | Ser<br>100 | Gly | Leu | Asp | Cys | Gln<br>105 | Ala | Trp | Asp | Ser | Gln<br>110 | Ser | Pro |
| His | Ala | His<br>115 | Gly | Tyr | Ile | Pro | Ala<br>120 | Lys | Phe | Pro | Ser | Lys<br>125 | Asn | Leu | Lys |
| Met | Asn<br>130 | Tyr | Cys | His | Asn | Pro<br>135 | Asp | Gly | Glu | Pro | Arg<br>140 | Pro | Trp | Cys | Phe |
| Thr<br>145 | Thr | Asp | Pro | Thr | Lys<br>150 | Arg | Trp | Glu | Tyr | Cys<br>155 | Asp | Ile | Pro | Arg | Cys<br>160 |
| Thr | Thr | Pro | Pro | Pro<br>165 | Pro | Pro | Ser | Pro | Thr<br>170 | Tyr | Gln | Cys | Leu | Lys<br>175 | Gly |
| Arg | Gly | Glu | Asn<br>180 | Tyr | Arg | Gly | Thr | Val<br>185 | Ser | Val | Thr | Val | Ser<br>190 | Gly | Lys |

```
Thr  Cys  Gln  Arg  Trp  Ser  Glu  Gln  Thr  Pro  His  Arg  His  Asn  Arg  Thr
          195                      200                      205

Pro  Glu  Asn  Phe  Pro  Cys  Lys  Asn  Leu  Glu  Glu  Asn  Tyr  Cys  Arg  Asn
     210                      215                      220

Pro  Asp  Gly  Glu  Thr  Ala  Pro  Trp  Cys  Tyr  Thr  Thr  Asp  Ser  Gln  Leu
225                      230                      235                      240

Arg  Trp  Glu  Tyr  Cys  Glu  Ile  Pro  Ser  Cys  Glu  Ser  Ser  Ala  Ser  Pro
               245                      250                      255

Asp  Gln  Ser  Asp  Ser  Ser  Val  Pro  Pro  Glu  Gln  Thr  Pro  Val  Val
               260                      265                      270

Gln  Glu  Cys  Tyr  Gln  Ser  Asp  Gly  Gln  Ser  Tyr  Arg  Gly  Thr  Ser  Ser
          275                      280                      285

Thr  Thr  Ile  Thr  Gly  Lys  Lys  Cys  Gln  Ser  Trp  Ala  Ala  Met  Phe  Pro
     290                      295                      300

His  Arg  His  Ser  Lys  Thr  Pro  Glu  Asn  Phe  Pro  Asp  Ala  Gly  Leu  Glu
305                      310                      315                      320

Met  Asn  Tyr  Cys  Arg  Asn  Pro  Asp  Gly  Asp  Lys  Gly  Pro  Trp  Cys  Tyr
               325                      330                      335

Thr  Thr  Asp  Pro  Ser  Val  Arg  Trp  Glu  Tyr  Cys  Asn  Leu  Lys  Arg  Cys
               340                      345                      350
```

( 2 ) INFORMATION FOR SEQ ID NO:40:

( i ) SEQUENCE CHARACTERISTICS:
        ( A ) LENGTH: 352 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K1-4

( x i ) SEQUENCE DESCRIPTION: SEQ ID NO:40:

```
Cys  Lys  Thr  Gly  Asn  Gly  Lys  Asn  Tyr  Arg  Gly  Thr  Met  Ser  Lys  Thr
1                   5                        10                      15

Lys  Asn  Gly  Ile  Thr  Cys  Gln  Lys  Trp  Ser  Ser  Thr  Ser  Pro  His  Arg
               20                      25                      30

Pro  Arg  Phe  Ser  Pro  Ala  Thr  His  Pro  Ser  Glu  Gly  Leu  Glu  Glu  Asn
          35                      40                      45

Tyr  Cys  Arg  Asn  Pro  Asp  Asn  Asp  Pro  Gln  Gly  Pro  Trp  Cys  Tyr  Thr
     50                      55                      60

Thr  Asp  Pro  Glu  Lys  Arg  Tyr  Asp  Tyr  Cys  Asp  Ile  Leu  Glu  Cys  Glu
65                      70                      75                      80

Glu  Glu  Cys  Met  His  Cys  Ser  Gly  Glu  Asn  Tyr  Asp  Gly  Lys  Ile  Ser
               85                      90                      95

Lys  Thr  Met  Ser  Gly  Leu  Glu  Cys  Gln  Ala  Trp  Asp  Ser  Gln  Ser  Pro
               100                     105                     110

His  Ala  His  Gly  Tyr  Ile  Pro  Ser  Lys  Phe  Pro  Asn  Lys  Asn  Leu  Lys
               115                     120                     125

Lys  Asn  Tyr  Cys  Arg  Asn  Pro  Asp  Arg  Glu  Leu  Arg  Pro  Trp  Cys  Phe
```

|     |     |     |     |     | 130 |     |     |     |     | 135 |     |     |     |     | 140 |     |     |
| --- | --- | --- | --- | --- | --- | --- | --- | --- | --- | --- | --- | --- | --- | --- | --- | --- | --- |
| Thr 145 | Thr | Asp | Pro | Asn | Lys 150 | Arg | Trp | Glu | Leu | Cys 155 | Asp | Ile | Pro | Arg | Cys 160 | | |
| Thr | Thr | Pro | Pro | Pro 165 | Ser | Ser | Gly | Pro | Thr 170 | Tyr | Gln | Cys | Leu | Lys 175 | Gly | | |
| Thr | Gly | Glu | Asn 180 | Tyr | Arg | Gly | Asn | Val 185 | Ala | Val | Thr | Val | Ser 190 | Gly | His | | |
| Thr | Cys | Gln 195 | His | Trp | Ser | Ala | Gln 200 | Thr | Pro | His | Thr | His 205 | Asn | Arg | Thr | | |
| Pro | Glu 210 | Asn | Phe | Pro | Cys | Lys 215 | Asn | Leu | Asp | Glu | Asn 220 | Tyr | Cys | Arg | Asn | | |
| Pro 225 | Asp | Gly | Lys | Arg | Ala 230 | Pro | Trp | Cys | His | Thr 235 | Thr | Asn | Ser | Gln | Val 240 | | |
| Arg | Trp | Glu | Tyr | Cys 245 | Lys | Ile | Pro | Ser | Cys 250 | Asp | Ser | Ser | Pro | Val 255 | Ser | | |
| Thr | Glu | Gln | Leu 260 | Ala | Pro | Thr | Ala | Pro 265 | Pro | Glu | Leu | Thr | Pro 270 | Val | Val | | |
| Gln | Asp | Cys 275 | Tyr | His | Gly | Asp 280 | Gly | Gln | Ser | Tyr | Arg 285 | Gly | Thr | Ser | Ser | | |
| Thr | Thr 290 | Thr | Thr | Gly | Lys 295 | Lys | Cys | Gln | Ser | Trp 300 | Ser | Ser | Met | Thr | Pro | | |
| His 305 | Arg | His | Gln | Lys | Thr 310 | Pro | Glu | Asn | Tyr | Pro 315 | Asn | Ala | Gly | Leu | Thr 320 | | |
| Met | Asn | Tyr | Cys | Arg 325 | Asn | Pro | Asp | Ala | Asp 330 | Lys | Gly | Pro | Trp | Cys 335 | Phe | | |
| Thr | Thr | Asp | Pro 340 | Ser | Val | Arg | Trp | Glu 345 | Tyr | Cys | Asn | Leu | Lys 350 | Lys | Cys | | |

( 2 ) INFORMATION FOR SEQ ID NO:41:

( i ) SEQUENCE CHARACTERISTICS:
( A ) LENGTH: 378 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Murine ( v i i ) IMMEDIATE SOURCE:
( B ) CLONE: K1-4BKLS ( x i ) SEQUENCE DESCRIPTION: SEQ ID NO:41:

|     |     |     |     |     |     |     |     |     |     |     |     |     |     |     |
| --- | --- | --- | --- | --- | --- | --- | --- | --- | --- | --- | --- | --- | --- | --- |
| Leu 1 | Phe | Glu | Lys | Arg 5 | Val | Tyr | Leu | Ser | Glu 10 | Cys | Lys | Thr | Gly | Ile 15 | Gly |
| Asn | Gly | Tyr | Arg 20 | Gly | Thr | Met | Ser | Arg 25 | Thr | Lys | Ser | Gly | Val 30 | Ala | Cys |
| Gln | Lys | Trp 35 | Gly | Ala | Thr | Phe | Pro 40 | His | Val | Pro | Asn | Tyr 45 | Ser | Pro | Ser |
| Thr | His 50 | Pro | Asn | Glu | Gly | Leu 55 | Glu | Glu | Asn | Tyr | Cys 60 | Arg | Asn | Pro | Asp |
| Asn 65 | Asp | Glu | Gln | Gly | Pro 70 | Trp | Cys | Tyr | Thr | Thr 75 | Asp | Pro | Asp | Lys | Arg 80 |

| | | | | | | | | | | | | | | |
|---|---|---|---|---|---|---|---|---|---|---|---|---|---|---|
|Tyr|Asp|Tyr|Cys|Asn<br>85|Ile|Pro|Glu|Cys<br>90|Glu|Glu|Cys|Met|Tyr<br>95|Cys|
|Ser|Gly|Glu|Lys<br>100|Tyr|Glu|Gly|Lys|Ile<br>105|Ser|Lys|Thr|Met|Ser<br>110|Gly|Leu|
|Asp|Cys|Gln<br>115|Ala|Trp|Asp|Ser|Gln<br>120|Ser|Pro|His|Ala|His<br>125|Gly|Tyr|Ile|
|Pro|Ala<br>130|Lys|Phe|Pro|Ser|Lys<br>135|Asn|Leu|Lys|Met|Asn<br>140|Tyr|Cys|His|Asn|
|Pro<br>145|Asp|Gly|Glu|Pro|Arg<br>150|Pro|Trp|Cys|Phe|Thr<br>155|Thr|Asp|Pro|Thr|Lys<br>160|
|Arg|Trp|Glu|Tyr|Cys<br>165|Asp|Ile|Pro|Arg|Cys<br>170|Thr|Thr|Pro|Pro<br>175|Pro|
|Pro|Ser|Pro|Thr<br>180|Tyr|Gln|Cys|Leu|Lys<br>185|Gly|Arg|Gly|Glu|Asn<br>190|Tyr|Arg|
|Gly|Thr|Val<br>195|Ser|Val|Thr|Val|Ser<br>200|Gly|Lys|Thr|Cys|Gln<br>205|Arg|Trp|Ser|
|Glu|Gln<br>210|Thr|Pro|His|Arg|His<br>215|Asn|Arg|Thr|Pro|Glu<br>220|Asn|Phe|Pro|Cys|
|Lys<br>225|Asn|Leu|Glu|Glu|Asn<br>230|Tyr|Cys|Arg|Asn|Pro<br>235|Asp|Gly|Glu|Thr|Ala<br>240|
|Pro|Trp|Cys|Tyr|Thr<br>245|Thr|Asp|Ser|Gln|Leu<br>250|Arg|Trp|Glu|Tyr|Cys<br>255|Glu|
|Ile|Pro|Ser|Cys<br>260|Glu|Ser|Ser|Ala|Ser<br>265|Pro|Asp|Gln|Ser|Asp<br>270|Ser|Ser|
|Val|Pro|Pro<br>275|Glu|Glu|Gln|Thr|Pro<br>280|Val|Val|Gln|Glu|Cys<br>285|Tyr|Gln|Ser|
|Asp|Gly<br>290|Gln|Ser|Tyr|Arg|Gly<br>295|Thr|Ser|Ser|Thr|Thr<br>300|Ile|Thr|Gly|Lys|
|Lys<br>305|Cys|Gln|Ser|Trp|Ala<br>310|Ala|Met|Phe|Pro|His<br>315|Arg|His|Ser|Lys|Thr<br>320|
|Pro|Glu|Asn|Phe|Pro<br>325|Asp|Ala|Gly|Leu|Glu<br>330|Met|Asn|Tyr|Cys|Arg<br>335|Asn|
|Pro|Asp|Gly|Asp<br>340|Lys|Gly|Pro|Trp|Cys<br>345|Tyr|Thr|Thr|Asp|Pro<br>350|Ser|Val|
|Arg|Trp|Glu<br>355|Tyr|Cys|Asn|Leu|Lys<br>360|Arg|Cys|Ser|Glu|Thr<br>365|Gly|Gly|Ser|
|Val|Val<br>370|Glu|Leu|Pro|Thr|Val<br>375|Ser|Gln|Glu| | | | | | |

( 2 ) INFORMATION FOR SEQ ID NO:42:

( i ) SEQUENCE CHARACTERISTICS:
        ( A ) LENGTH: 378 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K1-4BKLS ( x i ) SEQUENCE DESCRIPTION: SEQ ID NO:42:

| Leu | Phe | Glu | Lys | Lys | Val | Tyr | Leu | Ser | Glu | Cys | Lys | Thr | Gly | Asn | Gly |
|---|---|---|---|---|---|---|---|---|---|---|---|---|---|---|---|
| 1 | | | | 5 | | | | | 10 | | | | | 15 | |
| Lys | Asn | Tyr | Arg | Gly | Thr | Met | Ser | Lys | Thr | Lys | Asn | Gly | Ile | Thr | Cys |
| | | | 20 | | | | | 25 | | | | | 30 | | |
| Gln | Lys | Trp | Ser | Ser | Thr | Ser | Pro | His | Arg | Pro | Arg | Phe | Ser | Pro | Ala |
| | | 35 | | | | | 40 | | | | | 45 | | | |
| Thr | His | Pro | Ser | Glu | Gly | Leu | Glu | Glu | Asn | Tyr | Cys | Arg | Asn | Pro | Asp |
| | | 50 | | | | 55 | | | | | 60 | | | | |
| Asn | Asp | Pro | Gln | Gly | Pro | Trp | Cys | Tyr | Thr | Thr | Asp | Pro | Glu | Lys | Arg |
| 65 | | | | | 70 | | | | 75 | | | | | | 80 |
| Tyr | Asp | Tyr | Cys | Asp | Ile | Leu | Glu | Cys | Glu | Glu | Cys | Met | His | Cys | |
| | | | | 85 | | | | | 90 | | | | 95 | | |
| Ser | Gly | Glu | Asn | Tyr | Asp | Gly | Lys | Ile | Ser | Lys | Thr | Met | Ser | Gly | Leu |
| | | | 100 | | | | | 105 | | | | | 110 | | |
| Glu | Cys | Gln | Ala | Trp | Asp | Ser | Gln | Ser | Pro | His | Ala | His | Gly | Tyr | Ile |
| | | 115 | | | | | 120 | | | | | 125 | | | |
| Pro | Ser | Lys | Phe | Pro | Asn | Lys | Asn | Leu | Lys | Lys | Asn | Tyr | Cys | Arg | Asn |
| | 130 | | | | | 135 | | | | | 140 | | | | |
| Pro | Asp | Arg | Glu | Leu | Arg | Pro | Trp | Cys | Phe | Thr | Thr | Asp | Pro | Asn | Lys |
| 145 | | | | | 150 | | | | | 155 | | | | | 160 |
| Arg | Trp | Glu | Leu | Cys | Asp | Ile | Pro | Arg | Cys | Thr | Thr | Pro | Pro | Pro | Ser |
| | | | | 165 | | | | | 170 | | | | | 175 | |
| Ser | Gly | Pro | Thr | Tyr | Gln | Cys | Leu | Lys | Gly | Thr | Gly | Glu | Asn | Tyr | Arg |
| | | | 180 | | | | | 185 | | | | | 190 | | |
| Gly | Asn | Val | Ala | Val | Thr | Val | Ser | Gly | His | Thr | Cys | Gln | His | Trp | Ser |
| | | 195 | | | | | 200 | | | | | 205 | | | |
| Ala | Gln | Thr | Pro | His | Thr | His | Asn | Arg | Thr | Pro | Glu | Asn | Phe | Pro | Cys |
| | 210 | | | | | 215 | | | | | 220 | | | | |
| Lys | Asn | Leu | Asp | Glu | Asn | Tyr | Cys | Arg | Asn | Pro | Asp | Gly | Lys | Arg | Ala |
| 225 | | | | | 230 | | | | | 235 | | | | | 240 |
| Pro | Trp | Cys | His | Thr | Thr | Asn | Ser | Gln | Val | Arg | Trp | Glu | Tyr | Cys | Lys |
| | | | | 245 | | | | | 250 | | | | | 255 | |
| Ile | Pro | Ser | Cys | Asp | Ser | Ser | Pro | Val | Ser | Thr | Glu | Gln | Leu | Ala | Pro |
| | | | 260 | | | | | 265 | | | | | 270 | | |
| Thr | Ala | Pro | Pro | Glu | Leu | Thr | Pro | Val | Val | Gln | Asp | Cys | Tyr | His | Gly |
| | | 275 | | | | | 280 | | | | | 285 | | | |
| Asp | Gly | Gln | Ser | Tyr | Arg | Gly | Thr | Ser | Ser | Thr | Thr | Thr | Thr | Gly | Lys |
| | 290 | | | | | 295 | | | | | 300 | | | | |
| Lys | Cys | Gln | Ser | Trp | Ser | Ser | Met | Thr | Pro | His | Arg | His | Gln | Lys | Thr |
| 305 | | | | | 310 | | | | | 315 | | | | | 320 |
| Pro | Glu | Asn | Tyr | Pro | Asn | Ala | Gly | Leu | Thr | Met | Asn | Tyr | Cys | Arg | Asn |
| | | | | 325 | | | | | 330 | | | | | 335 | |
| Pro | Asp | Ala | Asp | Lys | Gly | Pro | Trp | Cys | Phe | Thr | Thr | Asp | Pro | Ser | Val |
| | | | 340 | | | | | 345 | | | | | 350 | | |
| Arg | Trp | Glu | Tyr | Cys | Asn | Leu | Lys | Lys | Cys | Ser | Gly | Thr | Glu | Ala | Ser |
| | | | 355 | | | | | 360 | | | | | 365 | | |
| Val | Val | Ala | Pro | Pro | Pro | Val | Val | Leu | Leu | | | | | | |
| | | 370 | | | | | 375 | | | | | | | | |

( 2 ) INFORMATION FOR SEQ ID NO:43:

( i ) SEQUENCE CHARACTERISTICS:
    ( A ) LENGTH: 30 base pairs (B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (v) FRAGMENT TYPE: N-terminal (v i) ORIGINAL SOURCE:
    (A) ORGANISM: Homo sapiens (v i i) IMMEDIATE SOURCE:
    (B) CLONE: Primer 154

(x i) SEQUENCE DESCRIPTION: SEQ ID NO:43:

ATCGCTCGAG CGTTATTTGA AAAGAAAGTG　　　　　　　　　　　　　　　　　　　　　　　　30

(2) INFORMATION FOR SEQ ID NO:44:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: N-terminal (v i) ORIGINAL SOURCE:
        (A) ORGANISM: Homo sapiens (v i i) IMMEDIATE SOURCE:
        (B) CLONE: Primer 151

(x i) SEQUENCE DESCRIPTION: SEQ ID NO:44:

ATCGGAATTC AAGCAGGACA ACAGGCGG　　　　　　　　　　　　　　　　　　　　　　　　28

(2) INFORMATION FOR SEQ ID NO:45:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v) FRAGMENT TYPE: N-terminal (v i) ORIGINAL SOURCE:
        (A) ORGANISM: Homo sapiens (v i i) IMMEDIATE SOURCE:
        (B) CLONE: Primer 156

(x i) SEQUENCE DESCRIPTION: SEQ ID NO:45:

ATCGTACGTA TTATTTGAAA AGAAAGTG　　　　　　　　　　　　　　　　　　　　　　　　28

We claim:

1. A pharmaceutical composition comprising an angiostatin fragment having endothelial cell proliferation inhibiting activity, said angiostatin fragment being a kringle 2–3 region or a kringle 1–2 region.

2. The composition of claim 1, wherein the angiostatin fragment has an endothelial cell $ED_{50}$ of less than about 500 nM.

3. The composition of claim 1, wherein the angiostatin fragment is derived from murine plasminogen, human plasminogen, rhesus plasminogen, porcine plasminogen or bovine plasminogen.

4. The composition of claim 1, wherein the angiostatin fragment has an amino acid sequence selected from the group consisting of SEQ ID NO:24; SEQ ID NO:25; SEQ ID NO:26; SEQ ID NO:27; SEQ ID NO:28; SEQ ID NO:34; SEQ ID NO:35; SEQ ID NO:36; SEQ ID NO:37; SEQ ID NO:38.

5. A substantially isolated angiostatin fragment, said angiostatin fragment being a kringle 2–3 region and having endothelial cell proliferation inhibiting activity.

6. The angiostatin fragment of claim 5, wherein the angiostatin fragment is derived from murine plasminogen, human plasminogen, rhesus plasminogen, porcine plasminogen or bovine plasminogen.

7. The angiostatin fragment of claim 5, wherein the angiostatin fragment has an amino acid sequence selected from the group consisting of SEQ ID NO:24; SEQ ID NO:25; SEQ ID NO:26; SEQ ID NO:27; or SEQ ID NO:28.

8. A substantially isolated angiostatin fragment, said angiostatin fragment being a kringle 1–2 region and having endothelial cell proliferation inhibiting activity.

9. The angiostatin fragment of claim 8, wherein the angiostatin fragment is derived from murine plasminogen, human plasminogen, rhesus plasminogen, porcine plasminogen or bovine plasminogen.

10. The angiostatin fragment of claim 8, wherein the angiostatin fragment has an amino acid sequence selected from the group consisting of SEQ ID NO:34; SEQ ID NO:35; SEQ ID NO:36; SEQ ID NO:37; or SEQ ID NO:38.

* * * * *

UNITED STATES PATENT AND TRADEMARK OFFICE
CERTIFICATE OF CORRECTION

PATENT NO. : 5,837,682
DATED : November 17, 1998
INVENTOR(S) : M. Judah Folkman et al.

It is certified that error appears in the above-identified patent and that said Letters Patent is hereby corrected as shown below:

On the title page, lines 4-5 of item number [75], after "Sweden;" please delete [Kim Lee Sim, Gaithersburg, Md].

Signed and Sealed this

Twenty-fourth Day of August, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,837,682

DATED : November 17, 1998

INVENTOR(S) : M. Judah Folkman et al.

It is certified that error appears in the above-identified patent and that said Letters Patent is hereby corrected as shown below:

In column 1, line 3, insert

--This invention was made with government support under Grant No.(s) CA 45548 by the National Institutes of Health. The government may have certain rights in the invention.--

Signed and Sealed this

Eighteenth Day of July, 2000

*Attest:*

Q. TODD DICKINSON

*Attesting Officer*     *Director of Patents and Trademarks*